(12) United States Patent
Rhoads

(10) Patent No.: US 7,724,920 B2
(45) Date of Patent: *May 25, 2010

(54) DIGITAL AUTHENTICATION WITH ANALOG DOCUMENTS

(75) Inventor: Geoffrey B. Rhoads, West Linn, OR (US)

(73) Assignee: Digimarc Corporation, Beaverton, OR (US)

( * ) Notice: Subject to any disclaimer, the term of this patent is extended or adjusted under 35 U.S.C. 154(b) by 2 days.

This patent is subject to a terminal disclaimer.

(21) Appl. No.: 11/927,168

(22) Filed: Oct. 29, 2007

(65) Prior Publication Data

US 2008/0216149 A1 Sep. 4, 2008

Related U.S. Application Data

(63) Continuation of application No. 11/382,459, filed on May 9, 2006, now Pat. No. 7,330,563, which is a continuation of application No. 10/164,899, filed on Jun. 4, 2002, now Pat. No. 7,043,052, which is a continuation of application No. 09/198,022, filed on Nov. 23, 1998, now Pat. No. 6,546,112, which is a continuation of application No. 08/763,847, filed on Dec. 4, 1996, now Pat. No. 5,841,886, which is a continuation of application No. 08/512,993, filed on Aug. 9, 1995, now abandoned, which is a continuation-in-part of application No. 08/436,098, filed on May 8, 1995, now Pat. No. 5,636,292, and a continuation-in-part of application No. 08/436,099, filed on May 8, 1995, now Pat. No. 5,710,834, and a continuation-in-part of application No. 08/436,102, filed on May 8, 1995, now Pat. No. 5,748,783, and a continuation-in-part of application No. 08/436,134, filed on May 8, 1995, now Pat. No. 5,748,763, and a continuation-in-part of application No. 08/438,159, filed on May 8, 1995, now Pat. No. 5,850,481.

(51) Int. Cl.
*H04K 1/00* (2006.01)
(52) U.S. Cl. .................................... 382/100; 340/5.86
(58) Field of Classification Search ................. 382/100, 382/135, 137, 232; 713/176; 380/287, 51, 380/54; 340/5.6, 5.86; 356/71; 283/74, 283/75, 77, 113, 901; 235/462.13
See application file for complete search history.

(56) References Cited

U.S. PATENT DOCUMENTS 4,590,366 A 5/1986 Rothfjell .................. 235/494

(Continued)

FOREIGN PATENT DOCUMENTS

DE 29 43 436 A1 5/1981

(Continued)

OTHER PUBLICATIONS

Bender et al., "Techniques for Data Hiding," SPIE vol. 2420, Jan. 1995, pp. 164-173.

(Continued)

*Primary Examiner*—Andrew W Johns

(57) ABSTRACT

The present claim relate generally to steganographic encoding and decoding. For example, one claim recites a method including: using a programmed electronic processor, generating authentication information corresponding to semantic information to be carried on or in a document; and incorporating the authentication information on or in the document, in which incorporated authentication information is to be later obtainable from the document for comparison with the semantic information, and in which the authentication information is steganographically incorporated on or in the document so as to be machine-readable from the document with visible light scanning. Of course, other claims and combinations are provided too.

5 Claims, 21 Drawing Sheets

U.S. PATENT DOCUMENTS

| | | | |
|---|---|---|---|
| 4,675,746 A | 6/1987 | Tetrick et al. | 358/296 |
| 4,689,477 A | 8/1987 | Goldman | 235/380 |
| 4,728,984 A | 3/1988 | Daniele | 355/6 |
| 4,972,476 A | 11/1990 | Nathans | 380/23 |
| 5,018,767 A | 5/1991 | Wicker | 283/67 |
| 5,091,966 A | 2/1992 | Bloomberg et al. | 382/21 |
| 5,221,833 A | 6/1993 | Hecht | 235/494 |
| 5,237,164 A | 8/1993 | Takada | 235/487 |
| 5,284,364 A | 2/1994 | Jain | 283/87 |
| 5,319,453 A | 6/1994 | Copriviza et al. | 348/6 |
| 5,321,751 A | 6/1994 | Ray et al. | 380/23 |
| 5,329,108 A | 7/1994 | Lamoure | 235/494 |
| 5,337,361 A | 8/1994 | Wang et al. | 380/51 |
| 5,379,345 A | 1/1995 | Greenberg | 380/23 |
| 5,384,846 A | 1/1995 | Berson et al. | 380/23 |
| 5,396,559 A | 3/1995 | McGrew | 380/54 |
| 5,436,970 A | 7/1995 | Ray et al. | 380/23 |
| 5,449,896 A | 9/1995 | Hecht et al. | 235/494 |
| 5,471,533 A | 11/1995 | Wang et al. | 380/51 |
| 5,495,581 A | 2/1996 | Tsai | 395/154 |
| 5,505,494 A | 4/1996 | Belluci et al. | 283/75 |
| 5,515,451 A | 5/1996 | Tsuji et al. | 382/135 |
| 5,629,770 A | 5/1997 | Brassil et al. | 358/261.1 |
| 5,636,292 A | 6/1997 | Rhoads | 382/232 |
| 5,646,997 A | 7/1997 | Barton | 380/23 |
| 5,652,626 A | 7/1997 | Kawakami et al. | 348/463 |
| 5,659,726 A | 8/1997 | Sandford, II et al. | 395/612 |
| 5,694,471 A | 12/1997 | Chen et al. | 380/25 |
| 5,710,834 A | 1/1998 | Rhoads | 382/232 |
| 5,721,788 A | 2/1998 | Powell et al. | 382/100 |
| 5,748,783 A | 5/1998 | Rhoads | 382/232 |
| 5,768,426 A | 6/1998 | Rhoads | 382/232 |
| 5,786,587 A | 7/1998 | Colgate, Jr. | 235/487 |
| 5,787,186 A | 7/1998 | Schroeder | 382/100 |
| 5,799,092 A | 8/1998 | Kristol et al. | 380/51 |
| 5,835,639 A | 11/1998 | Honsinger et al. | 382/278 |
| 5,841,886 A | 11/1998 | Rhoads | 382/115 |
| 5,845,008 A | 12/1998 | Katoh et al. | 382/217 |
| 5,850,481 A | 12/1998 | Rhoads | 382/232 |
| 5,864,622 A | 1/1999 | Marcus | 380/23 |
| 5,864,623 A | 1/1999 | Messina et al. | 380/23 |
| 5,907,149 A | 5/1999 | Marckini | 235/487 |
| 5,912,974 A | 6/1999 | Holloway et al. | 380/51 |
| 5,949,055 A | 9/1999 | Fleet et al. | 235/469 |
| 5,982,956 A | 11/1999 | Lahmi | 382/306 |
| 6,024,287 A | 2/2000 | Takai et al. | 235/493 |
| 6,076,738 A | 6/2000 | Bloomberg et al. | 235/494 |
| 6,243,480 B1 * | 6/2001 | Zhao et al. | 382/100 |
| 6,263,087 B1 | 7/2001 | Miller | 382/100 |
| 6,289,108 B1 | 9/2001 | Rhoads | 382/100 |
| 6,292,092 B1 | 9/2001 | Chow et al. | 340/5.6 |
| 6,343,138 B1 | 1/2002 | Rhoads | 382/100 |
| 6,408,082 B1 | 6/2002 | Rhoads et al. | 382/100 |
| 6,424,725 B1 | 7/2002 | Rhoads et al. | 382/100 |
| 6,546,112 B1 | 4/2003 | Rhoads | 382/100 |
| 6,674,886 B2 | 1/2004 | Davis et al. | 382/135 |
| 6,727,996 B1 | 4/2004 | Silverbrook et al. | 358/1.1 |
| 6,751,336 B2 | 6/2004 | Zhao et al. | 382/100 |
| 6,782,116 B1 | 8/2004 | Zhao et al. | 382/100 |
| 6,830,196 B1 | 12/2004 | Silverbrook et al. | 235/494 |
| 6,871,789 B2 | 3/2005 | Hilton et al. | 235/494 |
| 7,016,516 B2 | 3/2006 | Rhoads | 382/100 |
| 7,043,052 B2 | 5/2006 | Rhoads | 382/100 |
| 7,072,490 B2 | 7/2006 | Stach | 382/100 |
| 7,080,041 B2 | 7/2006 | Nagel | 705/51 |
| 7,099,019 B2 | 8/2006 | Silverbrook et al. | 358/1.1 |
| 7,181,042 B2 | 2/2007 | Tian | 382/100 |
| 7,239,734 B2 | 7/2007 | Alattar et al. | 382/135 |
| 7,269,275 B2 | 9/2007 | Carr et al. | 382/100 |
| 7,330,563 B2 | 2/2008 | Rhoads | 382/100 |
| 7,555,139 B2 | 6/2009 | Rhoads et al. | 382/100 |

FOREIGN PATENT DOCUMENTS

| | | |
|---|---|---|
| EP | 0 493 091 A1 | 12/1991 |
| EP | 0629972 A2 | 12/1994 |
| EP | 0642060 B1 | 4/1999 |
| EP | 0736860 B1 | 10/2002 |
| JP | 3-185585 A | 8/1991 |
| WO | WO9603286 A1 | 2/1996 |
| WO | WO 96/31049 A1 | 10/1996 |

OTHER PUBLICATIONS

Bruckstein, A.M.; Richardson, T.J., A holographic transform domain image watermarking method, Circuits, Systems, and Signal Processing vol. 17, No. 3, p. 361-89, 1998, This paper includes an appendix containing an internal memo of Bell Labs, which according to the authors of the paper, was dated Sep. 1994.

Burgett, et al., "A Novel Method for Copyright Labeling Digitized Image Data," Sep. 7, 1994.

Chen, et al, "Symmetric Phase-Only Matched Filtering of Fourier-Mellin Transforms for Image Registration and Recognition," IEEE Trans. On Pattern Analysis and Machine Intelligence, vol. 16, No. 12, Dec. 1994, pp. 1156-1168.

Guido, "Preventing Copying of Classified Information," IBM Technical Disclosure Bulletin, Sep. 1976 pp. 1469-1470.

Hara et al., "An Improved Method of Embedding Data Into Pictures by Modulo Masking," IEEE Transactions on Communications, 1988 vol. COM-36, No. 3, pp. 315-331.

Kawaguchi et al., "Principle and Applications of BPCS-Steganography," Proc. SPIE vol. 3528: Multimedia Systems and Applications, Nov. 2-4, 1998, pp. 464-473.

Koch et al., "Copyright Protection for Multimedia Data," Dec. 1994.

Komatsu et al., "A Proposal on Digital Watermarking in Document Image Communication and Its Application to Realizing a Signature," Electronics and Communications in Japan, Part I, vol. 73, No. 5, 1990, pp. 22-23.

Komatsu et al., "Authentication System Using Concealed Image in Telematics," Memoirs of the School of Science & Eng., Waseda Univ., No. 52, 1988, pp. 45-60.

Sheng, et al., "Experiments on pattern recognition using invariant Fourier-Mellin descriptors," J. Opt. Soc. Am. A, vol. 3, No. 6, Jun. 1986, pp. 771-776.

Szepanski, "A Signal Theoretic Method for Creating Forgery-Proof Documents for Automatic Verification", 1979 Carnahan Conference on Crime Countermeasures, University of Kentucky, Lexington, Kentucky, May 16-18, 1979.

Tanaka et al., "Embedding Secret Information into a Dithered Multi-level Image," IEEE, pp. 216-220, 1990.

Tanaka et al., "A Visual Retrieval System with Private Information for Image Database," Proc. Int'l Conf. on DSP Appl. & Tech., pp. 415-421, Oct. 1991.

Wagner, "Fingerprinting," IEEE. Symp. on Security and Privacy, 1983, pp. 18-22.

Xydeas et al., "Embedding Data Into Pictures by Modulo Masking," IEEE Transactions on Communications, 1984, vol. COM-32, No. 1, pp. 56-69.

Zhao. et al., "Embedding Robust Labels into Images for Copyright Protection," Proc. Of the Intern. Congress on Intel. Prop. Rights for Specialized Information, Knowledge and New Technologies (Vienna, Austria, Aug. 21-25, 1995).

Jul. 2, 2009 Notice of Allowance: Jun. 25, 2009 Amendment with RCE; Jun. 23, 2009 Interview Summary; Mar. 31, 2009 Final Office Action; all from assignee's U.S. Appl. No. 11/927,117.

* cited by examiner

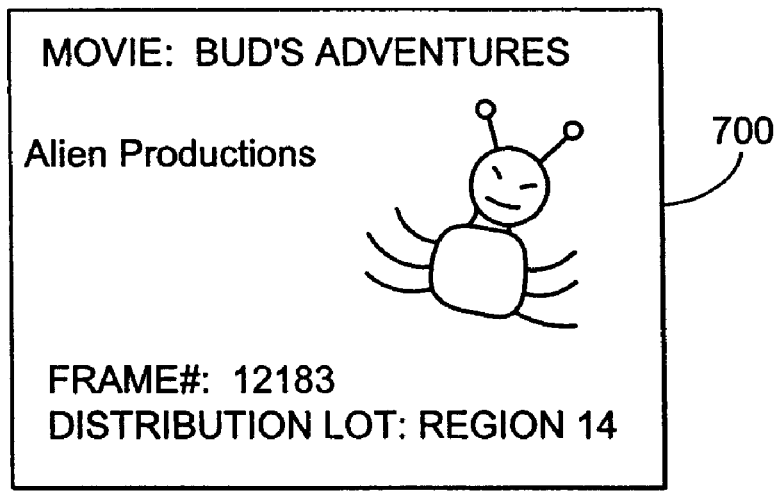
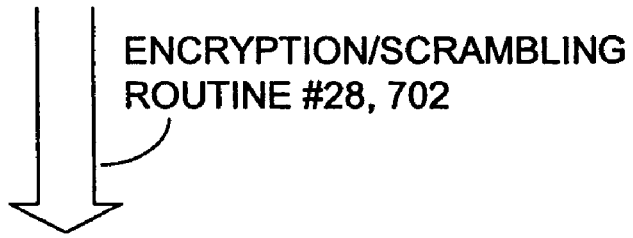
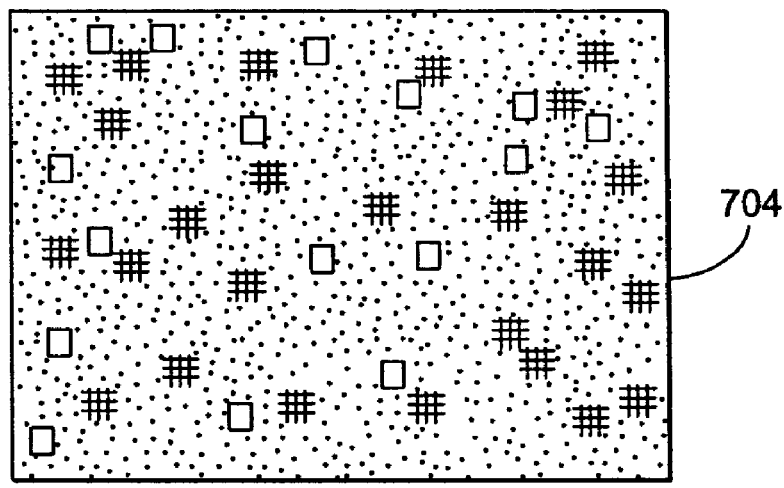
PSEUDO-RANDOM MASTER SNOWY IMAGE
(SCALED DOWN AND ADDED TO FRAME 12183)
FIG. 13

866

QUEST FOR MOSAICED KNOT PATTERNS WHICH "COVER" AND ARE COEXTENSIVE WITH ORIGINAL IMAGE; ALL ELEMENTAL KNOT PATTERNS CAN CONVEY THE SAME INFORMATION, SUCH AS A SIGNATURE, OR EACH CAN CONVEY A NEW MESSAGE IN A STEGANOGAPHIC SENSE

ELEMENTARY BUMP (DEFINED GROUPING OF PIXELS WITH WEIGHT VALUES)

EXAMPLE OF HOW MANY ELEMENTARY BUMPS, 900, WOULD BE ASSIGNED LOCATIONS IN AN IMAGE, AND THOSE LOCATIONS WOULD BE ASSOCIATED WITH A CORRESPONDING BIT PLANE IN THE N-BIT WORD, HERE TAKEN AS N=8 WITH INDEXES OF 0-7. ONE LOCATION, ASSOCIATED WITH BIT PLANE "5", HAS THE OVERLAY OF THE BUMP PROFILE DEPICTED.

TYPICAL TRANSACTION STEPS

1. READER SCANS IMAGE ON CARD, STORES IN MEMORY, EXTRACTS PERSON'S ID
2. OPTIONAL: USER KEYS IN PIN NUMBER
3. READER CALLS CENTRAL ACCOUNT DATA NETWORK, HANDSHAKES
4. READER SENDS ID, (PIN), MERCHANT INFORMATION, AND REQUESTED TRANSACTION AMOUNT TO CENTRAL NETWORK
5. CENTRAL NETWORK VERIFIES ID, PIN, MERCHANT INFO, AND ACCOUNT BALANCE
6. IF OK, CENTRAL NETWORK GENERATES TWENTY-FOUR SETS OF SIXTEEN DISTINCT RANDOM NUMBERS, WHERE THE RANDOM NUMBERS ARE INDEXES TO A SET OF 64K ORTHOGONAL SPATIAL PATTERNS
7. CENTRAL NETWORK TRANSMITS FIRST OK, AND THE SETS OF RANDOM NUMBERS
8. READER STEPS THROUGH THE TWENTY-FOUR SETS
   8A. READER ADDS TOGETHER SET OF ORTHOGONAL PATTERNS
   8B. READER PERFORMS DOT PRODUCT OF RESULTANT PATTERN AND CARD SCAN, STORES RESULT
9. READER TRANSMITS THE TWENTY-FOUR DOT PRODUCT RESULTS TO CENTRAL NETWORK
10. CENTRAL NETWORK CHECKS RESULTS AGAINST MASTER
11. CENTRAL NETWORK SENDS FINAL APPROVAL OR DENIAL
12. CENTRAL NETWORK DEBITS MERCHANT ACCOUNT, CREDITS CARD ACCOUNT

FIG. 25

THE NEGLIGIBLE-FRAUD CASH CARD SYSTEM

A BASIC FOUNDATION OF THE CASH CARD SYSTEM IS A 24-HOUR INFORMATION NETWORK, WHERE BOTH THE STATIONS WHICH CREATE THE PPHYSICAL CASH CARDS, 950, AND THE POINT-OF-SALES, 984, ARE ALL HOOKED UP TO THE SAME NETWORK CONTINUOUSLY

# DIGITAL AUTHENTICATION WITH ANALOG DOCUMENTS

RELATED APPLICATION DATA

This application is a continuation of U.S. patent application Ser. No. 11/382,459, filed May 9, 2006 (U.S. Pat. No. 7,330,563), which is a continuation of U.S. patent application Ser. No. 10/164,899 (U.S. Pat. No. 7,043,052). These above patent documents are hereby incorporated by reference. The Ser. No. 10/164,899 application is a continuation of application Ser. No. 09/198,022 (U.S. Pat. No. 6,546,112), filed Nov. 23, 1998, which is a continuation of application Ser. No. 08/763,847 (U.S. Pat. No. 5,841,886), filed Dec. 4, 1996, which is a continuation of application Ser. No. 08/512,993, filed Aug. 9, 1995, now abandoned, which is a continuation-in-part of each of application Ser. No. 08/436,098 (U.S. Pat. No. 5,636,292), Ser. No. 08/436,099 (U.S. Pat. No. 5,710,834), Ser. No. 08/436,102 (U.S. Pat. No. 5,748,783), Ser. No. 08/436,134 (U.S. Pat. No. 5,748,763), and Ser. No. 08/438,159 (U.S. Pat. No. 5,850,481), each filed May 8, 1995.

Application Ser. No. 08/512,993 is also related to application Ser. No. 08/327,426 (now U.S. Pat. No. 5,768,426), filed Oct. 21, 1994, which is a continuation-in-part of application Ser. No. 08/215,289, filed Mar. 17, 1994, now abandoned, which is a continuation-in-part of application Ser. No. 08/154,866, filed Nov. 18, 1993, now abandoned.

TECHNICAL FIELD

The present invention relates to the field of photograph-based identification systems.

BACKGROUND AND SUMMARY OF THE INVENTION

The use of photograph-based identification ("photo ID") systems is pervasive. Drivers' licenses, passports, visas, government employee cards, immigration documents, and now, more frequently, credit cards and cash transaction cards carry a photograph of the card bearer for identification purposes. Many industries require that their employees carry photo ID on the job.

Fraudulent use of photo ID systems may occur where, for example, an otherwise legitimate passport is modified such that the original photograph is swapped with that of another person, thereby enabling the other person to travel, at least temporarily, under the guise of the original passport holder.

Even in the absence of photograph swapping or alteration, it is oftentimes difficult to confirm by inspection that the individual depicted in the photograph of the identification card is indeed the bearer of the card.

One aspect of this invention provides for enhanced security and certainty in the use of photo ID documents.

Another aspect of this invention pertains to unauthorized use and outright piracy of proprietary source material which, since time immemorial, has been a source of lost revenue, confusion, and artistic corruption.

These historical problems have been compounded by the advent of digital technology. With it, the technology of copying materials and redistributing them in unauthorized manners has reached new heights of sophistication, and more importantly, omnipresence. Lacking objective means for comparing an alleged copy of material with the original, owners and litigation proceedings are left with a subjective opinion of whether the alleged copy is stolen, or has been used in an unauthorized manner. Furthermore, there is no simple means of tracing a path to an original purchaser of the material—something which can be valuable in tracing where a possible "leak" of the material first occurred.

A variety of methods for protecting commercial material have been attempted. One is to scramble signals via an encoding method prior to distribution, and descramble prior to use. This technique, however, is of little use in mass market audio and visual media, where even a few dollars extra cost causes a major reduction in market, and where the signal must eventually be descrambled to be perceived, and thus can be easily recorded.

Another class of techniques relies on modification of source audio or video signals to include a subliminal identification signal, which can be sensed by electronic means. Examples of such systems are found in U.S. Pat. No. 4,972,471 and European patent publication EP 441,702, as well as in Komatsu et al, "Authentication System Using Concealed Image in Telematics," Memoirs of the School of Science & Engineering, Waseda University, No. 52, p. 45-60 (1988) (Komatsu uses the term "digital watermark" for this technique). These techniques have the common characteristic that deterministic signals with well defined patterns and sequences within the source material convey the identification information. For certain applications this is not a drawback. But in general, this is an inefficient form of embedding identification information for a variety of reasons: (a) the whole of the source material is not used; (b) deterministic patterns have a higher likelihood of being discovered and removed by a would-be pirate; and (c) the signals are not generally 'holographic' in that identifications may be difficult to make given only sections of the whole. ('Holographic' is used herein to refer to the property that the identification information is distributed globally throughout the coded signal, and can be fully discerned from an examination of even a fraction of the coded signal. Coding of this type is sometimes termed "distributed" herein.)

Among the cited references are descriptions of several programs which perform steganography—described in one document as " . . . the ancient art of hiding information in some otherwise inconspicuous information." These programs variously allow computer users to hide their own messages inside digital image files and digital audio files. All do so by toggling the least significant bit (the lowest order bit of a single data sample) of a given audio data stream or rasterized image. Some of these programs embed messages quite directly into the least significant bit, while other "pre-encrypt" or scramble a message first and then embed the encrypted data into the least significant bit.

Our current understanding of these programs is that they generally rely on error-free transmission of the of digital data in order to correctly transmit a given message in its entirety. Typically the message is passed only once, i.e., it is not repeated. These programs also seem to "take over" the least significant bit entirely, where actual data is obliterated and the message placed accordingly. This might mean that such codes could be easily erased by merely stripping off the least significant bit of all data values in a given image or audio file. It is these and other considerations which suggest that the only similarity between our invention and the established art of steganography is in the placement of information into data files with minimal perceptibility. The specifics of embedding and the uses of that buried information diverge from there.

Another cited reference is U.S. Pat. No. 5,325,167 to Melen. In the service of authenticating a given document, the high precision scanning of that document reveals patterns and "microscopic grain structure" which apparently is a kind of unique fingerprint for the underlying document media, such as paper itself or post-applied materials such as toner. Melen further teaches that scanning and storing this fingerprint can later be used in authentication by scanning a purported document and comparing it to the original fingerprint. Applicant is aware of a similar idea employed in the very high precision recording of credit card magnetic strips, as reported in the Feb. 8, 1994, Wall Street Journal, page B1, wherein very fine magnetic fluxuations tend to be unique from one card to the next, so that credit card authentication can be achieved through pre-recording these fluxuations later to be compared to the recordings of the purportedly same credit card.

Both of the foregoing techniques appear to rest on the same identification principles on which the mature science of fingerprint analysis rests: the innate uniqueness of some localized physical property. These methods then rely upon a single judgement and/or measurement of "similarity" or "correlation" between a suspect and a pre-recording master. Though fingerprint analysis has brought this to a high art, these methods are nevertheless open to a claim that preparations of the samples, and the "filtering" and "scanner specifications" of Melen's patent, unavoidably tend to bias the resulting judgement of similarity, and would create a need for more esoteric "expert testimony" to explain the confidence of a found match or mis-match. It is desirable to avoid this reliance on expert testimony and to place the confidence in a match into simple "coin flip" vernacular, i.e., what are the odds you can call the correct coin flip 16 times in a row. Attempts to identify fragments of a fingerprint, document, or otherwise, exacerbate this issue of confidence in a judgment. It is desirable, therefore, to objectively apply the intuitive "coin flip" confidence to the smallest fragment possible. Also, storing unique fingerprints for each and every document or credit card magnetic strip, and having these fingerprints readily available for later cross-checking, should prove to be quite an economic undertaking. It would be preferred to allow for the "re-use" of noise codes and "snowy images" in the service of easing storage requirements.

Despite the foregoing and other diverse work in the field of identification/authentication, there still remains a need for a reliable and efficient method for performing a positive identification between a copy of an original signal and the original. Desirably, this method should not only perform identification, it should also be able to convey source-version information in order to better pinpoint the point of sale. The method should not compromise the innate quality of material which is being sold, as does the placement of localized logos on images. The method should be robust so that an identification can be made even after multiple copies have been made and/or compression and decompression of the signal has taken place. The identification method should be largely uneraseable or "uncrackable." The method should be capable of working even on fractional pieces of the original signal, such as a 10 second "riff" of an audio signal or the "clipped and pasted" sub-section of an original image.

The existence of such a method would have profound consequences on piracy in that it could (a) cost effectively monitor for unauthorized uses of material and perform "quick checks"; (b) become a deterrent to unauthorized uses when the method is known to be in use and the consequences well publicized; and (c) provide unequivocal proof of identity, similar to fingerprint identification, in litigation, with potentially more reliability than that of fingerprinting.

In accordance with exemplary embodiments of the invention, the foregoing and additional objects are achieved by embedding an imperceptible identification code throughout a source signal. In the preferred embodiment, this embedding is achieved by modulating the source signal with a small noise signal in a coded fashion. More particularly, bits of a binary identification code are referenced, one at a time, to control modulation of the source signal with the noise signal.

The copy with the embedded signal (the "encoded" copy) becomes the material which is sold, while the original is secured in a safe place. The new copy is nearly identical to the original except under the finest of scrutiny; thus, its commercial value is not compromised. After the new copy has been sold and distributed and potentially distorted by multiple copies, the present disclosure details methods for positively identifying any suspect signal against the original.

Among its other advantages, the preferred embodiments' use of identification signals which are global (holographic) and which mimic natural noise sources allows the maximization of identification signal energy, as opposed to merely having it present 'somewhere in the original material.' This allows the identification coding to be much more robust in the face of thousands of real world degradation processes and material transformations, such as cutting and cropping of imagery.

BRIEF DESCRIPTION OF THE DRAWINGS

FIG. 13 shows an embodiment of the present invention in which a pseudo-random noise frame is generated from an image.

FIGS. 22-26 detail aspects of a security card according to one embodiment of the present invention.

DETAILED DESCRIPTION OF PREFERRED EMBODIMENTS

In the following discussion of an illustrative embodiment, the words "signal" and "image" are used interchangeably to refer to both one, two, and even beyond two dimensions of digital signal. Examples will routinely switch back and forth between a one dimensional audio-type digital signal and a two dimensional image-type digital signal.

Figure 1:
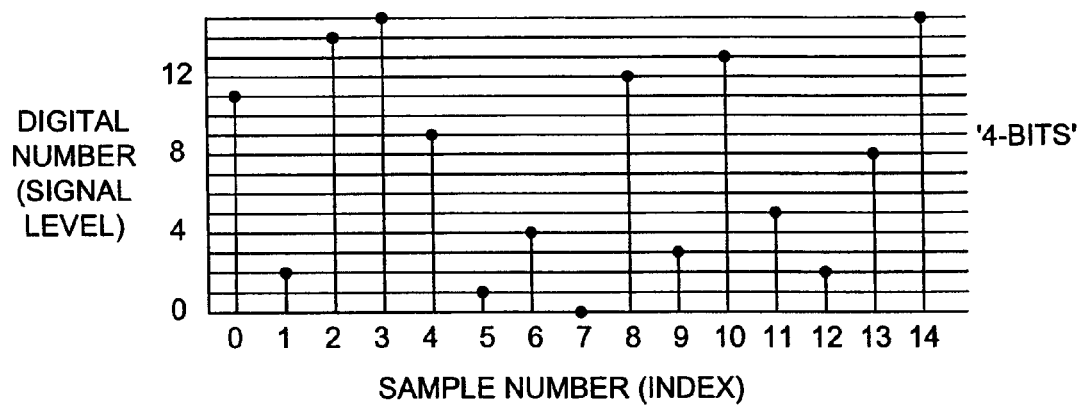
FIG. 1 is a simple and classic depiction of a one dimensional digital signal which is discretized in both axes.

In order to fully describe the details of an illustrative embodiment of the invention, it is necessary first to describe the basic properties of a digital signal. FIG. 1 shows a classic representation of a one dimensional digital signal. The x-axis defines the index numbers of sequence of digital "samples," and the y-axis is the instantaneous value of the signal at that sample, being constrained to exist only at a finite number of levels defined as the "binary depth" of a digital sample. The example depicted in FIG. 1 has the value of 2 to the fourth power, or "4 bits," giving 16 allowed states of the sample value.

For audio information such as sound waves, it is commonly accepted that the digitization process discretizes a continuous phenomena both in the time domain and in the signal level domain. As such, the process of digitization itself introduces a fundamental error source, in that it cannot record detail smaller than the discretization interval in either domain. The industry has referred to this, among other ways, as "aliasing" in the time domain, and "quantization noise" in the signal level domain. Thus, there will always be a basic error floor of a digital signal. Pure quantization noise, measured in a root mean square sense, is theoretically known to have the value of one over the square root of twelve, or about 0.29 DN, where DN stands for 'Digital Number' or the finest unit increment of the signal level. For example, a perfect 12-bit digitizer will have 4096 allowed DN with an innate root mean square noise floor of ~0.29 DN.

All known physical measurement processes add additional noise to the transformation of a continuous signal into the digital form. The quantization noise typically adds in quadrature (square root of the mean squares) to the "analog noise" of the measurement process, as it is sometimes referred to.

With almost all commercial and technical processes, the use of the decibel scale is used as a measure of signal and noise in a given recording medium. The expression "signal-to-noise ratio" is generally used, as it will be in this disclosure. As an example, this disclosure refers to signal to noise ratios in terms of signal power and noise power, thus 20 dB represents a 10 times increase in signal amplitude.

In summary, the presently preferred embodiments of the invention embed an N-bit value onto an entire signal through the addition of a very low amplitude encodation signal which has the look of pure noise. N is usually at least 8 and is capped on the higher end by ultimate signal-to-noise considerations and "bit error" in retrieving and decoding the N-bit value. As a practical matter, N is chosen based on application specific considerations, such as the number of unique different "signatures" that are desired. To illustrate, if N=128, then the number of unique digital signatures is in excess of $10^{38}$ ($2^{128}$). This number is believed to be more than adequate to both identify the material with sufficient statistical certainty and to index exact sale and distribution information.

The amplitude or power of this added signal is determined by the aesthetic and informational considerations of each and every application using the present methodology. For instance, non-professional video can stand to have a higher embedded signal level without becoming noticeable to the average human eye, while high precision audio may only be able to accept a relatively small signal level lest the human ear perceive an objectionable increase in "hiss." These statements are generalities and each application has its own set of criteria in choosing the signal level of the embedded identification signal. The higher the level of embedded signal, the more corrupted a copy can be and still be identified. On the other hand, the higher the level of embedded signal, the more objectionable the perceived noise might be, potentially impacting the value of the distributed material.

To illustrate the range of different applications to which the principles of the present invention can be applied, the present specification details two different systems. The first (termed, for lack of a better name, a "batch encoding" system), applies identification coding to an existing data signal. The second (termed, for lack of a better name, a "real time encoding" system), applies identification coding to a signal as it is produced. Those skilled in the art will recognize that the principles of the present invention can be applied in a number of other contexts in addition to these particularly described.

The discussions of these two systems can be read in either order. Some readers may find the latter more intuitive than the former; for others the contrary may be true.

Batch Encoding

The following discussion of a first class of embodiments is best prefaced by a section defining relevant terms:

The original signal refers to either the original digital signal or the high quality digitized copy of a non-digital original.

The N-bit identification word refers to a unique identification binary value, typically having N range anywhere from 8 to 128, which is the identification code ultimately placed onto the original signal via the disclosed transformation process. In the illustrated embodiment, each N-bit identification word begins with the sequence of values '0101,' which is used to determine an optimization of the signal-to-noise ratio in the identification procedure of a suspect signal (see definition below).

The m'th bit value of the N-bit identification word is either a zero or one corresponding to the value of the m'th place, reading left to right, of the N-bit word. E.g., the first (m=1) bit value of the N=8 identification word 01110100 is the value '0;' the second bit value of this identification word is '1', etc.

The m'th individual embedded code signal refers to a signal which has dimensions and extent precisely equal to the original signal (e.g. both are a 512 by 512 digital image), and which is (in the illustrated embodiment) an independent pseudo-random sequence of digital values. "Pseudo" pays homage to the difficulty in philosophically defining pure randomness, and also indicates that there are various acceptable ways of generating the "random" signal. There will be exactly N individual embedded code signals associated with any given original signal.

The acceptable perceived noise level refers to an application-specific determination of how much "extra noise," i.e. amplitude of the composite embedded code signal described next, can be added to the original signal and still have an acceptable signal to sell or otherwise distribute. This disclosure uses a 1 dB increase in noise as a typical value which might be acceptable, but this is quite arbitrary.

The composite embedded code signal refers to the signal which has dimensions and extent precisely equal to the original signal, (e.g. both are a 512 by 512 digital image), and which contains the addition and appropriate attenuation of the N individual embedded code signals. The individual embedded signals are generated on an arbitrary scale, whereas the amplitude of the composite signal must not exceed the pre-set acceptable perceived noise level, hence the need for "attenuation" of the N added individual code signals.

The distributable signal refers to the nearly similar copy of the original signal, consisting of the original signal plus the composite embedded code signal. This is the signal which is distributed to the outside community, having only slightly higher but acceptable "noise properties" than the original.

A suspect signal refers to a signal which has the general appearance of the original and distributed signal and whose potential identification match to the original is being questioned. The suspect signal is then analyzed to see if it matches the N-bit identification word.

The detailed methodology of this first embodiment begins by stating that the N-bit identification word is encoded onto the original signal by having each of the m bit values multiply their corresponding individual embedded code signals, the resultant being accumulated in the composite signal, the fully summed composite signal then being attenuated down to the acceptable perceived noise amplitude, and the resultant composite signal added to the original to become the distributable signal.

The original signal, the N-bit identification word, and all N individual embedded code signals are then stored away in a secured place. A suspect signal is then found. This signal may have undergone multiple copies, compressions and decompressions, resamplings onto different spaced digital signals, transfers from digital to analog back to digital media, or any combination of these items. IF the signal still appears similar to the original, i.e. its innate quality is not thoroughly destroyed by all of these transformations and noise additions, then depending on the signal to noise properties of the embedded signal, the identification process should function to some objective degree of statistical confidence. The extent of corruption of the suspect signal and the original acceptable perceived noise level are two key parameters in determining an expected confidence level of identification.

The identification process on the suspected signal begins by resampling and aligning the suspected signal onto the digital format and extent of the original signal. Thus, if an image has been reduced by a factor of two, it needs to be digitally enlarged by that same factor. Likewise, if a piece of music has been "cut out," but may still have the same sampling rate as the original, it is necessary to register this cut-out piece to the original, typically done by performing a local digital cross-correlation of the two signals (a common digital operation), finding at what delay value the correlation peaks, then using this found delay value to register the cut piece to a segment of the original.

Once the suspect signal has been sample-spacing matched and registered to the original, the signal levels of the suspect signal should be matched in an rms sense to the signal level of the original. This can be done via a search on the parameters of offset, amplification, and gamma being optimized by using the minimum of the mean squared error between the two signals as a function of the three parameters. We can call the suspect signal normalized and registered at this point, or just normalized for convenience.

The newly matched pair then has the original signal subtracted from the normalized suspect signal to produce a difference signal. The difference signal is then cross-correlated with each of the N individual embedded code signals and the peak cross-correlation value recorded. The first four bit code ('0101') is used as a calibrator both on the mean values of the zero value and the one value, and on further registration of the two signals if a finer signal to noise ratio is desired (i.e., the optimal separation of the 0101 signal will indicate an optimal registration of the two signals and will also indicate the probable existence of the N-bit identification signal being present.)

The resulting peak cross-correlation values will form a noisy series of floating point numbers which can be transformed into 0's and 1's by their proximity to the mean values of 0 and 1 found by the 0101 calibration sequence. If the suspect signal has indeed been derived from the original, the identification number resulting from the above process will match the N-bit identification word of the original, bearing in mind either predicted or unknown "bit error" statistics. Signal-to-noise considerations will determine if there will be some kind of "bit error" in the identification process, leading to a form of X % probability of identification where X might be desired to be 99.9% or whatever. If the suspect copy is indeed not a copy of the original, an essentially random sequence of 0's and 1's will be produced, as well as an apparent lack of separation of the resultant values. This is to say, if the resultant values are plotted on a histogram, the existence of the N-bit identification signal will exhibit strong bi-level characteristics, whereas the non-existence of the code, or the existence of a different code of a different original, will exhibit a type of random gaussian-like distribution. This histogram separation alone should be sufficient for an identification, but it is even stronger proof of identification when an exact binary sequence can be objectively reproduced.

Specific Example

Imagine that we have taken a valuable picture of two heads of state at a cocktail party, pictures which are sure to earn some reasonable fee in the commercial market. We desire to sell this picture and ensure that it is not used in an unauthorized or uncompensated manner. This and the following steps are summarized in FIG. 2.

Assume the picture is transformed into a positive color print. We first scan this into a digitized form via a normal high quality black and white scanner with a typical photometric spectral response curve. (It is possible to get better ultimate signal to noise ratios by scanning in each of the three primary colors of the color image, but this nuance is not central to describing the basic process.)

Let us assume that the scanned image now becomes a 4000 by 4000 pixel monochrome digital image with a grey scale accuracy defined by 12-bit grey values or 4096 allowed levels. We will call this the "original digital image" realizing that this is the same as our "original signal" in the above definitions.

During the scanning process we have arbitrarily set absolute black to correspond to digital value '30'. We estimate that there is a basic 2 Digital Number root mean square noise existing on the original digital image, plus a theoretical noise (known in the industry as "shot noise") of the square root of the brightness value of any given pixel. In formula, we have:

$$<\text{RMS Noise}_{n,m}> = \text{sqrt}(4+(V_{n,m}-30)) \qquad (1)$$

Here, n and m are simple indexing values on rows and columns of the image ranging from 0 to 3999. Sqrt is the square root. V is the DN of a given indexed pixel on the original digital image. The < > brackets around the RMS noise merely indicates that this is an expected average value, where it is clear that each and every pixel will have a random error individually. Thus, for a pixel value having 1200 as a digital number or "brightness value", we find that its expected rms noise value is sqrt(1204)=34.70, which is quite close to 34.64, the square root of 1200.

We furthermore realize that the square root of the innate brightness value of a pixel is not precisely what the eye perceives as a minimum objectionable noise, thus we come up with the formula:

$$<\text{RMS Addable Noise}_{n,m}> = X*\text{sqrt}(4+(V_{n,m}-30)^{\wedge}Y) \quad (2)$$

Where X and Y have been added as empirical parameters which we will adjust, and "addable" noise refers to our acceptable perceived noise level from the definitions above. We now intend to experiment with what exact value of X and Y we can choose, but we will do so at the same time that we are performing the next steps in the process.

The next step in our process is to choose N of our N-bit identification word. We decide that a 16 bit main identification value with its 65536 possible values will be sufficiently large to identify the image as ours, and that we will be directly selling no more than 128 copies of the image which we wish to track, giving 7 bits plus an eighth bit for an odd/even adding of the first 7 bits (i.e. an error checking bit on the first seven). The total bits required now are at 4 bits for the 0101 calibration sequence, 16 for the main identification, 8 for the version, and we now throw in another 4 as a further error checking value on the first 28 bits, giving 32 bits as N. The final 4 bits can use one of many industry standard error checking methods to choose its four values.

We now randomly determine the 16 bit main identification number, finding for example, 1101 0001 1001 1110; our first versions of the original sold will have all 0's as the version identifier, and the error checking bits will fall out where they may. We now have our unique 32 bit identification word which we will embed on the original digital image.

To do this, we generate 32 independent random 4000 by 4000 encoding images for each bit of our 32 bit identification word. The manner of generating these random images is revealing. There are numerous ways to generate these. By far the simplest is to turn up the gain on the same scanner that was used to scan in the original photograph, only this time placing a pure black image as the input, then scanning this 32 times. The only drawback to this technique is that it does require a large amount of memory and that "fixed pattern" noise will be part of each independent "noise image." But, the fixed pattern noise can be removed via normal "dark frame" subtraction techniques. Assume that we set the absolute black average value at digital number '100,' and that rather than finding a 2 DN rms noise as we did in the normal gain setting, we now find an rms noise of 10 DN about each and every pixel's mean value.

We next apply a mid-spatial-frequency bandpass filter (spatial convolution) to each and every independent random image, essentially removing the very high and the very low spatial frequencies from them. We remove the very low frequencies because simple real-world error sources like geometrical warping, splotches on scanners, mis-registrations, and the like will exhibit themselves most at lower frequencies also, and so we want to concentrate our identification signal at higher spatial frequencies in order to avoid these types of corruptions. Likewise, we remove the higher frequencies because multiple generation copies of a given image, as well as compression-decompression transformations, tend to wipe out higher frequencies anyway, so there is no point in placing too much identification signal into these frequencies if they will be the ones most prone to being attenuated. Therefore, our new filtered independent noise images will be dominated by mid-spatial frequencies. On a practical note, since we are using 12-bit values on our scanner and we have removed the DC value effectively and our new rms noise will be slightly less than 10 digital numbers, it is useful to boil this down to a 6-bit value ranging from −32 through 0 to 31 as the resultant random image.

Next we add all of the random images together which have a '1' in their corresponding bit value of the 32-bit identification word, accumulating the result in a 16-bit signed integer image. This is the unattenuated and un-scaled version of the composite embedded signal.

Next we experiment visually with adding the composite embedded signal to the original digital image, through varying the X and Y parameters of equation 2. In formula, we visually iterate to both maximize X and to find the appropriate Y in the following:

$$V_{dist;n,m} = V_{orig;n,m} + V_{comp;n,m}*X*\text{sqrt}(4+V_{orig;n,m}^{\wedge}Y) \quad (3)$$

where dist refers to the candidate distributable image, i.e. we are visually iterating to find what X and Y will give us an acceptable image; orig refers to the pixel value of the original image; and comp refers to the pixel value of the composite image. The n's and m's still index rows and columns of the image and indicate that this operation is done on all 4000 by 4000 pixels. The symbol V is the DN of a given pixel and a given image.

As an arbitrary assumption, now, we assume that our visual experimentation has found that the value of X=0.025 and Y=0.6 are acceptable values when comparing the original image with the candidate distributable image. This is to say, the distributable image with the "extra noise" is acceptably close to the original in an aesthetic sense. Note that since our individual random images had a random rms noise value around 10 DN, and that adding approximately 16 of these images together will increase the composite noise to around 40 DN, the X multiplication value of 0.025 will bring the added rms noise back to around 1 DN, or half the amplitude of our innate noise on the original. This is roughly a 1 dB gain in noise at the dark pixel values and correspondingly more at the brighter values modified by the Y value of 0.6.

So with these two values of X and Y, we now have constructed our first versions of a distributable copy of the original. Other versions will merely create a new composite signal and possibly change the X slightly if deemed necessary. We now lock up the original digital image along with the 32-bit identification word for each version, and the 32 independent random 4-bit images, waiting for our first case of a suspected piracy of our original. Storage wise, this is about 14 Megabytes for the original image and 32*0.5 bytes*16 million=~256 Megabytes for the random individual encoded images. This is quite acceptable for a single valuable image. Some storage economy can be gained by simple lossless compression.

Finding a Suspected Piracy of Our Image

Figure 3:
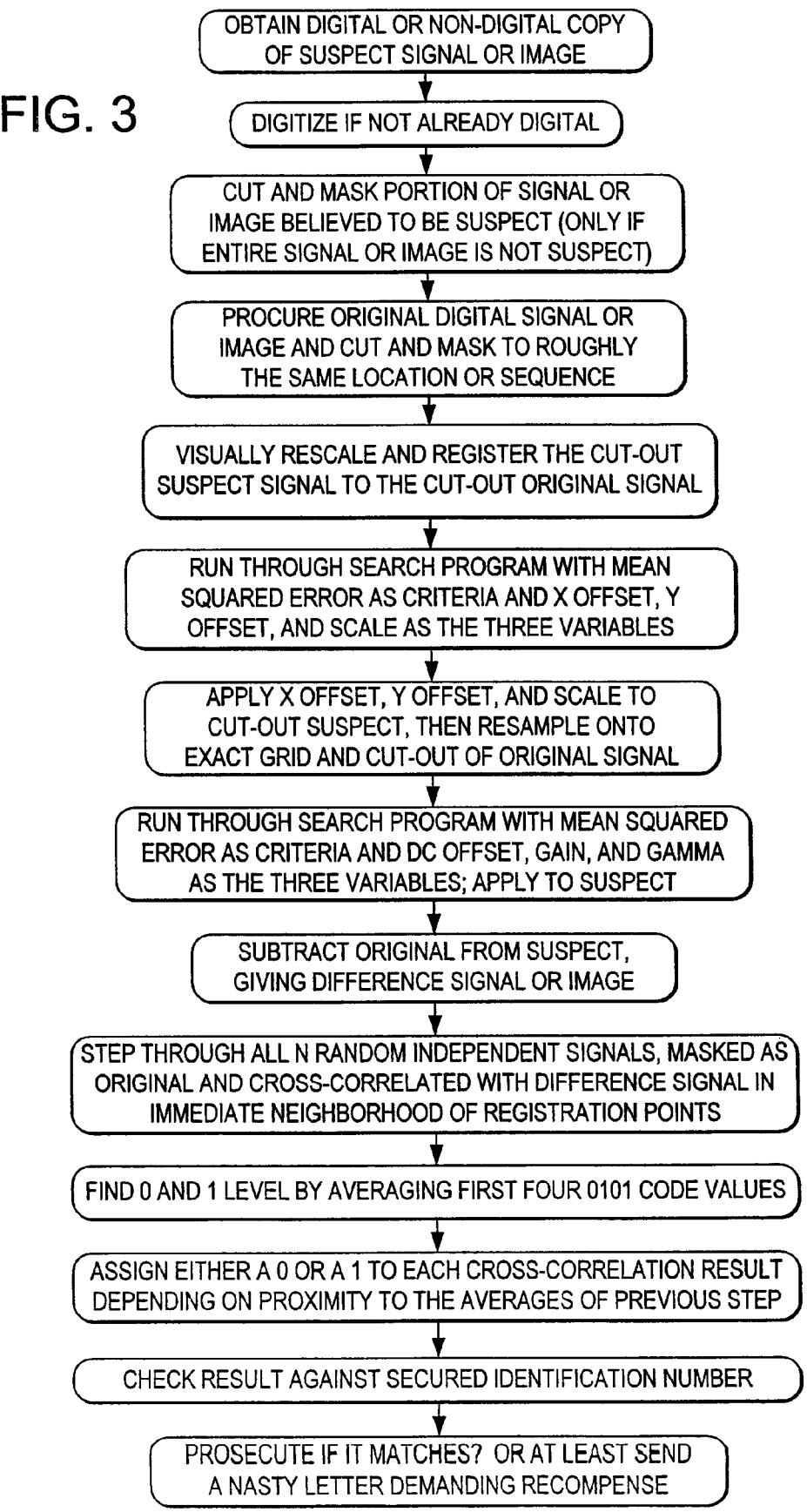
FIG. 3 is a step-wise description of how a suspected copy of an original is identified.

We sell our image and several months later find our two heads of state in the exact poses we sold them in, seemingly cut and lifted out of our image and placed into another stylized background scene. This new "suspect" image is being printed in 100,000 copies of a given magazine issue, let us say. We now go about determining if a portion of our original image has indeed been used in an unauthorized manner. FIG. 3 summarizes the details.

The first step is to take an issue of the magazine, cut out the page with the image on it, then carefully but not too carefully cut out the two figures from the background image using ordinary scissors. If possible, we will cut out only one connected piece rather than the two figures separately. We paste this onto a black background and scan this into a digital form. Next we electronically flag or mask out the black background, which is easy to do by visual inspection.

We now procure the original digital image from our secured place along with the 32-bit identification word and the 32 individual embedded images. We place the original digital image onto our computer screen using standard image manipulation software, and we roughly cut along the same borders as our masked area of the suspect image, masking this image at the same time in roughly the same manner. The word 'roughly' is used since an exact cutting is not needed, it merely aids the identification statistics to get it reasonably close.

Next we rescale the masked suspect image to roughly match the size of our masked original digital image, that is, we digitally scale up or down the suspect image and roughly overlay it on the original image. Once we have performed this rough registration, we then throw the two images into an automated scaling and registration program. The program performs a search on the three parameters of x position, y position, and spatial scale, with the figure of merit being the mean squared error between the two images given any given scale variable and x and y offset. This is a fairly standard image processing methodology. Typically this would be done using generally smooth interpolation techniques and done to sub-pixel accuracy. The search method can be one of many, where the simplex method is a typical one.

Once the optimal scaling and x-y position variables are found, next comes another search on optimizing the black level, brightness gain, and gamma of the two images. Again, the figure of merit to be used is mean squared error, and again the simplex or other search methodologies can be used to optimize the three variables. After these three variables are optimized, we apply their corrections to the suspect image and align it to exactly the pixel spacing and masking of the original digital image and its mask. We can now call this the standard mask.

The next step is to subtract the original digital image from the newly normalized suspect image only within the standard mask region. This new image is called the difference image.

Then we step through all 32 individual random embedded images, doing a local cross-correlation between the masked difference image and the masked individual embedded image. 'Local' refers to the idea that one need only start correlating over an offset region of +/−1 pixels of offset between the nominal registration points of the two images found during the search procedures above. The peak correlation should be very close to the nominal registration point of 0,0 offset, and we can add the 3 by 3 correlation values together to give one grand correlation value for each of the 32 individual bits of our 32-bit identification word.

After doing this for all 32 bit places and their corresponding random images, we have a quasi-floating point sequence of 32 values. The first four values represent our calibration signal of 0101. We now take the mean of the first and third floating point value and call this floating point value '0,' and we take the mean of the second and the fourth value and call this floating point value '1.' We then step through all remaining 28 bit values and assign either a '0' or a '1' based simply on which mean value they are closer to. Stated simply, if the suspect image is indeed a copy of our original, the embedded 32-bit resulting code should match that of our records, and if it is not a copy, we should get general randomness. The third and the fourth possibilities of 3) Is a copy but doesn't match identification number and 4) isn't a copy but does match are, in the case of 3), possible if the signal to noise ratio of the process has plummeted, i.e. the 'suspect image' is truly a very poor copy of the original, and in the case of 4) is basically one chance in four billion since we were using a 32-bit identification number. If we are truly worried about 4), we can just have a second independent lab perform their own tests on a different issue of the same magazine. Finally, checking the error-check bits against what the values give is one final and possibly overkill check on the whole process. In situations where signal to noise is a possible problem, these error checking bits might be eliminated without too much harm.

Benefits

Now that a full description of the first embodiment has been described via a detailed example, it is appropriate to point out the rationale of some of the process steps and their benefits.

The ultimate benefits of the foregoing process are that obtaining an identification number is fully independent of the manners and methods of preparing the difference image. That is to say, the manners of preparing the difference image, such as cutting, registering, scaling, etcetera, cannot increase the odds of finding an identification number when none exists; it only helps the signal-to-noise ratio of the identification process when a true identification number is present. Methods of preparing images for identification can be different from each other even, providing the possibility for multiple independent methodologies for making a match.

The ability to obtain a match even on sub-sets of the original signal or image is a key point in today's information-rich world. Cutting and pasting both images and sound clips is becoming more common, allowing such an embodiment to be used in detecting a copy even when original material has been thus corrupted. Finally, the signal to noise ratio of matching should begin to become difficult only when the copy material itself has been significantly altered either by noise or by significant distortion; both of these also will affect that copy's commercial value, so that trying to thwart the system can only be done at the expense of a huge decrease in commercial value.

An early conception of this invention was the case where only a single "snowy image" or random signal was added to an original image, i.e. the case where N=1. "Decoding" this signal would involve a subsequent mathematical analysis using (generally statistical) algorithms to make a judgment on the presence or absence of this signal. The reason this approach was abandoned as the preferred embodiment was that there was an inherent gray area in the certainty of detecting the presence or absence of the signal. By moving onward to a multitude of bit planes, i.e. N>1, combined with simple pre-defined algorithms prescribing the manner of choosing between a "0" and a "1", the invention moved the certainty question from the realm of expert statistical analysis into the realm of guessing a random binary event such as a coin flip. This is seen as a powerful feature relative to the intuitive acceptance of this invention in both the courtroom and the marketplace. The analogy which summarizes the inventor's thoughts on this whole question is as follows: The search for a single identification signal amounts to calling a coin flip only once, and relying on arcane experts to make the call; whereas the N>1 preferred embodiment of this invention relies on the broadly intuitive principle of correctly calling a coin flip N times in a row. This situation is greatly exacerbated, i.e. the problems of "interpretation" of the presence of a single signal, when images and sound clips get smaller and smaller in extent.

Another important reason that the N>1 case is the preferred embodiment over the N=1 embodiment is that in the N=1 case, the manner in which a suspect image is prepared and manipulated has a direct bearing on the likelihood of making a positive identification. Thus, the manner with which an expert makes an identification determination becomes an integral part of that determination. The existence of a multitude of mathematical and statistical approaches to making this determination leave open the possibility that some tests might make positive identifications while others might make negative determinations, inviting further arcane debate about the relative merits of the various identification approaches. The N>1 preferred embodiment of this invention avoids this further gray area by presenting a method where no amount of pre-processing of a signal—other than pre-processing which surreptitiously uses knowledge of the private code signals—can increase the likelihood of "calling the coin flip N times in a row."

The fullest expression of the present system will come when it becomes an industry standard and numerous independent groups set up with their own means or 'in-house' brand of applying embedded identification numbers and in their decipherment. Numerous independent group identification will further enhance the ultimate objectivity of the method, thereby enhancing its appeal as an industry standard.

Use of True Polarity in Creating the Composite Embedded Code Signal

The foregoing discussion made use of the 0 and 1 formalism of binary technology to accomplish its ends. Specifically, the 0's and 1's of the N-bit identification word directly multiplied their corresponding individual embedded code signal to form the composite embedded code signal (step 8, FIG. 2). This approach certainly has its conceptual simplicity, but the multiplication of an embedded code signal by 0 along with the storage of that embedded code contains a kind of inefficiency.

It is preferred to maintain the formalism of the 0 and 1 nature of the N-bit identification word, but to have the 0's of the word induce a subtraction of their corresponding embedded code signal. Thus, in step 8 of FIG. 2, rather than only 'adding' the individual embedded code signals which correspond to a '1' in the N-bit identification word, we will also 'subtract' the individual embedded code signals which correspond to a '0' in the N-bit identification word.

At first glance this seems to add more apparent noise to the final composite signal. But it also increases the energy-wise separation of the 0's from the 1's and thus the 'gain' which is applied in step 10, FIG. 2 can be correspondingly lower.

We can refer to this improvement as the use of true polarity. The main advantage of this improvement can largely be summarized as 'informational efficiency.'

'Perceptual Orthogonality' of the Individual Embedded Code Signals

The foregoing discussion contemplates the use of generally random noise-like signals as the individual embedded code signals. This is perhaps the simplest form of signal to generate. However, there is a form of informational optimization which can be applied to the set of the individual embedded signals, which the applicant describes under the rubric 'perceptual orthogonality.' This term is loosely based on the mathematical concept of the orthogonality of vectors, with the current additional requirement that this orthogonality should maximize the signal energy of the identification information while maintaining it below some perceptibility threshold. Put another way, the embedded code signals need not necessarily be random in nature.

Use and Improvements of the First Embodiment in the Field of Emulsion-Based Photography The foregoing discussion outlined techniques that are applicable to photographic materials. The following section explores the details of this area further and discloses certain improvements which lend themselves to a broad range of applications.

The first area to be discussed involves the pre-application or pre-exposing of a serial number onto traditional photographic products, such as negative film, print paper, transparencies, etc. In general, this is a way to embed a priori unique serial numbers (and by implication, ownership and tracking information) into photographic material. The serial numbers themselves would be a permanent part of the normally exposed picture, as opposed to being relegated to the margins or stamped on the back of a printed photograph, which all require separate locations and separate methods of copying. The 'serial number' as it is called here is generally synonymous with the N-bit identification word, only now we are using a more common industrial terminology.

Figure 2:
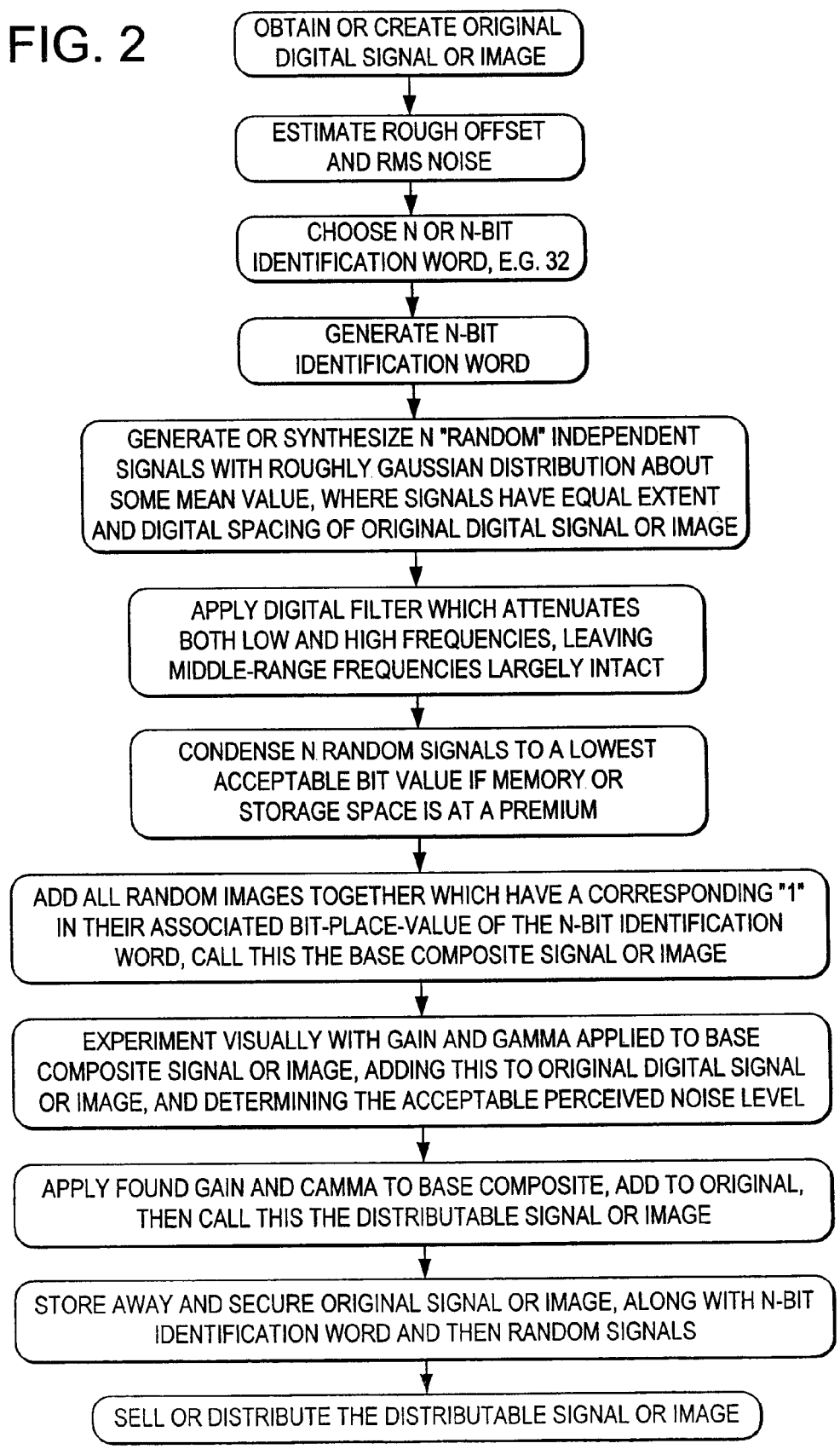
FIG. 2 is a general overview, with detailed description of steps, of the process of embedding an "imperceptible" identification signal onto another signal.

In FIG. 2, step 11, the disclosure calls for the storage of the "original [image]" along with code images. Then in FIG. 3, step 9, it directs that the original be subtracted from the suspect image, thereby leaving the possible identification codes plus whatever noise and corruption has accumulated. Therefore, the previous disclosure made the tacit assumption that there exists an original without the composite embedded signals.

Now in the case of selling print paper and other duplication film products, this will still be the case, i.e., an "original" without the embedded codes will indeed exist and the basic methodology of the first embodiment can be employed. The original film serves perfectly well as an 'unencoded original.'

However, in the case where pre-exposed negative film is used, the composite embedded signal pre-exists on the original film and thus there will never be an "original" separate from the pre-embedded signal. It is this latter case, therefore, which will be examined a bit more closely, along with observations on how to best use the principles discussed above (the former cases adhering to the previously outlined methods).

The clearest point of departure for the case of pre-numbered negative film, i.e. negative film which has had each and every frame pre-exposed with a very faint and unique composite embedded signal, comes at step 9 of FIG. 3 as previously noted. There are certainly other differences as well, but they are mostly logistical in nature, such as how and when to embed the signals on the film, how to store the code numbers and serial number, etc. Obviously the pre-exposing of film would involve a major change to the general mass production process of creating and packaging film.

Figure 4:
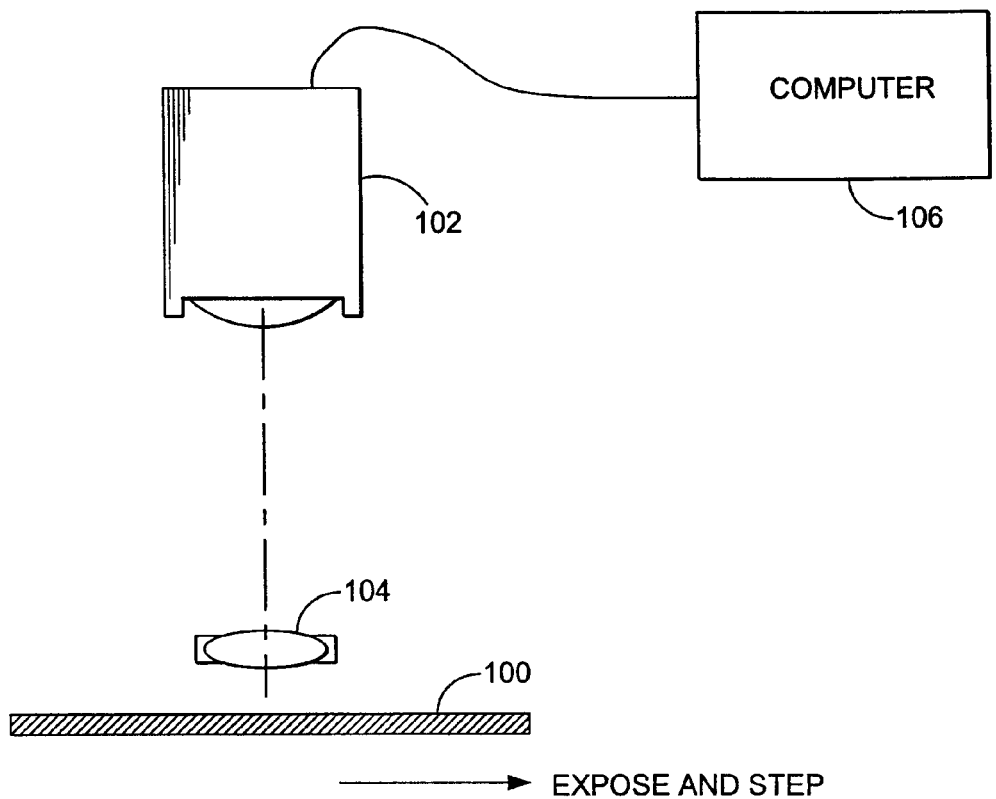
FIG. 4 is a schematic view of an apparatus for pre-exposing film with identification information in accordance with another embodiment of the present invention.

FIG. 4 has a schematic outlining one potential post-hoc mechanism for pre-exposing film. 'Post-hoc' refers to applying a process after the full common manufacturing process of film has already taken place. Eventually, economies of scale may dictate placing this pre-exposing process directly into the chain of manufacturing film. Depicted in FIG. 4 is what is commonly known as a film writing system. The computer, 106, displays the composite signal produced in step 8, FIG. 2, on its phosphor screen. A given frame of film is then exposed by imaging this phosphor screen, where the exposure level is generally very faint, i.e. generally imperceptible. Clearly, the marketplace will set its own demands on how faint this should be, that is, the level of added 'graininess' as practitioners would put it. Each frame of film is sequentially exposed, where in general the composite image displayed on the CRT 102 is changed for each and every frame, thereby giving each frame of film a different serial number. The transfer lens 104 highlights the focal conjugate planes of a film frame and the CRT face.

Getting back to the applying the principles of the foregoing embodiment in the case of pre-exposed negative film . . . . At step 9, FIG. 3, if we were to subtract the "original" with its embedded code, we would obviously be "erasing" the code as well since the code is an integral part of the original. Fortunately, remedies do exist and identifications can still be made. However, it will be a challenge to artisans who refine this embodiment to have the signal to noise ratio of the identification process in the pre-exposed negative case approach the signal to noise ratio of the case where the un-encoded original exists.

A succinct definition of the problem is in order at this point. Given a suspect picture (signal), find the embedded identification code IF a code exists at al. The problem reduces to one of finding the amplitude of each and every individual embedded code signal within the suspect picture, not only within the context of noise and corruption as was previously explained, but now also within the context of the coupling between a captured image and the codes. 'Coupling' here refers to the idea that the captured image "randomly biases" the cross-correlation.

So, bearing in mind this additional item of signal coupling, the identification process now estimates the signal amplitude of each and every individual embedded code signal (as opposed to taking the cross-correlation result of step 12, FIG. 3). If our identification signal exists in the suspect picture, the amplitudes thus found will split into a polarity with positive amplitudes being assigned a '1' and negative amplitudes being assigned a '0'. Our unique identification code manifests itself. If, on the other hand, no such identification code exists or it is someone else's code, then a random gaussian-like distribution of amplitudes is found with a random hash of values.

It remains to provide a few more details on how the amplitudes of the individual embedded codes are found. Again, fortunately, this exact problem has been treated in other technological applications. Besides, throw this problem and a little food into a crowded room of mathematicians and statisticians and surely a half dozen optimized methodologies will pop out after some reasonable period of time. It is a rather cleanly defined problem.

One specific example solution comes from the field of astronomical imaging. Here, it is a mature prior art to subtract out a "thermal noise frame" from a given CCD image of an object. Often, however, it is not precisely known what scaling factor to use in subtracting the thermal frame, and a search for the correct scaling factor is performed. This is precisely the task of this step of the present embodiment.

General practice merely performs a common search algorithm on the scaling factor, where a scaling factor is chosen and a new image is created according to:

NEW IMAGE=ACQUIRED IMAGE−
SCALE*THERMAL IMAGE     (4)

The new image is applied to the fast fourier transform routine and a scale factor is eventually found which minimizes the integrated high frequency content of the new image. This general type of search operation with its minimization of a particular quantity is exceedingly common. The scale factor thus found is the sought-for "amplitude." Refinements which are contemplated but not yet implemented are where the coupling of the higher derivatives of the acquired image and the embedded codes are estimated and removed from the calculated scale factor. In other words, certain bias effects from the coupling mentioned earlier are present and should be eventually accounted for and removed both through theoretical and empirical experimentation.

Use and Improvements in the Detection of Signal or Image Alteration

Apart from the basic need of identifying a signal or image as a whole, there is also a rather ubiquitous need to detect possible alterations to a signal or image. The following section describes how the foregoing embodiment, with certain modifications and improvements, can be used as a powerful tool in this area. The potential scenarios and applications of detecting alterations are innumerable.

To first summarize, assume that we have a given signal or image which has been positively identified using the basic methods outlined above. In other words, we know its N-bit identification word, its individual embedded code signals, and its composite embedded code. We can then fairly simply create a spatial map of the composite code's amplitude within our given signal or image. Furthermore, we can divide this amplitude map by the known composite code's spatial amplitude, giving a normalized map, i.e. a map which should fluctuate about some global mean value. By simple examination of this map, we can visually detect any areas which have been significantly altered wherein the value of the normalized amplitude dips below some statistically set threshold based purely on typical noise and corruption (error).

The details of implementing the creation of the amplitude map have a variety of choices. One is to perform the same procedure which is used to determine the signal amplitude as described above, only now we step and repeat the multiplication of any given area of the signal/image with a gaussian weight function centered about the area we are investigating.

Universal Versus Custom Codes

The disclosure thus far has outlined how each and every source signal has its own unique set of individual embedded code signals. This entails the storage of a significant amount of additional code information above and beyond the original, and many applications may merit some form of economizing.

One such approach to economizing is to have a given set of individual embedded code signals be common to a batch of source materials. For example, one thousand images can all utilize the same basic set of individual embedded code signals. The storage requirements of these codes then become a small fraction of the overall storage requirements of the source material.

Furthermore, some applications can utilize a universal set of individual embedded code signals, i.e., codes which remain the same for all instances of distributed material. This type of requirement would be seen by systems which wish to hide the N-bit identification word itself, yet have standardized equipment be able to read that word. This can be used in systems which make go/no go decisions at point-of-read locations. The potential drawback to this set-up is that the universal codes are more prone to be sleuthed or stolen; therefore they will not be as secure as the apparatus and methodology of the previously disclosed arrangement. Perhaps this is just the difference between 'high security' and 'air-tight security,' a distinction carrying little weight with the bulk of potential applications.

Use in Printing, Paper, Documents, Plastic Coated Identification Cards, and Other Material where Global Embedded Codes can be Imprinted The term 'signal' is often used narrowly to refer to digital data information, audio signals, images, etc. A broader interpretation of 'signal,' and the one more generally intended, includes any form of modulation of any material whatsoever. Thus, the micro-topology of a piece of common paper becomes a 'signal' (e.g. it height as a function of x-y coordinates). The reflective properties of a flat piece of plastic (as a function of space also) becomes a signal. The point is that photographic emulsions, audio signals, and digitized information are not the only types of signals capable of utilizing the principles of the present invention.

As a case in point, a machine very much resembling a braille printing machine can be designed so as to imprint unique 'noise-like' indentations as outlined above. These indentations can be applied with a pressure which is much smaller than is typically applied in creating braille, to the point where the patterns are not noticed by a normal user of the paper. But by following the steps of the present disclosure and applying them via the mechanism of micro-indentations, a unique identification code can be placed onto any given sheet of paper, be it intended for everyday stationary purposes, or be it for important documents, legal tender, or other secured material.

The reading of the identification material in such an embodiment generally proceeds by merely reading the document optically at a variety of angles. This would become an inexpensive method for deducing the micro-topology of the paper surface. Certainly other forms of reading the topology of the paper are possible as well.

In the case of plastic encased material such as identification cards, e.g. driver's licenses, a similar braille-like impressions machine can be utilized to imprint unique identification codes. Subtle layers of photoreactive materials can also be embedded inside the plastic and 'exposed.'

It is clear that wherever a material exists which is capable of being modulated by 'noise-like' signals, that material is an appropriate carrier for unique identification codes and utilization of the principles of the invention. All that remains is the matter of economically applying the identification information and maintaining the signal level below an acceptability threshold which each and every application will define for itself.

Real Time Encoder

While the first class of embodiments most commonly employs a standard microprocessor or computer to perform the encodation of an image or signal, it is possible to utilize a custom encodation device which may be faster than a typical Von Neuman-type processor. Such a system can be utilized with all manner of serial data streams.

Music and videotape recordings are examples of serial data streams—data streams which are often pirated. It would assist enforcement efforts if authorized recordings were encoded with identification data so that pirated knock-offs could be traced to the original from which they were made.

Piracy is but one concern driving the need for the present invention. Another is authentication. Often it is important to confirm that a given set of data is really what it is purported to be (often several years after its generation).

Figure 5:
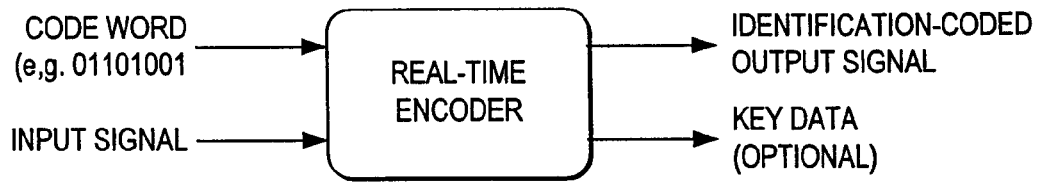
FIG. 5 is a diagram of a "black box" embodiment of the present invention.

To address these and other needs, the system 200 of FIG. 5 can be employed. System 200 can be thought of as an identification coding black box 202. The system 200 receives an input signal (sometimes termed the "master" or "unencoded" signal) and a code word, and produces (generally in real time) an identification-coded output signal. (Usually, the system provides key data for use in later decoding.)

Figure 6:
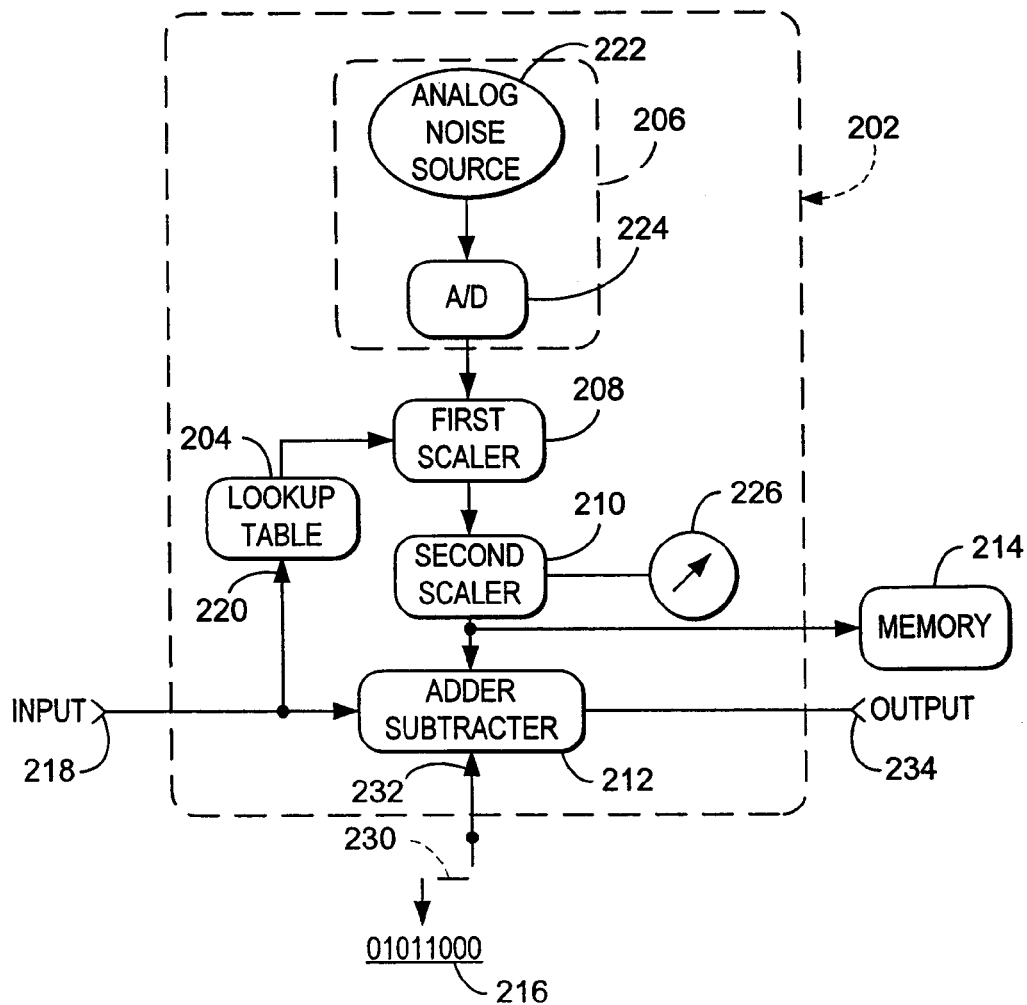
FIG. 6 is a schematic block diagram of the embodiment of FIG. 5.

The contents of the "black box" 202 can take various forms. An exemplary black box system is shown in FIG. 6 and includes a look-up table 204, a digital noise source 206, first and second scalers 208, 210, an adder/subtracter 212, a memory 214, and a register 216.

The input signal (which in the illustrated embodiment is an 8-20 bit data signal provided at a rate of one million samples per second, but which in other embodiments could be an analog signal if appropriate A/D and D/A conversion is provided) is applied from an input 218 to the address input 220 of the look-up table 204. For each input sample (i.e. look-up table address), the table provides a corresponding 8-bit digital output word. This output word is used as a scaling factor that is applied to one input of the first scaler 208.

The first scaler 208 has a second input, to which is applied an 8-bit digital noise signal from source 206. (In the illustrated embodiment, the noise source 206 comprises an analog noise source 222 and an analog-to-digital converter 224 although, again, other implementations can be used.) The noise source in the illustrated embodiment has a zero mean output value, with a full width half maximum (FWHM) of 50-100 digital numbers (e.g. from −75 to +75).

The first scaler 208 multiplies the two 8-bit words at its inputs (scale factor and noise) to produce—for each sample of the system input signal—a 16-bit output word. Since the noise signal has a zero mean value, the output of the first scaler likewise has a zero mean value.

The output of the first scaler 208 is applied to the input of the second scaler 210. The second scaler serves a global scaling function, establishing the absolute magnitude of the identification signal that will ultimately be embedded into the input data signal. The scaling factor is set through a scale control device 226 (which may take a number of forms, from a simple rheostat to a graphically implemented control in a graphical user interface), permitting this factor to be changed in accordance with the requirements of different applications. The second scaler 210 provides on its output line 228 a scaled noise signal. Each sample of this scaled noise signal is successively stored in the memory 214.

(In the illustrated embodiment, the output from the first scaler 208 may range between −1500 and +1500 (decimal), while the output from the second scaler 210 is in the low single digits, (such as between −2 and +2).)

Register 216 stores a multi-bit identification code word. In the illustrated embodiment this code word consists of 8 bits, although larger code words (up to hundreds of bits) are commonly used. These bits are referenced, one at a time, to control how the input signal is modulated with the scaled noise signal.

In particular, a pointer 230 is cycled sequentially through the bit positions of the code word in register 216 to provide a control bit of "0" or "1" to a control input 232 of the adder/subtracter 212. If, for a particular input signal sample, the control bit is a "1", the scaled noise signal sample on line 232 is added to the input signal sample. If the control bit is a "0", the scaled noise signal sample is subtracted from the input signal sample. The output 234 from the adder/subtracter 212 provides the black box's output signal.

The addition or subtraction of the scaled noise signal in accordance with the bits of the code word effects a modulation of the input signal that is generally imperceptible. However, with knowledge of the contents of the memory 214, a user can later decode the encoding, determining the code number used in the original encoding process. (Actually, use of memory 214 is optional, as explained below.)

It will be recognized that the encoded signal can be distributed in well known ways, including converted to printed image form, stored on magnetic media (floppy diskette, analog or DAT tape, etc.), CD-ROM, etc. etc.

Decoding

A variety of techniques can be used to determine the identification code with which a suspect signal has been encoded. Two are discussed below. The first is less preferable than the latter for most applications, but is discussed herein so that the reader may have a fuller context within which to understand the invention.

More particularly, the first decoding method is a difference method, relying on subtraction of corresponding samples of the original signal from the suspect signal to obtain difference samples, which are then examined (typically individually) for deterministic coding indicia (i.e. the stored noise data). This approach may thus be termed a "sample-based, deterministic" decoding technique.

The second decoding method does not make use of the original signal. Nor does it examine particular samples looking for predetermined noise characteristics. Rather, the statistics of the suspect signal (or a portion thereof) are considered in the aggregate and analyzed to discern the presence of identification coding that permeates the entire signal. The reference to permeation means the entire identification code can be discerned from a small fragment of the suspect signal. This latter approach may thus be termed a "holographic, statistical" decoding technique.

Both of these methods begin by registering the suspect signal to match the original. This entails scaling (e.g. in amplitude, duration, color balance, etc.), and sampling (or resampling) to restore the original sample rate. As in the earlier described embodiment, there are a variety of well understood techniques by which the operations associated with this registration function can be performed.

As noted, the first decoding approach proceeds by subtracting the original signal from the registered, suspect signal, leaving a difference signal. The polarity of successive difference signal samples can then be compared with the polarities of the corresponding stored noise signal samples to determine the identification code. That is, if the polarity of the first difference signal sample matches that of the first noise signal sample, then the first bit of the identification code is a "1." (In such case, the polarity of the 9th, 17th, 25th, etc. samples should also all be positive.) If the polarity of the first difference signal sample is opposite that of the corresponding noise signal sample, then the first bit of the identification code is a "0."

By conducting the foregoing analysis with eight successive samples of the difference signal, the sequence of bits that comprise the original code word can be determined. If, as in the preferred embodiment, pointer 230 stepped through the code word one bit at a time, beginning with the first bit, during encoding, then the first 8 samples of the difference signal can be analyzed to uniquely determine the value of the 8-bit code word.

In a noise-free world (speaking here of noise independent of that with which the identification coding is effected), the foregoing analysis would always yield the correct identification code. But a process that is only applicable in a noise-free world is of limited utility indeed.

(Further, accurate identification of signals in noise-free contexts can be handled in a variety of other, simpler ways: e.g. checksums; statistically improbable correspondence between suspect and original signals; etc.)

While noise-induced aberrations in decoding can be dealt with—to some degree—by analyzing large portions of the signal, such aberrations still place a practical ceiling on the confidence of the process. Further, the villain that must be confronted is not always as benign as random noise. Rather, it increasingly takes the form of human-caused corruption, distortion, manipulation, etc. In such cases, the desired degree of identification confidence can only be achieved by other approaches.

The presently preferred approach (the "holographic, statistical" decoding technique) relies on recombining the suspect signal with certain noise data (typically the data stored in memory 214), and analyzing the entropy of the resulting signal. "Entropy" need not be understood in its most strict mathematical definition, it being merely the most concise word to describe randomness (noise, smoothness, snowiness, etc.).

Most serial data signals are not random. That is, one sample usually correlates—to some degree—with the adjacent samples. Noise, in contrast, typically is random. If a random signal (e.g. noise) is added to (or subtracted from) a non-random signal, the entropy of the resulting signal generally increases. That is, the resulting signal has more random variations than the original signal. This is the case with the encoded output signal produced by the present encoding process; it has more entropy than the original, unencoded signal.

If, in contrast, the addition of a random signal to (or subtraction from) a non-random signal reduces entropy, then something unusual is happening. It is this anomaly that the preferred decoding process uses to detect embedded identification coding.

To fully understand this entropy-based decoding method, it is first helpful to highlight a characteristic of the original encoding process: the similar treatment of every eighth sample.

In the encoding process discussed above, the pointer 230 increments through the code word, one bit for each successive sample of the input signal. If the code word is eight bits in length, then the pointer returns to the same bit position in the code word every eighth signal sample. If this bit is a "1", noise is added to the input signal; if this bit is a "0", noise is subtracted from the input signal. Due to the cyclic progression of the pointer 230, every eighth sample of an encoded signal thus shares a characteristic: they are all either augmented by the corresponding noise data (which may be negative), or they are all diminished, depending on whether the bit of the code word then being addressed by pointer 230 is a "1" or a "0".

To exploit this characteristic, the entropy-based decoding process treats every eighth sample of the suspect signal in like fashion. In particular, the process begins by adding to the 1st, 9th, 17th, 25th, etc. samples of the suspect signal the corresponding scaled noise signal values stored in the memory 214 (i.e. those stored in the 1st, 9th, 17th, 25th, etc., memory locations, respectively). The entropy of the resulting signal (i.e. the suspect signal with every 8th sample modified) is then computed.

(Computation of a signal's entropy or randomness is well understood by artisans in this field. One generally accepted technique is to take the derivative of the signal at each sample point, square these values, and then sum over the entire signal. However, a variety of other well known techniques can alternatively be used.)

The foregoing step is then repeated, this time subtracting the stored noise values from the 1st, 9th, 17th, 25 etc. suspect signal samples.

One of these two operations will undo the encoding process and reduce the resulting signal's entropy; the other will aggravate it. If adding the noise data in memory 214 to the suspect signal reduces its entropy, then this data must earlier have been subtracted from the original signal. This indicates that pointer 230 was pointing to a "0" bit when these samples were encoded. (A "0" at the control input of adder/subtracter 212 caused it to subtract the scaled noise from the input signal.)

Conversely, if subtracting the noise data from every eighth sample of the suspect signal reduces its entropy, then the encoding process must have earlier added this noise. This indicates that pointer 230 was pointing to a "1" bit when samples 1, 9, 17, 25, etc., were encoded.

By noting whether entropy decreases by (a) adding or (b) subtracting the stored noise data to/from the suspect signal, it can be determined that the first bit of the code word is (a) a "0", or (b) a "1".

The foregoing operations are then conducted for the group of spaced samples of the suspect signal beginning with the second sample (i.e. 2, 10, 18, 26 . . . ). The entropy of the resulting signals indicate whether the second bit of the code word is a "0" or a "1". Likewise with the following 6 groups of spaced samples in the suspect signal, until all 8 bits of the code word have been discerned.

It will be appreciated that the foregoing approach is not sensitive to corruption mechanisms that alter the values of individual samples; instead, the process considers the entropy of the signal as a whole, yielding a high degree of confidence in the results. Further, even small excerpts of the signal can be analyzed in this manner, permitting piracy of even small details of an original work to be detected. The results are thus statistically robust, both in the face of natural and human corruption of the suspect signal.

It will further be appreciated that the use of an N-bit code word in this real time embodiment provides benefits analogous to those discussed above in connection with the batch encoding system. (Indeed, the present embodiment may be conceptualized as making use of N different noise signals, just as in the batch encoding system. The first noise signal is a signal having the same extent as the input signal, and comprising the scaled noise signal at the 1st, 9th, 17th, 25th, etc., samples (assuming N=8), with zeroes at the intervening samples. The second noise signal is a similar one comprising the scaled noise signal at the 2d, 10th, 18th, 26th, etc., samples, with zeroes at the intervening samples. Etc. These signals are all combined to provide a composite noise signal.) One of the important advantages inherent in such a system is the high degree of statistical confidence (confidence which doubles with each successive bit of the identification code) that a match is really a match. The system does not rely on subjective evaluation of a suspect signal for a single, deterministic embedded code signal.

Illustrative Variations

From the foregoing description, it will be recognized that numerous modifications can be made to the illustrated systems without changing the fundamental principles. A few of these variations are described below.

The above-described decoding process tries both adding and subtracting stored noise data to/from the suspect signal in order to find which operation reduces entropy. In other embodiments, only one of these operations needs to be conducted. For example, in one alternative decoding process the stored noise data corresponding to every eighth sample of the suspect signal is only added to said samples. If the entropy of the resulting signal is thereby increased, then the corresponding bit of the code word is a "1" (i.e. this noise was added earlier, during the encoding process, so adding it again only compounds the signal's randomness). If the entropy of the resulting signal is thereby decreased, then the corresponding bit of the code word is a "0". A further test of entropy if the stored noise samples are subtracted is not required.

The statistical reliability of the identification process (coding and decoding) can be designed to exceed virtually any confidence threshold (e.g. 99.9%, 99.99%, 99.999%, etc. confidence) by appropriate selection of the global scaling factors, etc. Additional confidence in any given application (unnecessary in most applications) can be achieved by rechecking the decoding process.

One way to recheck the decoding process is to remove the stored noise data from the suspect signal in accordance with the bits of the discerned code word, yielding a "restored" signal (e.g. if the first bit of the code word is found to be "1," then the noise samples stored in the 1st, 9th, 17th, etc. locations of the memory 214 are subtracted from the corresponding samples of the suspect signal). The entropy of the restored signal is measured and used as a baseline in further measurements. Next, the process is repeated, this time removing the stored noise data from the suspect signal in accordance with a modified code word. The modified code word is the same as the discerned code word, except 1 bit is toggled (e.g. the first). The entropy of the resulting signal is determined, and compared with the baseline. If the toggling of the bit in the discerned code word resulted in increased entropy, then the accuracy of that bit of the discerned code word is confirmed. The process repeats, each time with a different bit of the discerned code word toggled, until all bits of the code word have been so checked. Each change should result in an increase in entropy compared to the baseline value.

The data stored in memory 214 is subject to a variety of alternatives. In the foregoing discussion, memory 214 contains the scaled noise data. In other embodiments, the unscaled noise data can be stored instead.

In still other embodiments, it can be desirable to store at least part of the input signal itself in memory 214. For example, the memory can allocate 8 signed bits to the noise sample, and 16 bits to store the most significant bits of an 18- or 20-bit audio signal sample. This has several benefits. One is that it simplifies registration of a "suspect" signal. Another is that, in the case of encoding an input signal which was already encoded, the data in memory 214 can be used to discern which of the encoding processes was performed first. That is, from the input signal data in memory 214 (albeit incomplete), it is generally possible to determine with which of two code words it has been encoded.

Yet another alternative for memory 214 is that is can be omitted altogether.

One way this can be achieved is to use a deterministic noise source in the encoding process, such as an algorithmic noise generator seeded with a known key number. The same deterministic noise source, seeded with the same key number, can be used in the decoding process. In such an arrangement, only the key number needs be stored for later use in decoding, instead of the large data set usually stored in memory 214.

Alternatively, if the noise signal added during encoding does not have a zero mean value, and the length N of the code word is known to the decoder, then a universal decoding process can be implemented. This process uses the same entropy test as the foregoing procedures, but cycles through possible code words, adding/subtracting a small dummy noise value (e.g. less than the expected mean noise value) to every Nth sample of the suspect signal, in accordance with the bits of the code word being tested, until a reduction in entropy is noted. Such an approach is not favored for most applications, however, because it offers less security than the other embodiments (e.g. it is subject to cracking by brute force).

Figure 7:
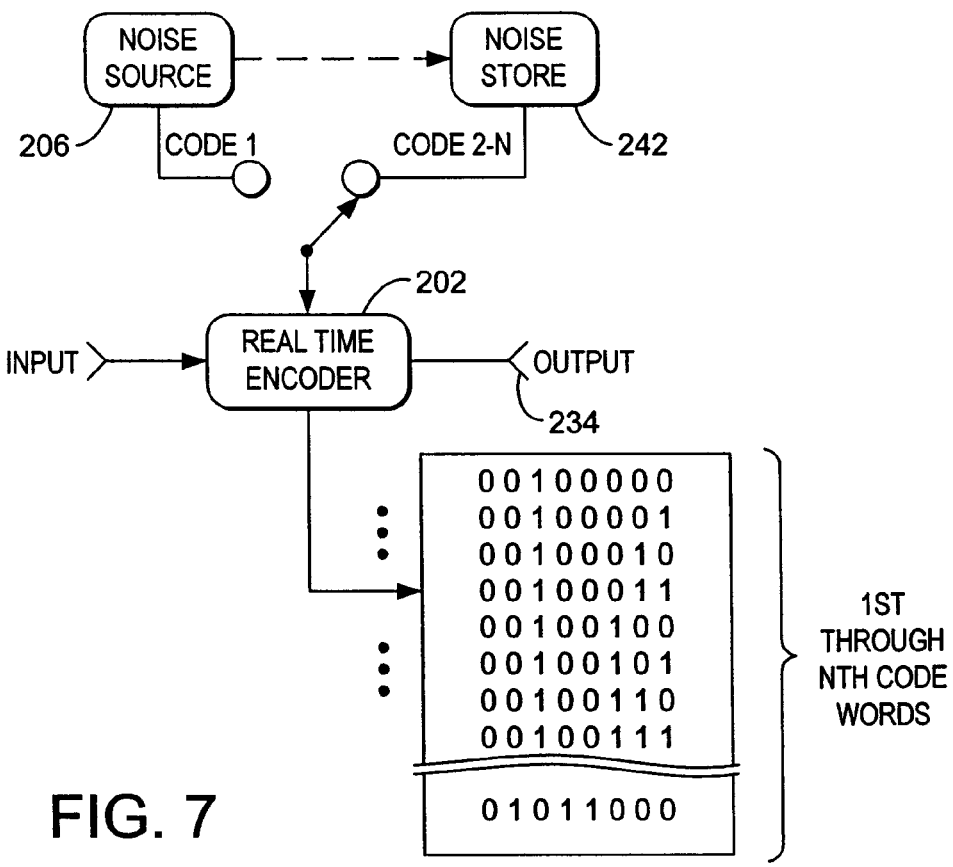
FIG. 7 shows a variant of the FIG. 6 embodiment adapted to encode successive sets of input data with different code words but with the same noise data.

Many applications are well served by the embodiment illustrated in FIG. 7, in which different code words are used to produce several differently encoded versions of an input signal, each making use of the same noise data. More particularly, the embodiment 240 of FIG. 7 includes a noise store 242 into which noise from source 206 is written during the identification-coding of the input signal with a first code word. (The noise source of FIG. 7 is shown outside of the real time encoder 202 for convenience of illustration.) Thereafter, additional identification-coded versions of the input signal can be produced by reading the stored noise data from the store and using it in conjunction with second through Nth code words to encode the signal. (While binary-sequential code words are illustrated in FIG. 7, in other embodiments arbitrary sequences of code words can be employed.) With such an arrangement, a great number of differently-encoded signals can be produced, without requiring a proportionally-sized long term noise memory. Instead, a fixed amount of noise data is stored, whether encoding an original once or a thousand times.

(If desired, several differently-coded output signals can be produced at the same time, rather than seriatim. One such implementation includes a plurality of adder/subtracter circuits 212, each driven with the same input signal and with the same scaled noise signal, but with different code words. Each, then, produces a differently encoded output signal.)

In applications having a great number of differently-encoded versions of the same original, it will be recognized that the decoding process need not always discern every bit of the code word. Sometimes, for example, the application may require identifying only a group of codes to which the suspect signal belongs. (E.g., high order bits of the code word might indicate an organization to which several differently coded versions of the same source material were provided, with low-order bits identifying specific copies. To identify the organization with which a suspect signal is associated, it may not be necessary to examine the low order bits, since the organization can be identified by the high order bits alone.) If the identification requirements can be met by discerning a subset of the code word bits in the suspect signal, the decoding process can be shortened.

Figure 8:
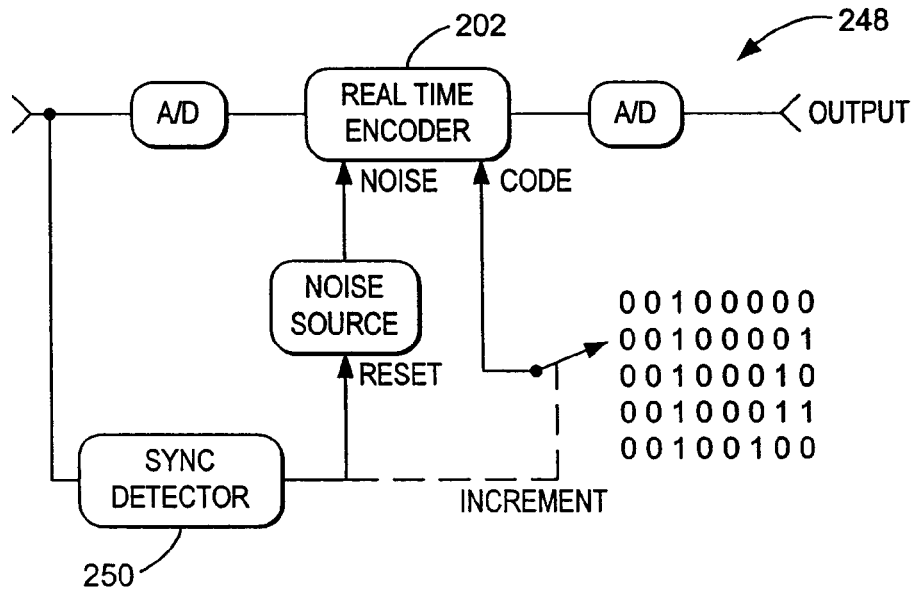
FIG. 8 shows a variant of the FIG. 6 embodiment adapted to encode each frame of a videotaped production with a unique code number.

Some applications may be best served by restarting the encoding process—sometimes with a different code word—several times within an integral work. Consider, as an example, videotaped productions (e.g. television programming). Each frame of a videotaped production can be identification-coded with a unique code number, processed in real-time with an arrangement 248 like that shown in FIG. 8. Each time a vertical retrace is detected by sync detector 250, the noise source 206 resets (e.g. to repeat the sequence just produced) and an identification code increments to the next value. Each frame of the videotape is thereby uniquely identification-coded. Typically, the encoded signal is stored on a videotape for long term storage (although other storage media, including laser disks, can be used).

Returning to the encoding apparatus, the look-up table 204 in the illustrated embodiment exploits the fact that high amplitude samples of the input data signal can tolerate (without objectionable degradation of the output signal) a higher level of encoded identification coding than can low amplitude input samples. Thus, for example, input data samples having decimal values of 0, 1 or 2 may be correspond (in the look-up table 204) to scale factors of unity (or even zero), whereas input data samples having values in excess of 200 may correspond to scale factors of 15. Generally speaking, the scale factors and the input sample values correspond by a square root relation. That is, a four-fold increase in a value of the sampled input signal corresponds to approximately a two-fold increase in a value of the scaling factor associated therewith.

(The parenthetical reference to zero as a scaling factor alludes to cases, e.g., in which the source signal is temporally or spatially devoid of information content. In an image, for example, a region characterized by several contiguous sample values of zero may correspond to a jet black region of the frame. A scaling value of zero may be appropriate here since there is essentially no image data to be pirated.)

Continuing with the encoding process, those skilled in the art will recognized the potential for "rail errors" in the illustrated embodiment. For example, if the input signal consists of 8-bit samples, and the samples span the entire range from 0 to 255 (decimal), then the addition or subtraction of scaled noise to/from the input signal may produce output signals that cannot be represented by 8 bits (e.g. −2, or 257). A number of well-understood techniques exist to rectify this situation, some of them proactive and some of them reactive. (Among these known techniques are: specifying that the input signal shall not have samples in the range of 0-4 or 251-255, thereby safely permitting modulation by the noise signal; or including provision for detecting and adaptively modifying input signal samples that would otherwise cause rail errors.)

While the illustrated embodiment describes stepping through the code word sequentially, one bit at a time, to control modulation of successive bits of the input signal, it will be appreciated that the bits of the code word can be used other than sequentially for this purpose. Indeed, bits of the code word can be selected in accordance with any predetermined algorithm.

The dynamic scaling of the noise signal based on the instantaneous value of the input signal is an optimization that can be omitted in many embodiments. That is, the look-up table 204 and the first scaler 208 can be omitted entirely, and the signal from the digital noise source 206 applied directly (or through the second, global scaler 210) to the adder/subtracter 212.

It will be further recognized that the use of a zero-mean noise source simplifies the illustrated embodiment, but is not necessary to the invention. A noise signal with another mean value can readily be used, and D.C. compensation (if needed) can be effected elsewhere in the system.

The use of a noise source 206 is also optional. A variety of other signal sources can be used, depending on application-dependent constraints (e.g. the threshold at which the encoded identification signal becomes perceptible). In many instances, the level of the embedded identification signal is low enough that the identification signal needn't have a random aspect; it is imperceptible regardless of its nature. A pseudo random source 206, however, is usually desired because it provides the greatest identification code signal S/N ratio (a somewhat awkward term in this instance) for a level of imperceptibility of the embedded identification signal.

It will be recognized that identification coding need not occur after a signal has been reduced to stored form as data (i.e. "fixed in tangible form," in the words of the U.S. Copyright Act). Consider, for example, the case of popular musicians whose performances are often recorded illicitly. By identification coding the audio before it drives concert hall speakers, unauthorized recordings of the concert can be traced to a particular place and time. Likewise, live audio sources such as 911 emergency calls can be encoded prior to recording so as to facilitate their later authentication.

While the black box embodiment has been described as a stand alone unit, it will be recognized that it can be integrated into a number of different tools/instruments as a component.

One is a scanner, which can embed identification codes in the scanned output data. (The codes can simply serve to memorialize that the data was generated by a particular scanner). Another is in creativity software, such as popular drawing/graphics/animation/paint programs offered by Adobe, Macromedia, Corel, and the like.

Finally, while the real-time encoder 202 has been illustrated with reference to a particular hardware implementation, it will be recognized that a variety of other implementations can alternatively be employed. Some utilize other hardware configurations. Others make use of software routines for some or all of the illustrated functional blocks. (The software routines can be executed on any number of different general purpose programmable computers, such as 80×86 PC-compatible computers, RISC-based workstations, etc.)

Types of Noise, Quasi-Noise, and Optimized-Noise

Heretofore this disclosure postulated Gaussian noise, "white noise," and noise generated directly from application instrumentation as a few of the many examples of the kind of carrier signal appropriate to carry a single bit of information throughout an image or signal. It is possible to be even more proactive in "designing" characteristics of noise in order to achieve certain goals. The "design" of using Gaussian or instrumental noise was aimed somewhat toward "absolute" security. This section of the disclosure takes a look at other considerations for the design of the noise signals which may be considered the ultimate carriers of the identification information.

For some applications it might be advantageous to design the noise carrier signal (e.g. the Nth embedded code signal in the first embodiment; the scaled noise data in the second embodiment), so as to provide more absolute signal strength to the identification signal relative to the perceptibility of that signal. One example is the following. It is recognized that a true Gaussian noise signal has the value '0' occur most frequently, followed by 1 and −1 at equal probabilities to each other but lower than '0', 2 and −2 next, and so on. Clearly, the value zero carries no information as it is used in the service of this invention. Thus, one simple adjustment, or design, would be that any time a zero occurs in the generation of the embedded code signal, a new process takes over, whereby the value is converted "randomly" to either a 1 or a −1. In logical terms, a decision would be made: if '0', then random (1,−1). The histogram of such a process would appear as a Gaussian/Poissonian type distribution, except that the 0 bin would be empty and the 1 and −1 bin would be increased by half the usual histogram value of the 0 bin.

In this case, identification signal energy would always be applied at all parts of the signal. A few of the trade-offs include: there is a (probably negligible) lowering of security of the codes in that a "deterministic component" is a part of generating the noise signal. The reason this might be completely negligible is that we still wind up with a coin flip type situation on randomly choosing the 1 or the −1. Another trade-off is that this type of designed noise will have a higher threshold of perceptibility, and will only be applicable to applications where the least significant bit of a data stream or image is already negligible relative to the commercial value of the material, i.e. if the least significant bit were stripped from the signal (for all signal samples), no one would know the difference and the value of the material would not suffer. This blocking of the zero value in the example above is but one of many ways to "optimize" the noise properties of the signal carrier, as anyone in the art can realize. We refer to this also as "quasi-noise" in the sense that natural noise can be transformed in a pre-determined way into signals which for all intents and purposes will read as noise. Also, cryptographic methods and algorithms can easily, and often by definition, create signals which are perceived as completely random. Thus the word "noise" can have different connotations, primarily between that as defined subjectively by an observer or listener, and that defined mathematically. The difference of the latter is that mathematical noise has different properties of security and the simplicity with which it can either be "sleuthed" or the simplicity with which instruments can "automatically recognize" the existence of this noise.

"Universal" Embedded Codes

The bulk of this disclosure teaches that for absolute security, the noise-like embedded code signals which carry the bits of information of the identification signal should be unique to each and every encoded signal, or, slightly less restrictive, that embedded code signals should be generated sparingly, such as using the same embedded codes for a batch of 1000 pieces of film, for example. Be this as it may, there is a whole other approach to this issue wherein the use of what we will call "universal" embedded code signals can open up large new applications for this technology. The economics of these uses would be such that the de facto lowered security of these universal codes (e.g. they would be analyzable by time honored cryptographic decoding methods, and thus potentially thwarted or reversed) would be economically negligible relative to the economic gains that the intended uses would provide. Piracy and illegitimate uses would become merely a predictable "cost" and a source of uncollected revenue only; a simple line item in an economic analysis of the whole. A good analogy of this is in the cable industry and the scrambling of video signals. Everybody seems to know that crafty, skilled technical individuals, who may be generally law abiding citizens, can climb a ladder and flip a few wires in their cable junction box in order to get all the pay channels for free. The cable industry knows this and takes active measures to stop it and prosecute those caught, but the "lost revenue" derived from this practice remains prevalent but almost negligible as a percentage of profits gained from the scrambling system as a whole. The scrambling system as a whole is an economic success despite its lack of "absolute security."

The same holds true for applications of this technology wherein, for the price of lowering security by some amount, large economic opportunity presents itself. This section first describes what is meant by universal codes, then moves on to some of the interesting uses to which these codes can be applied.

Universal embedded codes generally refer to the idea that knowledge of the exact codes can be distributed. The embedded codes won't be put into a dark safe never to be touched until litigation arises (as alluded to in other parts of this disclosure), but instead will be distributed to various locations where on-the-spot analysis can take place. Generally this distribution will still take place within a security controlled environment, meaning that steps will be taken to limit the knowledge of the codes to those with a need to know. Instrumentation which attempts to automatically detect copyrighted material is a non-human example of "something" with a need to know the codes.

There are many ways to implement the idea of universal codes, each with their own merits regarding any given application. For the purposes of teaching this art, we separate these approaches into three broad categories: universal codes based on libraries, universal codes based on deterministic formula, and universal codes based on pre-defined industry standard patterns. A rough rule of thumb is that the first is more secure than the latter two, but that the latter two are possibly more economical to implement than the first.

Universal Codes: 1) Libraries of Universal Codes

The use of libraries of universal codes simply means that the techniques of this invention are employed as described, except for the fact that only a limited set of the individual embedded code signals are generated and that any given encoded material will make use of some sub-set of this limited "universal set." An example is in order here. A photographic print paper manufacturer may wish to pre-expose every piece of 8 by 10 inch print paper which they sell with a unique identification code. They also wish to sell identification code recognition software to their large customers, service bureaus, stock agencies, and individual photographers, so that all these people can not only verify that their own material is correctly marked, but so that they can also determine if third party material which they are about to acquire has been identified by this technology as being copyrighted. This latter information will help them verify copyright holders and avoid litigation, among many other benefits. In order to "economically" institute this plan, they realize that generating unique individual embedded codes for each and every piece of print paper would generate Terabytes of independent information, which would need storing and to which recognition software would need access. Instead, they decide to embed their print paper with 16 bit identification codes derived from a set of only 50 independent "universal" embedded code signals. The details of how this is done are in the next paragraph, but the point is that now their recognition software only needs to contain a limited set of embedded codes in their library of codes, typically on the order of 1 Megabyte to 10 Megabytes of information for 50×16 individual embedded codes splayed out onto an 8×10 photographic print (allowing for digital compression). The reason for picking 50 instead of just 16 is one of a little more added security, where if it were the same 16 embedded codes for all photographic sheets, not only would the serial number capability be limited to 2 to the 16th power, but lesser and lesser sophisticated pirates could crack the codes and remove them using software tools.

There are many different ways to implement this scheme, where the following is but one exemplary method. It is determined by the wisdom of company management that a 300 pixels per inch criteria for the embedded code signals is sufficient resolution for most applications. This means that a composite embedded code image will contain 3000 pixels by 2400 pixels to be exposed at a very low level onto each 8×10 sheet. This gives 7.2 million pixels. Using our staggered coding system such as described in the black box implementation of FIGS. 5 and 6, each individual embedded code signal will contain only 7.2 million divided by 16, or approximately 450K true information carrying pixels, i.e. every 16th pixel along a given raster line. These values will typically be in the range of 2 to −2 in digital numbers, or adequately described by a signed 3 bit number. The raw information content of an embedded code is then approximately ⅜th's bytes times 450K or about 170 Kilobytes. Digital compression can reduce this further. All of these decisions are subject to standard engineering optimization principles as defined by any given application at hand, as is well known in the art. Thus we find that 50 of these independent embedded codes will amount to a few Megabytes. This is quite reasonable level to distribute as a "library" of universal codes within the recognition software. Advanced standard encryption devices could be employed to mask the exact nature of these codes if one were concerned that would-be pirates would buy the recognition software merely to reverse engineer the universal embedded codes. The recognition software could simply unencrypt the codes prior to applying the recognition techniques taught in this disclosure.

The recognition software itself would certainly have a variety of features, but the core task it would perform is determining if there is some universal copyright code within a given image. The key questions become WHICH 16 of the total 50 universal codes it might contain, if any, and if there are 16 found, what are their bit values. The key variables in determining the answers to these questions are: registration, rotation, magnification (scale), and extent. In the most general case with no helpful hints whatsoever, all variables must be independently varied across all mutual combinations, and each of the 50 universal codes must then be checked by adding and subtracting to see if an entropy decrease occurs. Strictly speaking, this is an enormous job, but many helpful hints will be found which make the job much simpler, such as having an original image to compare to the suspected copy, or knowing the general orientation and extent of the image relative to an 8×10 print paper, which then through simple registration techniques can determine all of the variables to some acceptable degree. Then it merely requires cycling through the 50 universal codes to find any decrease in entropy. If one does, then 15 others should as well. A protocol needs to be set up whereby a given order of the 50 translates into a sequence of most significant bit through least significant bit of the ID code word. Thus if we find that universal code number "4" is present, and we find its bit value to be "0", and that universal codes "1" through "3" are definitely not present, then our most significant bit of our N-bit ID code number is a "0". Likewise, we find that the next lowest universal code present is number "7" and it turns out to be a "1", then our next most significant bit is a "1". Done properly, this system can cleanly trace back to the copyright owner so long as they registered their photographic paper stock serial number with some registry or with the manufacturer of the paper itself. That is, we look up in the registry that a paper using universal embedded codes 4, 7, 11, 12, 15, 19, 21, 26, 27, 28, 34, 35, 37, 38, 40, and 48, and having the embedded code 0110 0101 0111 0100 belongs to Leonardo de Boticelli, an unknown wildlife photographer and glacier cinematographer whose address is in Northern Canada. We know this because the dutifully registered his film and paper stock, a few minutes of work when he bought the stock, which he plopped into the "no postage necessary" envelope that the manufacturing company kindly provided to make the process ridiculously simple. Somebody owes Leonardo a royalty check it would appear, and certainly the registry has automated this royalty payment process as part of its services.

One final point is that truly sophisticated pirates and others with illicit intentions can indeed employ a variety of cryptographic and not so cryptographic methods to crack these universal codes, sell them, and make software and hardware tools which can assist in the removing or distorting of codes. We shall not teach these methods as part of this disclosure, however. In any event, this is one of the prices which must be paid for the ease of universal codes and the applications they open up.

Universal Codes: 2) Universal Codes Based on Deterministic Formulas

The libraries of universal codes require the storage and transmittal of Megabytes of independent, generally random data as the keys with which to unlock the existence and identity of signals and imagery that have been marked with universal codes. Alternatively, various deterministic formulas can be used which "generate" what appear to be random data/image frames, thereby obviating the need to store all of these codes in memory and interrogate each and of the "50" universal codes. Deterministic formulas can also assist in speeding up the process of determining the ID code once one is known to exist in a given signal or image. On the other hand, deterministic formulas lend themselves to sleuthing by less sophisticated pirates. And once sleuthed, they lend themselves to easier communication, such as posting on the Internet to a hundred newsgroups. There may well be many applications which do not care about sleuthing and publishing, and deterministic formulas for generating the individual universal embedded codes might be just the ticket.

Universal Codes: 3) "Simple" Universal Codes

This category is a bit of a hybrid of the first two, and is most directed at truly large scale implementations of the principles of this technology. The applications employing this class are of the type where staunch security is much less important than low cost, large scale implementation and the vastly larger economic benefits that this enables. One exemplary application is placement of identification recognition units directly within modestly priced home audio and video instrumentation (such as a TV). Such recognition units would typically monitor audio and/or video looking for these copyright identification codes, and thence triggering simple decisions based on the findings, such as disabling or enabling recording capabilities, or incrementing program specific billing meters which are transmitted back to a central audio/video service provider and placed onto monthly invoices. Likewise, it can be foreseen that "black boxes" in bars and other public places can monitor (listen with a microphone) for copyrighted materials and generate detailed reports, for use by ASCAP, BMI, and the like.

A core principle of simple universal codes is that some basic industry standard "noiselike" and seamlessly repetitive patterns are injected into signals, images, and image sequences so that inexpensive recognition units can either A) determine the mere existence of a copyright "flag", and B) additionally to A, determine precise identification information which can facilitate more complex decision making and actions.

In order to implement this particular embodiment of the present invention, the basic principles of generating the individual embedded noise signals need to be simplified in order to accommodate inexpensive recognition signal processing circuitry, while maintaining the properties of effective randomness and holographic permeation. With large scale industry adoption of these simple codes, the codes themselves would border on public domain information (much as cable scrambling boxes are almost de facto public domain), leaving the door open for determined pirates to develop black market countermeasures, but this situation would be quite analogous to the scrambling of cable video and the objective economic analysis of such illegal activity.

One prior art known to the applicant in this general area of pro-active copyright detection is the Serial Copy Management System adopted by many firms in the audio industry. To the best of applicant's knowledge, this system employs a non-audio "flag" signal which is not part of the audio data stream, but which is nevertheless grafted onto the audio stream and can indicate whether the associated audio data should or should not be duplicated. One problem with this system is that it is restricted to media and instrumentation which can support this extra "flag" signal. Another deficiency is that the flagging system carries no identity information which would be useful in making more complex decisions. Yet another difficulty is that high quality audio sampling of an analog signal can come arbitrarily close to making a perfect digital copy of some digital master and there seems to be no provision for inhibiting this possibility.

Figure 9A:
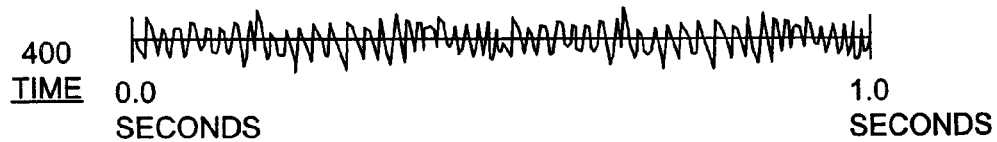
FIGS. 9A-9C are representations of an industry standard noise second that can be used in one embodiment of the present invention.
Figure 9B:
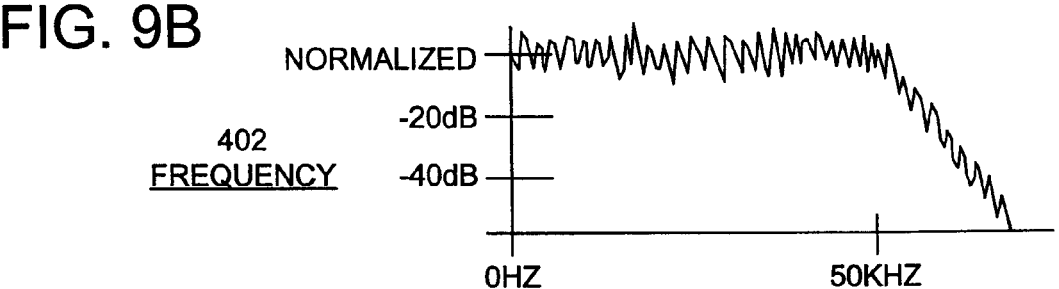
Figure 9C:
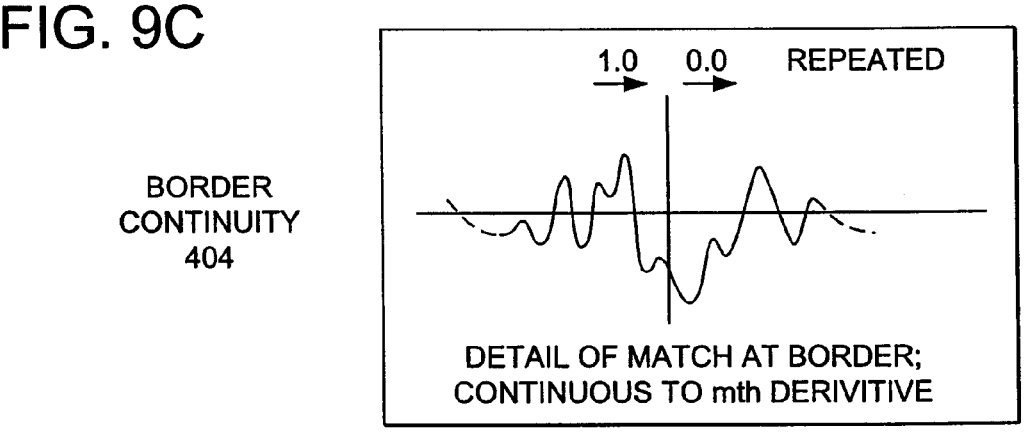

The principles of this invention can be brought to bear on these and other problems, in audio applications, video, and all of the other applications previously discussed. An exemplary application of simple universal codes is the following. A single industry standard "1.000000 second of noise" would be defined as the most basic indicator of the presence or absence of the copyright marking of any given audio signal. FIG. 9 has an example of what the waveform of an industry standard noise second might look like, both in the time domain 400 and the frequency domain 402. It is by definition a continuous function and would adapt to any combination of sampling rates and bit quanitizations. It has a normalized amplitude and can be scaled arbitrarily to any digital signal amplitude. The signal level and the first M'th derivatives of the signal are continuous at the two boundaries 404 (FIG. 9C), such that when it is repeated, the "break" in the signal would not be visible (as a waveform) or audible when played through a high end audio system. The choice of 1 second is arbitrary in this example, where the precise length of the interval will be derived from considerations such as audibility, quasi-white noise status, seamless repeatability, simplicity of recognition processing, and speed with which a copyright marking determination can be made. The injection of this repeated noise signal onto a signal or image (again, at levels below human perception) would indicate the presence of copyright material. This is essentially a one bit identification code, and the embedding of further identification information will be discussed later on in this section. The use of this identification technique can extend far beyond the low cost home implementations discussed here, where studios could use the technique, and monitoring stations could be set up which literally monitor hundreds of channels of information simultaneously, searching for marked data streams, and furthermore searching for the associated identity codes which could be tied in with billing networks and royalty tracking systems.

This basic, standardized noise signature is seamlessly repeated over and over again and added to audio signals which are to be marked with the base copyright identification. Part of the reason for the word "simple" is seen here: clearly pirates will know about this industry standard signal, but their illicit uses derived from this knowledge, such as erasure or corruption, will be economically minuscule relative to the economic value of the overall technique to the mass market. For most high end audio this signal will be some 80 to 100 dB down from full scale, or even much further; each situation can choose its own levels though certainly there will be recommendations. The amplitude of the signal can be modulated according to the audio signal levels to which the noise signature is being applied, i.e. the amplitude can increase significantly when a drum beats, but not so dramatically as to become audible or objectionable. These measures merely assist the recognition circuitry to be described.

Recognition of the presence of this noise signature by low cost instrumentation can be effected in a variety of ways. One rests on basic modifications to the simple principles of audio signal power metering. Software recognition programs can also be written, and more sophisticated mathematical detection algorithms can be applied to audio in order to make higher confidence detection identifications. In such embodiments, detection of the copyright noise signature involves comparing the time averaged power level of an audio signal with the time averaged power level of that same audio signal which has had the noise signature subtracted from it. If the audio signal with the noise signature subtracted has a lower power level that the unchanged audio signal, then the copyright signature is present and some status flag to that effect needs to be set. The main engineering subtleties involved in making this comparison include: dealing with audio speed playback discrepancies (e.g. an instrument might be 0.5% "slow" relative to exactly one second intervals); and, dealing with the unknown phase of the one second noise signature within any given audio (basically, its "phase" can be anywhere from 0 to 1 seconds). Another subtlety, not so central as the above two but which nonetheless should be addressed, is that the recognition circuits should not subtract a higher amplitude of the noise signature than was originally embedded onto the audio signal. Fortunately this can be accomplished by merely subtracting only a small amplitude of the noise signal, and if the power level goes down, this is an indication of "heading toward a trough" in the power levels. Yet another related subtlety is that the power level changes will be very small relative to the overall power levels, and calculations generally will need to be done with appropriate bit precision, e.g. 32 bit value operations and accumulations on 16-20 bit audio in the calculations of time averaged power levels.

Figure 10:
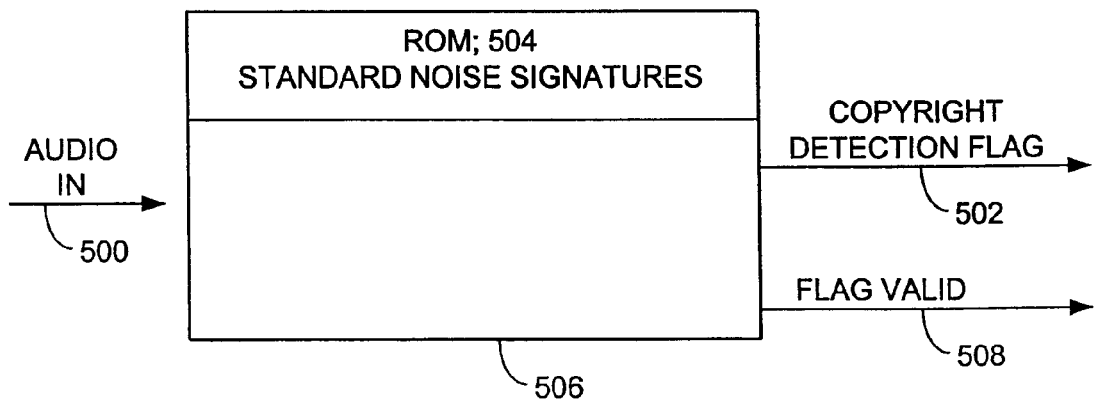
FIG. 10 shows an integrated circuit used in detecting standard noise codes.

Clearly, designing and packaging this power level comparison processing circuitry for low cost applications is an engineering optimization task. One trade-off will be the accuracy of making an identification relative to the "short-cuts" which can be made to the circuitry in order to lower its cost and complexity. A preferred embodiment for the placement of this recognition circuitry inside of instrumentation is through a single programmable integrated circuit which is custom made for the task. FIG. 10 shows one such integrated circuit 506. Here the audio signal comes in, 500, either as a digital signal or as an analog signal to be digitized inside the IC 500, and the output is a flag 502 which is set to one level if the copyright noise signature is found, and to another level if it is not found. Also depicted is the fact that the standardized noise signature waveform is stored in Read Only Memory, 504, inside the IC 506. There will be a slight time delay between the application of an audio signal to the IC 506 and the output of a valid flag 502, due to the need to monitor some finite portion of the audio before a recognition can place. In this case, there may need to be a "flag valid" output 508 where the IC informs the external world if it has had enough time to make a proper determination of the presence or absence of the copyright noise signature.

Figure 11:
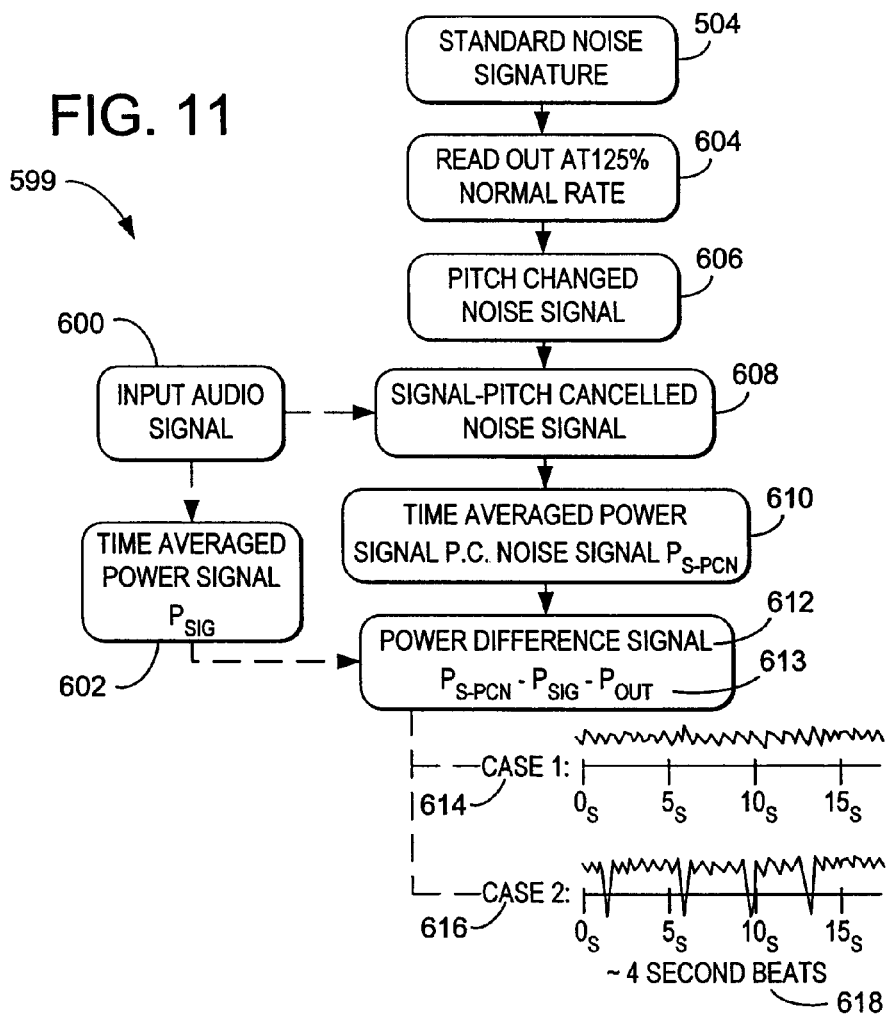
FIG. 11 shows a process flow for detecting a standard noise code that can be used in the FIG. 10 embodiment.
Figure 12:
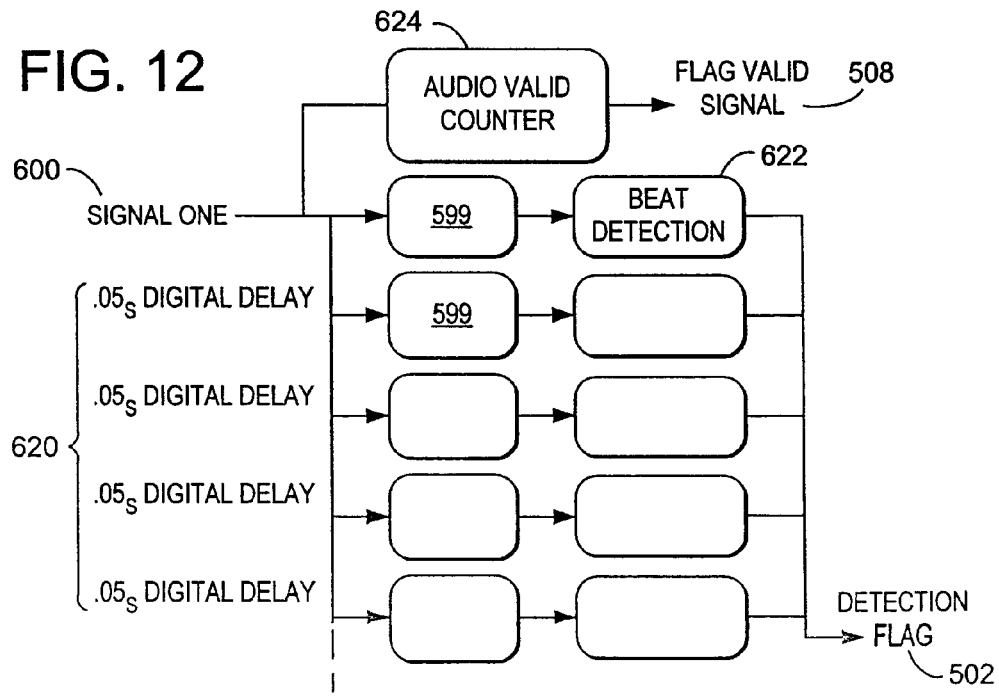
FIG. 12 is an embodiment employing a plurality of detectors in accordance with another embodiment of the present invention.

There are a wide variety of specific designs and philosophies of designs applied to accomplishing the basic function of the IC 506 of FIG. 10. Audio engineers and digital signal processing engineers are able to generate several fundamentally different designs. One such design is depicted in FIG. 11 by a process 599, which itself is subject to further engineering optimization as will be discussed. FIG. 11 depicts a flow chart for any of: an analog signal processing network, a digital signal processing network, or programming steps in a software program. We find an input signal 600 which along one path is applied to a time averaged power meter 602, and the resulting power output itself treated as a signal $P_{sig}$. To the upper right we find the standard noise signature 504 which will be read out at 125% of normal speed, 604, thus changing its pitch, giving the "pitch changed noise signal" 606. Then the input signal has this pitch changed noise signal subtracted in step 608, and this new signal is applied to the same form of time averaged power meter as in 602, here labelled 610. The output of this operation is also a time based signal here labelled as $P_{s\text{-}pcn}$, 610. Step 612 then subtracts the power signal 602 from the power signal 610, giving an output difference signal $P_{out}$, 613. If the universal standard noise signature does indeed exist on the input audio signal 600, then case 2, 616, will be created wherein a beat signal 618 of approximately 4 second period will show up on the output signal 613, and it remains to detect this beat signal with a step such as in FIG. 12, 622. Case 1, 614, is a steady noisy signal which exhibits no periodic beating. 125% at step 604 is chosen arbitrarily here, where engineering considerations would determine an optimal value, leading to different beat signal frequencies 618. Whereas waiting 4 seconds in this example would be quite a while, especially is you would want to detect at least two or three beats, FIG. 12 outlines how the basic design of FIG. 11 could be repeated and operated upon various delayed versions of the input signal, delayed by something like 1/20th of a second, with 20 parallel circuits working in concert each on a segment of the audio delayed by 0.05 seconds from their neighbors. In this way, a beat signal will show up approximately every 1/5th of a second and will look like a travelling wave down the columns of beat detection circuits. The existence or absence of this travelling beat wave triggers the detection flag 502. Meanwhile, there would be an audio signal monitor 624 which would ensure that, for example, at least two seconds of audio has been heard before setting the flag valid signal 508.

Though the audio example was described above, it should be clear to anyone in the art that the same type of definition of some repetitive universal noise signal or image could be applied to the many other signals, images, pictures, and physical media already discussed.

The above case deals only with a single bit plane of information, i.e., the noise signature signal is either there (1) or it isn't (0). For many applications, it would be nice to detect serial number information as well, which could then be used for more complex decisions, or for logging information on billing statements or whatnot. The same principles as the above would apply, but now there would be N independent noise signatures as depicted in FIG. 9 instead one single such signature. Typically, one such signature would be the master upon which the mere existence of a copyright marking is detected, and this would have generally higher power than the others, and then the other lower power "identification" noise signatures would be embedded into audio. Recognition circuits, once having found the existence of the primary noise signature, would then step through the other N noise signatures applying the same steps as described above. Where a beat signal is detected, this indicates the bit value of '1', and where no beat signal is detected, this indicates a bit value of '0'. It might be typical that N will equal 32, that way 232 number of identification codes are available to any given industry employing this invention.

Use of this Technology when the Length of the Identification Code is 1

The principles of this invention can obviously be applied in the case where only a single presence or absence of an identification signal—a fingerprint if you will—is used to provide confidence that some signal or image is copyrighted. The example above of the industry standard noise signature is one case in point. We no longer have the added confidence of the coin flip analogy, we no longer have tracking code capabilities or basic serial number capabilities, but many applications may not require these attributes and the added simplicity of a single fingerprint might outweigh these other attributes in any event.

The "Wallpaper" Analogy

The term "holographic" has been used in this disclosure to describe how an identification code number is distributed in a largely integral form throughout an encoded signal or image. This also refers to the idea that any given fragment of the signal or image contains the entire unique identification code number. As with physical implementations of holography, there are limitations on how small a fragment can become before one begins to lose this property, where the resolution limits of the holographic media are the main factor in this regard for holography itself. In the case of an uncorrupted distribution signal which has used the encoding device of FIG. 5, and which furthermore has used our "designed noise" of above wherein the zero's were randomly changed to a 1 or −1, then the extent of the fragment required is merely N contiguous samples in a signal or image raster line, where N is as defined previously being the length of our identification code number. This is an informational extreme; practical situations where noise and corruption are operative will require generally one, two or higher orders of magnitude more samples than this simple number N. Those skilled in the art will recognize that there are many variables involved in pinning down precise statistics on the size of the smallest fragment with which an identification can be made.

For tutorial purposes, the applicant also uses the analogy that the unique identification code number is "wallpapered" across and image (or signal). That is, it is repeated over and over again all throughout an image. This repetition of the ID code number can be regular, as in the use of the encoder of FIG. 5, or random itself, where the bits in the ID code 216 of FIG. 6 are not stepped through in a normal repetitive fashion but rather are randomly selected on each sample, and the random selection stored along with the value of the output 228 itself. in any event, the information carrier of the ID code, the individual embedded code signal, does change across the image or signal. Thus as the wallpaper analogy summarizes: the ID code repeats itself over and over, but the patterns that each repetition imprints change randomly accordingly to a generally unsleuthable key.

Lossy Data Compression

As earlier mentioned, the identification coding of the preferred embodiment withstands lossy data compression, and subsequent decompression. Such compression is finding increasing use, particularly in contexts such as the mass distribution of digitized entertainment programming (movies, etc.).

While data encoded according to the preferred embodiment of the present invention can withstand all types of lossy compression known to applicant, those expected to be most commercially important are the CCITT G3, CCITT G4, JPEG, MPEG and JBIG compression/decompression standards. The CCITT standards are widely used in black-and-white document compression (e.g. facsimile and document-storage). JPEG is most widely used with still images. MPEG is most widely used with moving images. JBIG is a likely successor to the CCITT standards for use with black-and-white imagery. Such techniques are well known to those in the lossy data compression field; a good overview can be found in Pennebaker et al, JPEG, Still Image Data Compression Standard, Van Nostrand Reinhold, N.Y., 1993.

Towards Steganography Proper and the Use of this Technology in Passing More Complex Messages or Information This disclosure concentrates on what above was called wallpapering a single identification code across an entire signal. This appears to be a desirable feature for many applications. However, there are other applications where it might be desirable to pass messages or to embed very long strings of pertinent identification information in signals and images. One of many such possible applications would be where a given signal or image is meant to be manipulated by several different groups, and that certain regions of an image are reserved for each group's identification and insertion of pertinent manipulation information.

In these cases, the code word 216 in FIG. 6 can actually change in some pre-defined manner as a function of signal or image position. For example, in an image, the code could change for each and every raster line of the digital image. It might be a 16 bit code word, 216, but each scan line would have a new code word, and thus a 480 scan line image could pass a 980 (480×2 bytes) byte message. A receiver of the message would need to have access to either the noise signal stored in memory 214, or would have to know the universal code structure of the noise codes if that method of coding was being used. To the best of applicant's knowledge, this is a novel approach to the mature field of steganography.

In all three of the foregoing applications of universal codes, it will often be desirable to append a short (perhaps 8- or 16-bit) private code, which users would keep in their own secured places, in addition to the universal code. This affords the user a further modicum of security against potential erasure of the universal codes by sophisticated pirates.

One Master Code Signal as a Distinction from N Independent Embedded Code Signals In certain sections of this disclosure, perhaps exemplified in the section on the realtime encoder, an economizing step was taken whereby the N independent and source-signal-coextensive embedded code signals were so designed that the non-zero elements of any given embedded code signal were unique to just that embedded code signal and no others. Said more carefully, certain pixels/sample points of a given signal were "assigned" to some pre-determined m'th bit location in our N-bit identification word. Furthermore, and as another basic optimization of implementation, the aggregate of these assigned pixels/samples across all N embedded code signals is precisely the extent of the source signal, meaning each and every pixel/sample location in a source signal is assigned one and only one m'th bit place in our N-bit identification word. (This is not to say, however, that each and every pixel MUST be modified). As a matter of simplification we can then talk about a single master code signal (or "Snowy Image") rather than N independent signals, realizing that pre-defined locations in this master signal correspond to unique bit locations in our N-bit identification word. We therefore construct, via this circuitous route, this rather simple concept on the single master noise signal. Beyond mere economization and simplification, there are also performance reasons for this shift, primarily derived from the idea that individual bit places in our N-bit identification word are no longer "competing" for the information carrying capacity of a single pixel/sample.

With this single master more clearly understood, we can gain new insights into other sections of this disclosure and explore further details within the given application areas.

More of Deterministic Universal Codes Using the Master Code Concept

One case in point is to further explore the use of Deterministic Universal Codes, labelled as item "2" in the sections devoted to universal codes. A given user of this technology may opt for the following variant use of the principles of this invention. The user in question might be a mass distributor of home videos, but clearly the principles would extend to all other potential users of this invention. FIG. 13 pictorially represents the steps involved. In the example the user is one "Alien Productions." They first create an image canvas which is coextensive to the size of the video frames of their movie "Bud's Adventures." On this canvas they print the name of the movie, they place their logo and company name. Furthermore, they have specific information at the bottom, such as the distribution lot for the mass copying that they are currently cranking out, and as indicated, they actually have a unique frame number indicated. Thus we find the example of a standard image 700 which forms the initial basis for the creation of a master Snowy Image (master code signal) which will be added into the original movie frame, creating an output distributable frame. This image 700 can be either black & white or color. The process of turning this image 700 into a pseudo random master code signal is alluded to by the encryption/scrambling routine 702, wherein the original image 700 is passed through any of dozens of well known scrambling methods. The depiction of the number "28" alludes to the idea that there can actually be a library of scrambling methods, and the particular method used for this particular movie, or even for this particular frame, can change. The result is our classic master code signal or Snowy Image. In general, its brightness values are large and it would look very much like the snowy image on a television set tuned to a blank channel, but clearly it has been derived from an informative image 700, transformed through a scrambling 702. (Note: the splotchiness of the example picture is actually a rather poor depiction; it was a function of the crude tools available to the inventor).

This Master Snowy Image 704 is then the signal which is modulated by our N-bit identification word as outlined in other sections of the disclosure, the resulting modulated signal is then scaled down in brightness to the acceptable perceived noise level, and then added to the original frame to produce the distributable frame.

There are a variety of advantages and features that the method depicted in FIG. 13 affords. There are also variations of theme within this overall variation. Clearly, one advantage is that users can now use more intuitive and personalized methods for stamping and signing their work. Provided that the encryption/scrambling routines, 702, are indeed of a high security and not published or leaked, then even if a would-be pirate has knowledge of the logo image 700, they should not be able to use this knowledge to be able to sleuth the Master Snowy Image 704, and thus they should not be able to crack the system, as it were. On the other hand, simple encryption routines 702 may open the door for cracking the system. Another clear advantage of the method of FIG. 13 is the ability to place further information into the overall protective process. Strictly speaking, the information contained in the logo image 700 is not directly carried in the final distributable frame. Said another way, and provided that the encryption/scrambling routine 702 has a straightforward and known decryption/descrambling method which tolerates bit truncation errors, it is generally impossible to fully re-create the image 700 based upon having the distributable frame, the N-bit identification code word, the brightness scaling factor used, and the number of the decryption routine to be used. The reason that an exact recreation of the image 700 is impossible is due to the scaling operation itself and the concomitant bit truncation. For the present discussion, this whole issue is somewhat academic, however.

A variation on the theme of FIG. 13 is to actually place the N-bit identification code word directly into the logo image 700. In some sense this would be self-referential. Thus when we pull out our stored logo image 700 it already contains visually what our identification word is, then we apply encryption routine #28 to this image, scale it down, then use this version to decode a suspect image using the techniques of this disclosure. The N bit word thus found should match the one contained in our logo image 700.

One desirable feature of the encryption/scrambling routine 702 might be (but is certainly not required to be) that even given a small change in the input image 700, such as a single digit change of the frame number, there would be a huge visual change in the output scrambled master snowy image 704. Likewise, the actual scrambling routine may change as a function of frame numbers, or certain "seed" numbers typically used within pseudo-randomizing functions could change as a function of frame number. All manner of variations are thus possible, all helping to maintain high levels of security. Eventually, engineering optimization considerations will begin to investigate the relationship between some of these randomizing methods, and how they all relate to maintaining acceptable signal strength levels through the process of transforming an uncompressed video stream into a compressed video stream such as with the MPEG compression methodologies.

Another desired feature of the encryption process 702 is that it should be informationally efficient, i.e., that given any random input, it should be able to output an essentially spatially uniform noisy image with little to no residual spatial patterns beyond pure randomness. Any residual correlated patterns will contribute to inefficiency of encoding the N-bit identification word, as well as opening up further tools to would-be pirates to break the system.

Another feature of the method of FIG. 13 is that there is more intuitive appeal to using recognizable symbols as part of a decoding system, which should then translate favorably in the essentially lay environment of a courtroom. It strengthens the simplicity of the coin flip vernacular mentioned elsewhere. Jury members or judges will better relate to an owner's logo as being a piece of the key of recognizing a suspect copy as being a knock-off.

It should also be mentioned that, strictly speaking, the logo image 700 does not need to be randomized. The steps of the invention could equally apply straight to the logo image 700 directly. It is not entirely clear to the inventor what practical goal this might have. A trivial extension of this concept to the case where N=1 is where, simply and easily, the logo image 700 is merely added to an original image at a very low brightness level. The inventor does not presume this trivial case to be at all a novelty. In many ways this is similar to the age old issue of subliminal advertising, where the low light level patterns added to an image are recognizable to the human eye/brain system and—supposedly—operating on the human brain at an unconscious level. By pointing out these trivial extensions of the current invention, hopefully there can arise further clarity which distinguishes the novel principles of this invention in relation to such well known prior art techniques.

5-bit Abridged Alphanumeric Code Sets and Others

It is desirable in some applications for the N-bit identification word to actually signify names, companies, strange words, messages, and the like. Most of this disclosure focuses on using the N-bit identification word merely for high statistical security, indexed tracking codes, and other index based message carrying. The information carrying capacity of "invisible signatures" inside imagery and audio is somewhat limited, however, and thus it would be wise to use our N bits efficiently if we actually want to "spell out" alphanumeric items in the N-bit identification word.

One way to do this is to define, or to use an already existing, reduced bit (e.g. less than 8-bit ASCII) standardized codes for passing alphanumeric messages. This can help to satisfy this need on the part of some applications. For example, a simple alphanumeric code could be built on a 5-bit index table, where for example the letters V, X, Q, and Z are not included, but the digits 0 through 9 are included. In this way, a 100 bit identification word could carry with it 20 alphanumeric symbols. Another alternative is to use variable bit length codes such as the ones used in text compression routines (e.g. Huffman) whereby more frequently used symbols have shorter bit length codes and less frequently used symbols have longer bit lengths.

More on Detecting and Recognizing the N-Bit Identification Word in Suspect Signals Classically speaking, the detection of the N-bit identification word fits nicely into the old art of detecting known signals in noise. Noise in this last statement can be interpreted very broadly, even to the point where an image or audio track itself can be considered noise, relative to the need to detect the underlying signature signals. One of many references to this older art is the book Kassam, Saleem A., "Signal Detection in Non-Guassian Noise," Springer-Verlag, 1988 (available at the Library of Congress by catalog number TK5102.5.K357 1988). To the best of this inventor's current understanding, none of the material in this book is directly applicable to the issue of discovering the polarity of embedded signals of this invention, but the broader principles are indeed applicable.

In particular, section 1.2 "Basic Concepts of Hypothesis Testing" of Kassam's book lays out the basic concept of a binary hypothesis, assigning the value "1" to one hypothesis and the value "0" to the other hypothesis. The last paragraph of that section is also on point regarding the initial preferred embodiment of this invention, i.e., that the "0" hypothesis corresponds to "noise only" case, whereas the "1" corresponds to the presence of a signal in the observations. (Chapters 1-3 of Kassam published as Appendix A in U.S. Published Patent Application No. US 2003-0002710 A1, which is herein incorporated by reference.) The current preferred embodiment of using true polarity is not like this however, where now the "0" corresponds to the presence of an inverted signal rather than to "noise-only." Also in the current preferred embodiment, the case of "noise-only" is effectively ignored, and that an identification process will either come up with our N-bit identification word or it will come up with "garbage."

The continued and inevitable engineering improvement in the detection of embedded code signals will undoubtedly borrow heavily from this generic field of known signal detection. A common and well-known technique in this field is the so-called "matched filter," which is incidentally discussed early in section 2 of the Kassam book. Many basic texts on signal processing include discussions on this method of signal detection. This is also known in some fields as correlation detection. Furthermore, when the phase or location of a known signal is known a priori, such as is often the case in applications of this invention, then the matched filter can often be reduced to a simple vector dot product between a suspect image and the embedded signal associated with an m'th bit plane in our N-bit identification word. This then represents yet another simple "detection algorithm" for taking a suspect image and producing a sequence of 1s and 0s with the intention of determining if that series corresponds to a pre-embedded N-bit identification word. In words, and with reference to FIG. 3, we run through the process steps up through and including the subtracting of the original image from the suspect, but the next step is merely to step through all N random independent signals and perform a simple vector dot product between these signals and the difference signal, and if that dot product is negative, assign a '0' and if that dot product is positive, assign a '1.' Careful analysis of this "one of many" algorithms will show its similarity to the traditional matched filter.

There are also some immediate improvements to the "matched filter" and "correlation-type" that can provide enhanced ability to properly detect very low level embedded code signals. Some of these improvements are derived from principles set forth in the Kassam book, others are generated by the inventor and the inventor has no knowledge of their being developed in other papers or works, but neither has the inventor done fully extensive searching for advanced signal detection techniques. One such technique is perhaps best exemplified by FIG. 3.5 in Kassam on page 79, wherein there are certain plots of the various locally optimum weighting coefficients which can apply to a general dot-product algorithmic approach to detection. In other words, rather than performing a simple dot product, each elemental multiplication operation in an overall dot product can be weighted based upon known a priori statistical information about the difference signal itself, i.e., the signal within which the low level known signals are being sought. The interested reader who is not already familiar with these topics is encouraged to read chapter 3 of Kassam to gain a fuller understanding.

Figure 14:
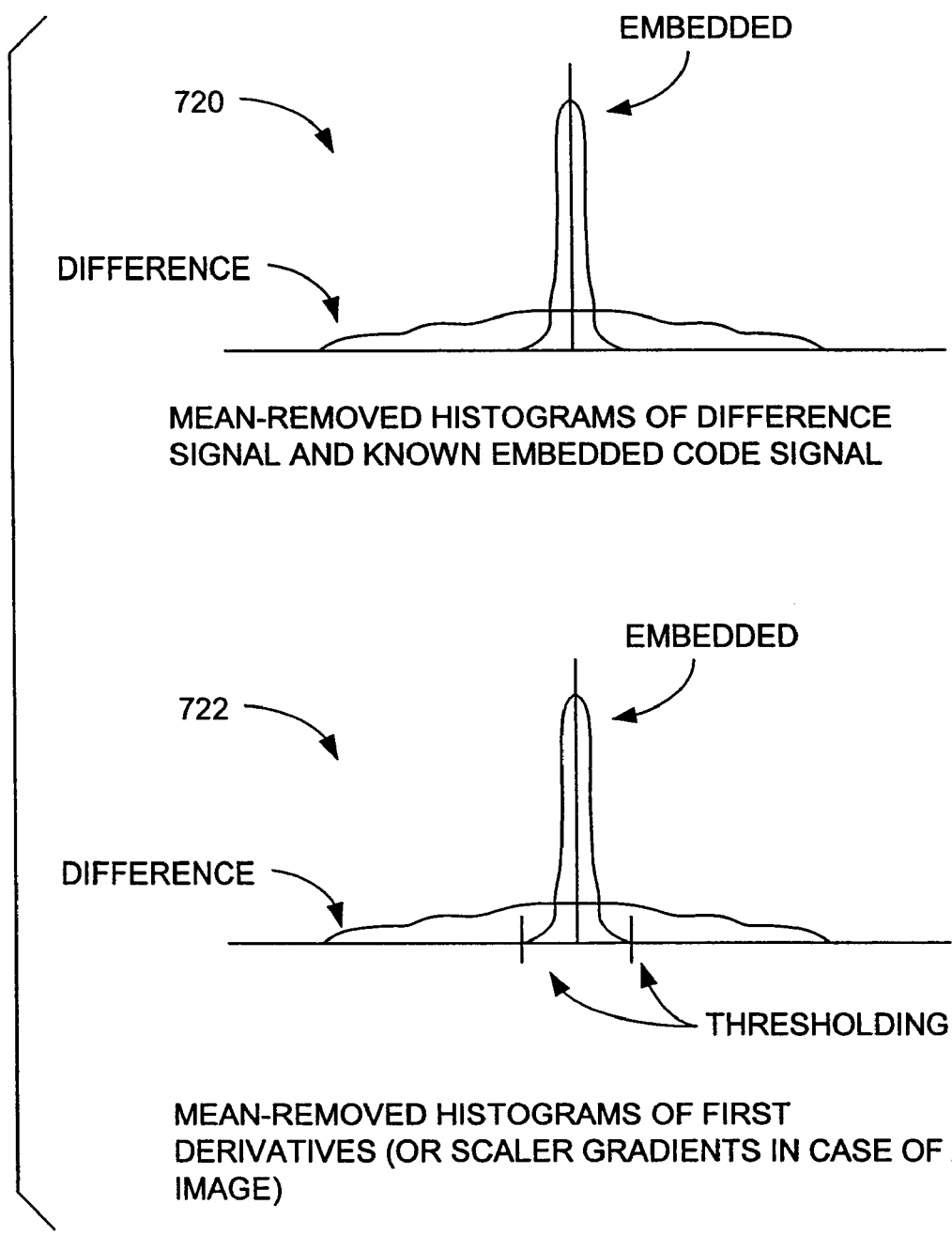
FIG. 14 illustrates how statistics of a signal can be used in aid of decoding.

One principle which did not seem to be explicitly present in the Kassam book and which was developed rudimentarily by the inventor involves the exploitation of the magnitudes of the statistical properties of the known signal being sought relative to the magnitude of the statistical properties of the suspect signal as a whole. In particular, the problematic case seems to be where the embedded signals we are looking for are of much lower level than the noise and corruption present on a difference signal. FIG. 14 attempts to set the stage for the reasoning behind this approach. The top FIG. 720 contains a generic look at the differences in the histograms between a typical "problematic" difference signal, i.e., a difference signal which has a much higher overall energy than the embedded signals that may or may not be within it. The term "mean-removed" simply means that the means of both the difference signal and the embedded code signal have been removed, a common operation prior to performing a normalized dot product. The lower FIG. 722 then has a generally similar histogram plot of the derivatives of the two signals, or in the case of an image, the scalar gradients. From pure inspection it can be seen that a simple thresholding operation in the derivative transform domain, with a subsequent conversion back into the signal domain, will go a long way toward removing certain innate biases on the dot product "recognition algorithm" of a few paragraphs back. Thresholding here refers to the idea that if the absolute value of a difference signal derivative value exceeds some threshold, then it is replaced simply by that threshold value. The threshold value can be so chosen to contain most of the histogram of the embedded signal.

Another operation which can be of minor assistance in "alleviating" some of the bias effects in the dot product algorithm is the removal of the low order frequencies in the difference signal, i.e., running the difference signal through a high pass filter, where the cutoff frequency for the high pass filter is relatively near the origin (or DC) frequency.

Special Considerations for Recognizing Embedded Codes on Signals which have been Compressed and Decompressed, or Alternatively, for Recognizing Embedded Codes within any Signal which has Undergone Some Known Process which Creates Non-Uniform Error Sources Long title for a basic concept. Some signal processing operations, such as compressing and decompressing an image, as with the JPEG/MPEG formats of image/video compression, create errors in some given transform domain which have certain correlations and structure. Using JPEG as an example, if a given image is compressed then decompressed at some high compression ratio, and that resulting image is then fourier transformed and compared to the fourier transform of the original uncompressed image, a definite pattern is clearly visible. This patterning is indicative of correlated error, i.e. error which can be to some extent quantified and predicted. The prediction of the grosser properties of this correlated error can then be used to advantage in the heretofore-discussed methods of recognizing the embedded code signals within some suspect image which may have undergone either JPEG compression or any other operation which leaves these telltale correlated error signatures. The basic idea is that in areas where there are known higher levels of error, the value of the recognition methods is diminished relative to the areas with known lower levels of correlated errors. It is often possible to quantify the expected levels of error and use this quantification to appropriately weight the retransformed signal values. Using JPEG compression again as an example, a suspect signal can be fourier transformed, and the fourier space representation may clearly show the telltale box grid pattern. The fourier space signal can then be "spatially filtered" near the grid points, and this filtered representation can then be transformed back into its regular time or space domain to then be run through the recognition methods presented in this disclosure. Likewise, any signal processing method which creates non-uniform error sources can be transformed into the domain in which these error sources are non-uniform, the values at the high points of the error sources can be attenuated, and the thusly "filtered" signal can be transformed back into the time/space domain for standard recognition. Often this whole process will include the lengthy and arduous step of "characterizing" the typical correlated error behavior in order to "design" the appropriate filtering profiles.

"Signature Codes" and "Invisible Signatures"

Briefly and for the sake of clarity, the phrases and terms "signatures," "invisible signatures," and "signature codes" have been and will continue to be used to refer to the general techniques of this invention and often refer specifically to the composite embedded code signal as defined early on in this disclosure.

More Details on Embedding Signature Codes into Motion Pictures

Just as there is a distinction made between the JPEG standards for compressing still images and the MPEG standards for compressed motion images, so too should there be distinctions made between placing invisible signatures into still images and placing signatures into motion images. As with the JPEG/MPEG distinction, it is not a matter of different foundations, it is the fact that with motion images a new dimension of engineering optimization opens up by the inclusion of time as a parameter. Any textbook dealing with MPEG will surely contain a section on how MPEG is (generally) not merely applying JPEG on a frame by frame basis. It will be the same with the application of the principles of this invention: generally speaking, the placement of invisible signatures into motion image sequences will not be simply independently placing invisible signatures into one frame after the next. A variety of time-based considerations come into play, some dealing with the psychophysics of motion image perception, others driven by simple cost engineering considerations.

One preferred embodiment is the following. This example actually uses the MPEG compression standard as a piece of a solution. Other motion image compression schemes could equally well be used, be they already invented or yet to be invented. This example also utilizes the scrambled logo image approach to generating the master snowy image as depicted in FIG. 13 and discussed in the disclosure.

Figure 15:
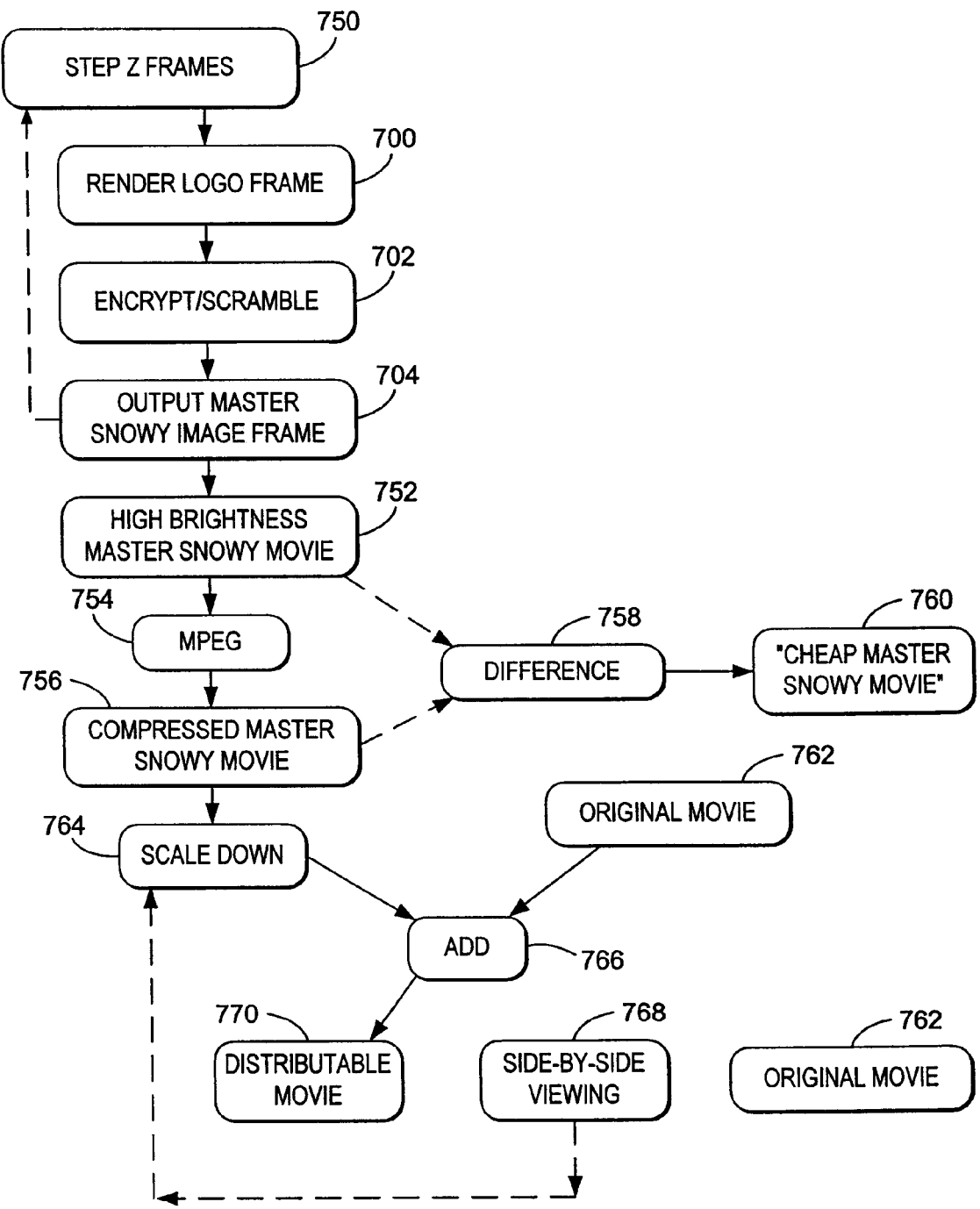
FIG. 15 shows how a signature signal can be preprocessed to increase its robustness in view of anticipated distortion, e.g. MPEG.

A "compressed master snowy image" is independently rendered as depicted in FIG. 15. "Rendered" refers to the generally well known technique in video, movie and animation production whereby an image or sequence of images is created by constructive techniques such as computer instructions or the drawing of animation cells by hand. Thus, "to render" a signature movie in this example is essentially to let either a computer create it as a digital file or to design some custom digital electronic circuitry to create it.

The overall goal of the procedure outlined in FIG. 15 is to apply the invisible signatures to the original movie 762 in such a way that the signatures do not degrade the commercial value of the movie, memorialized by the side-by-side viewing, 768, AND in such a way that the signature optimally survives through the MPEG compression and decompression process. As noted earlier, the use of the MPEG process in particular is an example of the generic process of compression. Also it should be noted that the example presented here has definite room for engineering variations. In particular, those practiced in the art of motion picture compression will appreciate the fact if we start out with two video streams A and B, and we compress A and B separately and combine their results, then the resultant video stream C will not generally be the same as if we pre-added the video streams A and B and compressed this resultant. Thus we have in general, e.g.:

MPEG(A)+MPEG(B)=\=MPEG(A+B)

where =\= is not equal to. This is somewhat an abstract notion to introduce at this point in the disclosure and will become more clear as FIG. 15 is discussed. The general idea, however, is that there will be a variety of algebras that can be used to optimize the pass-through of "invisible" signatures through compression procedures. Clearly, the same principles as depicted in FIG. 15 also work on still images and the JPEG or any other still image compression standard.

Turning now to the details of FIG. 15, we begin with the simple stepping through of all Z frames of a movie or video. For a two hour movie played at 30 frames per second, Z turns out to be (30*2*60*60) or 216,000. The inner loop of 700, 702 and 704 merely mimics FIG. 13's steps. The logo frame optionally can change during the stepping through frames. The two arrows emanating from the box 704 represent both the continuation of the loop 750 and the depositing of output frames into the rendered master Snowy Image 752.

To take a brief but potentially appropriate digression at this point, the use of the concept of a Markov process brings certain clarity to the discussion of optimizing the engineering implementation of the methods of FIG. 15. Briefly, a Markov process is one in which a sequence of events takes place and in general there is no memory between one step in the sequence and the next. In the context of FIG. 15 and a sequence of images, a Markovian sequence of images would be one in which there is no apparent or appreciable correlation between a given frame and the next. Imagine taking the set of all movies ever produced, stepping one frame at a time and selecting a random frame from a random movie to be inserted into an output movie, and then stepping through, say, one minute or 1800 of these frames. The resulting "movie" would be a fine example of a Markovian movie. One point of this discussion is that depending on how the logo frames are rendered and depending on how the encryption/scrambling step 702 is performed, the Master Snowy Movie 752 will exhibit some generally quantifiable degree of Markovian characteristics. The point of this point is that the compression procedure itself will be affected by this degree of Markovian nature and thus needs to be accounted for in designing the process of FIG. 15. Likewise, and only in general, even if a fully Markovian movie is created in the High Brightness Master Snowy Movie, 752, then the processing of compressing and decompressing that movie 752, represented as the MPEG box 754, will break down some of the Markovian nature of 752 and create at least a marginally non-Markovian compressed master Snowy Movie 756. This point will be utilized when the disclosure briefly discusses the idea of using multiple frames of a video stream in order to find a single N-bit identification word, that is, the same N-bit identification word may be embedded into several frames of a movie, and it is quite reasonable to use the information derived from those multiple frames to find that single N-bit identification word. The non-Markovian nature of 756 thus adds certain tools to reading and recognizing the invisible signatures. Enough of this tangent.

With the intent of pre-conditioning the ultimately utilized Master Snowy Movie 756, we now send the rendered High Brightness Master Snowy Movie 752 through both the MPEG compression AND decompression procedure 754. With the caveat previously discussed where it is acknowledged that the MPEG compression process is generally not distributive, the idea of the step 754 is to crudely segregate the initially rendered Snowy Movie 752 into two components, the component which survives the compression process 754 which is 756, and the component which does not survive, also crudely estimated using the difference operation 758 to produce the "Cheap Master Snowy Movie" 760. The reason use is made of the deliberately loose term "Cheap" is that we can later add this signature signal as well to a distributable movie, knowing that it probably won't survive common compression processes but that nevertheless it can provide "cheap" extra signature signal energy for applications or situations which will never experience compression. [Thus it is at least noted in FIG. 15]. Back to FIG. 15 proper, we now have a rough cut at signatures which we know have a higher likelihood of surviving intact through the compression process, and we use this "Compressed Master Snowy Movie" 756 to then go through this invention's procedure of being scaled down 764, added to the original movie 766, producing a candidate distributable movie 770, then compared to the original movie (768) to ensure that it meets whatever commercially viable criteria which have been set up (i.e. the acceptable perceived noise level). The arrow from the side-by-side step 768 back to the scale down step 764 corresponds quite directly to the "experiment visually . . . " step of FIG. 2, and the gain control 226 of FIG. 6. Those practiced in the art of image and audio information theory can recognize that the whole of FIG. 15 can be summarized as attempting to pre-condition the invisible signature signals in such a way that they are better able to withstand even quite appreciable compression. To reiterate a previously mentioned item as well, this idea equally applies to ANY such pre-identifiable process to which an image, and image sequence, or audio track might be subjected. This clearly includes the JPEG process on still images.

Additional Elements of the Realtime Encoder Circuitry

It should be noted that the method steps represented in FIG. 15, generally following from box 750 up through the creation of the compressed master snowy movie 756, could with certain modification be implemented in hardware. In particular, the overall analog noise source 206 in FIG. 6 could be replaced by such a hardware circuit. Likewise the steps and associated procedures depicted in FIG. 13 could be implemented in hardware and replace the analog noise source 206.

Recognition Based on More than One Frame: Non-Markovian Signatures

As noted in the digression on Markov and non-Markov sequences of images, it is pointed out once again that in such circumstances where the embedded invisible signature signals are non-Markovian in nature, i.e., that there is some correlation between the master snowy image of one frame to that of the next, AND furthermore that a single N-bit identification word is used across a range of frames and that the sequence of N-bit identification words associated with the sequence of frames is not Markovian in nature, then it is possible to utilize the data from several frames of a movie or video in order to recognize a single N-bit identification word. All of this is a fancy way of saying that the process of recognizing the invisible signatures should use as much information as is available, in this case translating to multiple frames of a motion image sequence.

Header Verification

The concept of the "header" on a digital image or audio file is a well established practice in the art. The top of FIG. 16 has a simplified look at the concept of the header, wherein a data file begins with generally a comprehensive set of information about the file as a whole, often including information about who the author or copyright holder of the data is, if there is a copyright holder at all. This header 800 is then typically followed by the data itself 802, such as an audio stream, a digital image, a video stream, or compressed versions of any of these items. This is all exceedingly known and common in the industry.

Figure 16:
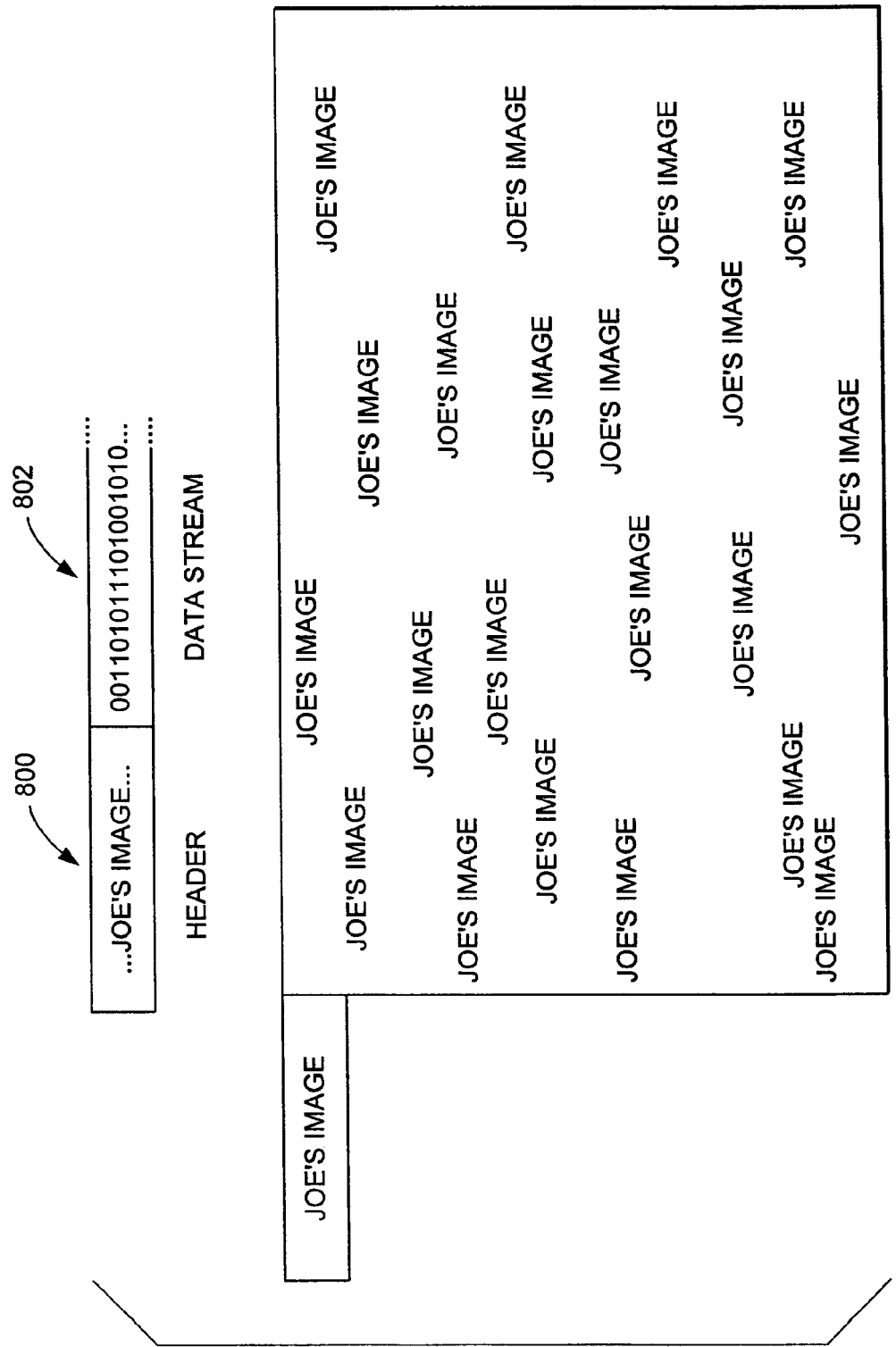
FIGS. 16 and 17 show embodiments of the invention in which information about a file is detailed both in a header, and in the file itself.

One way in which the principles of this invention can be employed in the service of information integrity is generically depicted in the lower diagram of FIG. 16. In general, the N-bit identification word can be used to essentially "wallpaper" a given simple message throughout an image (as depicted) or audio data stream, thereby reinforcing some message already contained in a traditional header. This is referred to as "header verification" in the title of this section. The thinking here is that less sophisticated would-be pirates and abusers can alter the information content of header information, and the more secure techniques of this inventions can thus be used as checks on the veracity of header information. Provided that the code message, such as "joe's image" in the header, matches the repeated message throughout an image, then a user obtaining the image can have some higher degree of confidence that no alteration of the header has taken place.

Likewise, the header can actually carry the N-bit identification word so that the fact that a given data set has been coded via the methods of this invention can be highlighted and the verification code built right into the header. Naturally, this data file format has not been created yet since the principles of this invention are currently not being employed.

The "Bodier": The Ability to Largely Replace a Header

Although all of the possible applications of the following aspect of the invention are not fully developed, it is nevertheless presented as a design alternative that may be important some day. The title of this section contains the silly phrase used to describe this possibility: the "bodier."

Whereas the previous section outlined how the N-bit identification word could "verify" information contained within the header of a digital file, there is also the prospect that the methods of this invention could completely replace the very concept of the header and place the information which is traditionally stored in the header directly into the digital signal and empirical data itself.

This could be as simple as standardizing on, purely for example, a 96-bit (12 bytes) leader string on an otherwise entirely empirical data stream. This leader string would plain and simple contain the numeric length, in elemental data units, of the entire data file not including the leader string, and the number of bits of depth of a single data element (e.g. its number of grey levels or the number of discrete signal levels of an audio signal). From there, universal codes as described in this specification would be used to read the N-bit identification word written directly within the empirical data. The length of the empirical data would need to be long enough to contain the full N bits. The N-bit word would effectively transmit what would otherwise be contained in a traditional header.

Figure 17:
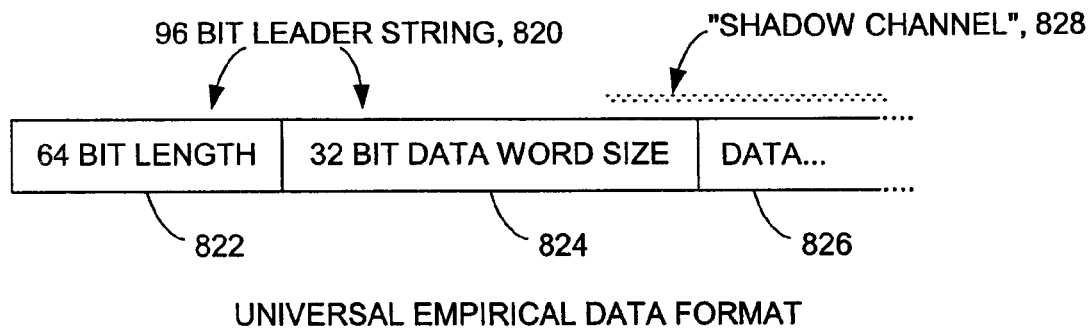

FIG. 17 depicts such a data format and calls it the "universal empirical data format." The leader string 820 is comprised of the 64 bit string length 822 and the 32 bit data word size 824. The data stream 826 then immediately follows, and the information traditionally contained in the header but now contained directly in the data stream is represented as the attached dotted line 828. Another term used for this attached information is a "shadow channel" as also depicted in FIG. 17.

Yet another element that may need to be included in the leader string is some sort of complex check sum bits which can verify that the whole of the data file is intact and unaltered. This is not included in FIG. 17.

More on Distributed Universal Code Systems: Dynamic Codes

One intriguing variation on the theme of universal codes is the possibility of the N-bit identification word actually containing instructions which vary the operations of the universal code system itself. One of many examples is immediately in order: a data transmission is begun wherein a given block of audio data is fully transmitted, an N-bit identification word is read knowing that the first block of data used universal codes #145 out of a set of 500, say, and that part of the N-bit identification word thus found is the instructions that the next block of data should be "analyzed" using the universal code set #411 rather than #145. In general, this invention can thus be used as a method for changing on the fly the actual decoding instructions themselves. Also in general, this ability to utilize "dynamic codes" should greatly increase the sophistication level of the data verification procedures and increase the economic viability of systems which are prone to less sophisticated thwarting by hackers and would-be pirates. The inventor does not believe that the concept of dynamically changing decoding/decrypting instructions is novel per se, but the carrying of those instructions on the "shadow channel" of empirical data does appear to be novel to the best of the inventor's understanding. [Shadow channel was previously defined as yet another vernacular phrase encapsulating the more steganographic proper elements of this invention].

A variant on the theme of dynamic codes is the use of universal codes on systems which have a priori assigned knowledge of which codes to use when. One way to summarize this possibility is the idea of "the daily password." The password in this example represents knowledge of which set of universal codes is currently operative, and these change depending on some set of application-specific circumstances. Presumably many applications would be continually updating the universal codes to ones which had never before been used, which is often the case with the traditional concept of the daily password. Part of a currently transmitted N-bit identification word could be the passing on of the next day's password, for example. Though time might be the most common trigger events for the changing of passwords, there could be event based triggers as well.

Symmetric Patterns and Noise Patterns: Toward a Robust Universal Coding System

The placement of identification patterns into images is certainly not new. Logos stamped into corners of images, subtle patterns such as true signatures or the wallpapering of the copyright circle-C symbol, and the watermark proper are all examples of placing patterns into images in order to signify ownership or to try to prevent illicit uses of the creative material.

What does appear to be novel is the approach of placing independent "carrier" patterns, which themselves are capable of being modulated with certain information, directly into images and audio for the purposes of transmission and discernment of said information, while effectively being imperceptible and/or unintelligible to a perceiving human. Steganographic solutions currently known to the inventor all place this information "directly" into empirical data (possibly first encrypted, then directly), whereas the methods of this disclosure posit the creation of these (most-often) coextensive carrier signals, the modulation of those carrier signals with the information proper, THEN the direct application to the empirical data.

In extending these concepts one step further into the application arena of universal code systems, where a sending site transmits empirical data with a certain universal coding scheme employed and a receiving site analyzes said empirical data using the universal coding scheme, it would be advantageous to take a closer look at the engineering considerations of such a system designed for the transmission of images or motion images, as opposed to audio. Said more clearly, the same type of analysis of a specific implementation such as is contained in FIG. 9 and its accompanying discussion on the universal codes in audio applications should as well be done on imagery (or two dimensional signals). This section is such an analysis and outline of a specific implementation of universal codes and it attempts to anticipate various hurdles that such a method should clear.

The unifying theme of one implementation of a universal coding system for imagery and motion imagery is "symmetry." The idea driving this couldn't be more simple: a prophylactic against the use of image rotation as a means for less sophisticated pirates to bypass any given universal coding system. The guiding principle is that the universal coding system should easily be read no matter what rotational orientation the subject imagery is in. These issues are quite common in the fields of optical character recognition and object recognition, and these fields should be consulted for further tools and tricks in furthering the engineering implementation of this invention. As usual, an immediate example is in order.

Digital Video And Internet Company XYZ has developed a delivery system of its product which relies on a non-symmetric universal coding which double checks incoming video to see if the individual frames of video itself, the visual data, contain XYZ's own relatively high security internal signature codes using the methods of this invention. This works well and fine for many delivery situations, including their Internet tollgate which does not pass any material unless both the header information is verified AND the in-frame universal codes are found. However, another piece of their commercial network performs mundane routine monitoring on Internet channels to look for unauthorized transmission of their proprietary creative property. They control the encryption procedures used, thus it is no problem for them to unencrypt creative property, including headers, and perform straightforward checks. A pirate group that wants to traffic material on XYZ's network has determined how to modify the security features in XYZ's header information system, and they have furthermore discovered that by simply rotating imagery by 10 or 20 degrees, and transmitting it over XYZ's network, the network doesn't recognize the codes and therefore does not flag illicit uses of their material, and the receiver of the pirate's rotated material simply unrotates it.

Summarizing this last example via logical categories, the non-symmetric universal codes are quite acceptable for the "enablement of authorized action based on the finding of the codes," whereas it can be somewhat easily by-passed in the case of "random monitoring (policing) for the presence of codes." [Bear in mind that the non-symmetric universal codes may very well catch 90% of illicit uses, i.e. 90% of the illicit users wouldn't bother even going to the simple by-pass of rotation.] To address this latter category, the use of quasi-rotationally symmetric universal codes is called for. "Quasi" derives from the age old squaring the circle issue, in this instance translating into not quite being able to represent a full incrementally rotational symmetric 2-D object on a square grid of pixels. Furthermore, basic considerations must be made for scale/magnification changes of the universal codes. It is understood that the monitoring process must be performed when the monitored visual material is in the "perceptual" domain, i.e. when it has been unencrypted or unscrambled and in the form with which it is (or would be) presented to a human viewer. Would-be pirates could attempt to use other simple visual scrambling and unscrambling techniques, and tools could be developed to monitor for these telltale scrambled signals. Said another way, would-be pirates would then look to transform visual material out of the perceptual domain, pass by a monitoring point, and then transform the material back into the perceptual domain; tools other than the monitoring for universal codes would need to be used in such scenarios. The monitoring discussed here therefore applies to applications where monitoring can be performed in the perceptual domain, such as when it is actually sent to viewing equipment.

The "ring" is the only full rotationally symmetric two dimensional object. The "disk" can be seen as a simple finite series of concentric and perfectly abutted rings having width along their radial axis. Thus, the "ring" needs to be the starting point from which a more robust universal code standard for images is found. The ring also will fit nicely into the issue of scale/magnification changes, where the radius of a ring is a single parameter to keep track of and account for. Another property of the ring is that even the case where differential scale changes are made to different spatial axes in an image, and the ring turns into an oval, many of the smooth and quasi-symmetric properties that any automated monitoring system will be looking for are generally maintained. Likewise, appreciable geometric distortion of any image will clearly distort rings but they can still maintain gross symmetric properties. Hopefully, more pedestrian methods such as simply "viewing" imagery will be able to detect attempted illicit piracy in these regards, especially when such lengths are taken to by-pass the universal coding system.

Rings to Knots

Having discovered the ring as the only ideal symmetric pattern upon whose foundation a full rotationally robust universal coding system can be built, we must turn this basic pattern into something functional, something which can carry information, can be read by computers and other instrumentation, can survive simple transformations and corruptions, and can give rise to reasonably high levels of security (probably not unbreakable, as the section on universal codes explained) in order to keep the economics of subversion as a simple incremental cost item.

Figure 18:
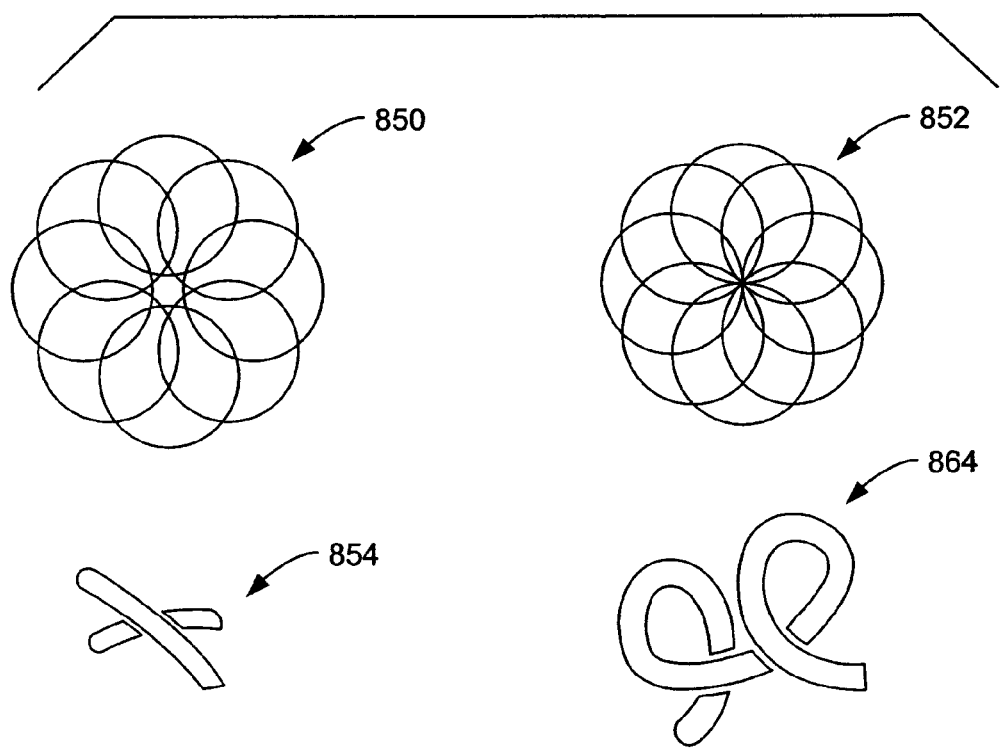
FIGS. 18-20 show details relating to embodiments of the present invention using rotationally symmetric patterns.
Figure 19:
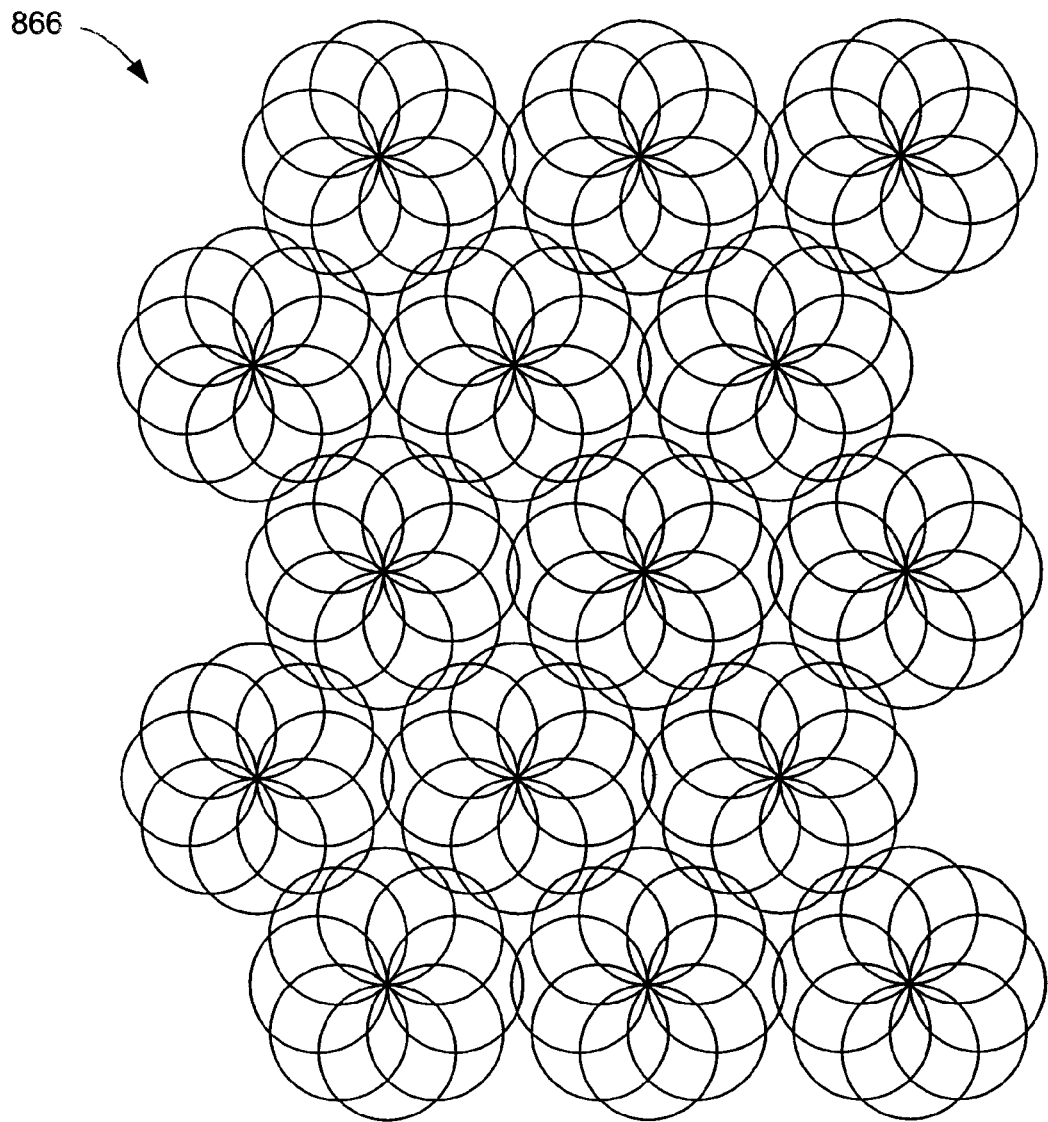

One current preferred embodiment of the "ring-based" universal codes is what the inventor refers to as "knot patterns" or simply "knots," in deference to woven Celtic knot patterns which were later refined and exalted in the works of Leonardo Da Vinci (e.g. Mona Lisa, or his knot engravings). Some rumors have it that these drawings of knots were indeed steganographic in nature, i.e. conveying messages and signatures; all the more appropriate. FIGS. 18 and 19 explore some of the fundamental properties of these knots.

Two simple examples of knot patterns are depicted by the supra-radial knots, 850 and the radial knots 852. The names of these types are based on the central symmetry point of the splayed rings and whether the constituent rings intersect this point, are fully outside it, or in the case of sub-radial knots the central point would be inside a constituent circle. The examples of 850 and 852 clearly show a symmetrical arrangement of 8 rings or circles. "Rings" is the more appropriate term, as discussed above, in that this term explicitly acknowledges the width of the rings along the radial axis of the ring. It is each of the individual rings in the knot patterns 850 and 852 which will be the carrier signal for a single associated bit plane in our N-bit identification word. Thus, the knot patterns 850 and 852 each are an 8-bit carrier of information. Specifically, assuming now that the knot patterns 850 and 852 are luminous rings on a black background, then the "addition" of a luminous ring to an independent source image could represent a "1" and the "subtraction" of a luminous ring from an independent source image could represent a "0." The application of this simple encoding scheme could then be replicated over and over as in FIG. 19 and its mosaic of knot patterns, with the ultimate step of adding a scaled down version of this encoded (modulated) knot mosaic directly and coextensively to the original image, with the resultant being the distributable image which has been encoded via this universal symmetric coding method. It remains to communicate to a decoding system which ring is the least significant bit in our N-bit identification word and which is the most significant. One such method is to make a slightly ascending scale of radii values (of the individual rings) from the LSB to the MSB. Another is to merely make the MSB, say, 10% larger radius than all the others and to pre-assign counterclockwise as the order with which the remaining bits fall out. Yet another is to put some simple hash mark inside one and only one circle. In other words, there are a variety of ways with which the bit order of the rings can be encoded in these knot patterns.

The preferred embodiment for the decoding of, first of all checking for the mere existence of these knot patterns, and second, for the reading of the N-bit identification word, is as follows. A suspect image is first fourier transformed via the extremely common 2D FFT computer procedure. Assuming that we don't know the exact scale of the knot patterns, i.e., we don't know the radius of an elemental ring of the knot pattern in the units of pixels, and that we don't know the exact rotational state of a knot pattern, we merely inspect (via basic automated pattern recognition methods) the resulting magnitude of the Fourier transform of the original image for telltale ripple patterns (concentric low amplitude sinusoidal rings on top of the spatial frequency profile of a source image). The periodicity of these rings, along with the spacing of the rings, will inform us that the universal knot patterns are or are not likely present, and their scale in pixels. Classical small signal detection methods can be applied to this problem just as they can to the other detection methodologies of this disclosure. Common spatial filtering can then be applied to the fourier transformed suspect image, where the spatial filter to be used would pass all spatial frequencies which are on the crests of the concentric circles and block all other spatial frequencies. The resulting filtered image would be fourier transformed out of the spatial frequency domain back into the image space domain, and almost by visual inspection the inversion or non-inversion of the luminous rings could be detected, along with identification of the MSB or LSB ring, and the (in this case 8) N-bit identification code word could be found. Clearly, a pattern recognition procedure could perform this decoding step as well.

The preceding discussion and the method it describes has certain practical disadvantages and shortcomings which will now be discussed and improved upon. The basic method was presented in a simple-minded fashion in order to communicate the basic principles involved.

Let's enumerate a few of the practical difficulties of the above described universal coding system using the knot patterns. For one (1), the ring patterns are somewhat inefficient in their "covering" of the full image space and in using all of the information carrying capacity of an image extent. Second (2), the ring patterns themselves will almost need to be more visible to the eye if they are applied, say, in a straightforward additive way to an 8-bit black and white image. Next (3), the "8" rings of FIGS. 18, 850 and 852, is a rather low number, and moreover, there is a 22 and one half degree rotation which could be applied to the figures which the recognition methods would need to contend with (360 divided by 8 divided by 2). Next (4), strict overlapping of rings would produce highly condensed areas where the added and subtracted brightness could become quite appreciable. Next (5), the 2D FFT routine used in the decoding is notoriously computationally cumbersome as well as some of the pattern recognition methods alluded to. Finally (6), though this heretofore described form of universal coding does not pretend to have ultra-high security in the classical sense of top security communications systems, it would nevertheless be advantageous to add certain security features which would be inexpensive to implement in hardware and software systems which at the same time would increase the cost of would-be pirates attempting to thwart the system, and increase the necessary sophistication level of those pirates, to the point that a would-be pirate would have to go so far out of their way to thwart the system that willfulness would be easily proven and hopefully subject to stiff criminal liability and penalty (such as the creation and distribution of tools which strip creative property of these knot pattern codes).

All of these items can be addressed and should continue to be refined upon in any engineering implementation of the principles of the invention. This disclosure addresses these items with the following current preferred embodiments.

Beginning with item number 3, that there are only 8 rings represented in FIG. 18 is simply remedied by increasing the number of rings. The number of rings that any given application will utilize is clearly a function of the application. The trade-offs include but are not limited to: on the side which argues to limit the number of rings utilized, there will ultimately be more signal energy per ring (per visibility) if there are less rings; the rings will be less crowded so that there discernment via automated recognition methods will be facilitated; and in general since they are less crowded, the full knot pattern can be contained using a smaller overall pixel extent, e.g. a 30 pixel diameter region of image rather than a 100 pixel diameter region. The arguments to increase the number of rings include: the desire to transmit more information, such as ascii information, serial numbers, access codes, allowed use codes and index numbers, history information, etc.; another key advantage of having more rings is that the rotation of the knot pattern back into itself is reduced, thereby allowing the recognition methods to deal with a smaller range of rotation angles (e.g., 64 rings will have a maximum rotational displacement of just under 3 degrees, i.e. maximally dissimilar to its original pattern, where a rotation of about 5 and one half degrees brings the knot pattern back into its initial alignment; the need to distinguish the MSB/LSB and the bit plane order is better seen in this example as well). It is anticipated that most practical applications will choose between 16 and 128 rings, corresponding to N=16 to N=128 for the choice of the number of bits in the N-bit identification code word. The range of this choice would somewhat correlate to the overall radius, in pixels, allotted to an elemental knot pattern such as 850 or 852.

Addressing the practical difficulty item number 4, that of the condensation of rings patterns at some points in the image and lack of ring patterns in others (which is very similar, but still distinct from, item 1, the inefficient covering), the following improvement can be applied. FIG. 18 shows an example of a key feature of a "knot" (as opposed to a pattern of rings) in that where patterns would supposedly intersect, a virtual third dimension is posited whereby one strand of the knot takes precedence over another strand in some predefined way; see item 854. In the terms of imagery, the brightness or dimness of a given intersection point in the knot patterns would be "assigned" to one and only one strand, even in areas where more than two strands overlap. The idea here is then extended, 864, to how rules about this assignment should be carried out in some rotationally symmetric manner. For example, a rule would be that, travelling clockwise, an incoming strand to a loop would be "behind" an outgoing strand. Clearly there are a multitude of variations which could be applied to these rules, many which would critically depend on the geometry of the knot patterns chosen. Other issues involved will probably be that the finite width, and moreover the brightness profile of the width along the normal axis to the direction of a strand, will all play a role in the rules of brightness assignment to any given pixel underlying the knot patterns.

Figure 20:
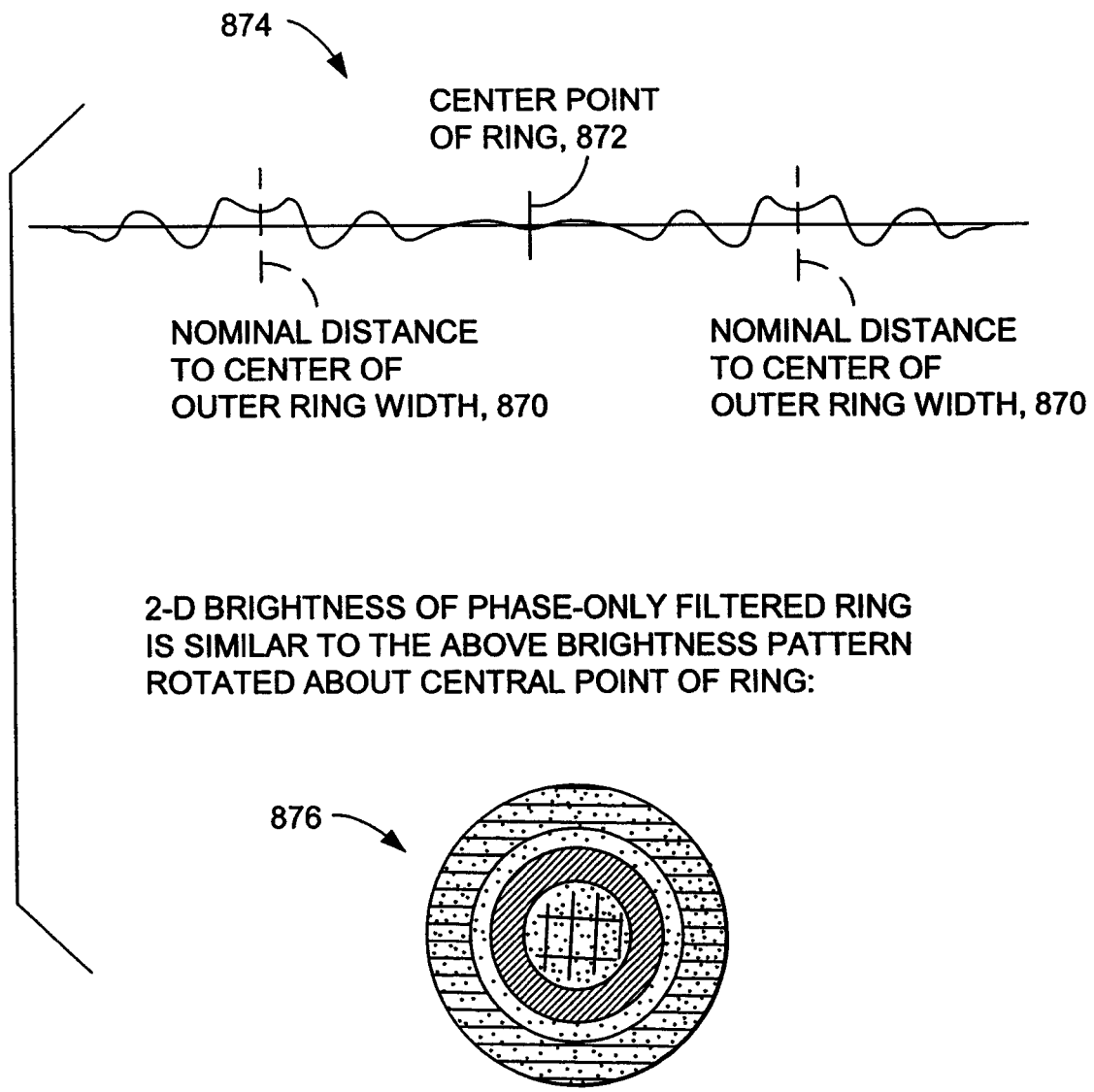

A major improvement to the nominal knot pattern system previously described directly addresses practical difficulties (1), the inefficient covering, (2) the unwanted visibility of the rings, and (6) the need for higher levels of security. This improvement also indirectly address item (4) the overlapping issue, which has been discussed in the last paragraph. This major improvement is the following: just prior to the step where the mosaic of the encoded knot patterns is added to an original image to produce a distributable image, the mosaic of encoded knot patterns, 866, is spatially filtered (using common 2D FFT techniques) by a standardized and (generally smoothly) random phase-only spatial filter. It is very important to note that this phase-only filter is itself fully rotationally symmetric within the spatial frequency domain, i.e. its filtering effects are fully rotationally symmetric. The effect of this phase-only filter on an individual luminous ring is to transform it into a smoothly varying pattern of concentric rings, not totally dissimilar to the pattern on water several instances after a pebble is dropped in, only that the wave patterns are somewhat random in the case of this phase-only filter rather than the uniform periodicity of a pebble wave pattern. FIG. 20 attempts to give a rough (i.e. non-greyscale) depiction of these phase-only filtered ring patterns. The top figure of FIG. 20 is a cross section of a typical brightness contour/profile

874 of one of these phase-only filtered ring patterns. Referenced in the figure is the nominal location of the pre-filtered outer ring center, 870. The center of an individual ring, 872, is referenced as the point around which the brightness profile is rotated in order to fully describe the two dimensional brightness distribution of one of these filtered patterns. Yet another rough attempt to communicate the characteristics of the filtered ring is depicted as 876, a crude greyscale image of the filtered ring. This phase-only filtered ring, 876 will can be referred to as a random ripple pattern.

Not depicted in FIG. 20 is the composite effects of phase-only filtering on the knot patterns of FIG. 18, or on the mosaic of knot patterns 866 in FIG. 19. Each of the individual rings in the knot patterns 850 or 852 will give rise to a 2D brightness pattern of the type 876, and together they form a rather complicated brightness pattern. Realizing that the encoding of the rings is done by making it luminous (1) or "anti-luminous" (0), the resulting phase-only filtered knot patterns begin to take on subtle characteristics which no longer make direct sense to the human eye, but which are still readily discernable to a computer especially after the phase-only filtering is inverse filtered reproducing the original rings patterns.

Returning now to FIG. 19, we can imagine that an 8-bit identification word has been encoded on the knot patterns and the knot patterns phase-only filtered. The resulting brightness distribution would be a rich tapestry of overlapping wave patterns which would have a certain beauty, but would not be readily intelligible to the eye/brain. [An exception to this might draw from the lore of the South Pacific Island communities, where it is said that sea travellers have learned the subtle art of reading small and multiply complex ocean wave patterns, generated by diffracted and reflected ocean waves off of intervening islands, as a primary navigational tool.] For want of a better term, the resulting mosaic of filtered knot patterns (derived from 866) can be called the encoded knot tapestry or just the knot tapestry. Some basic properties of this knot tapestry are that it retains the basic rotational symmetry of its generator mosaic, it is generally unintelligible to the eye/brain, thus raising it a notch on the sophistication level of reverse engineering, it is more efficient at using the available information content of a grid of pixels (more on this in the next section), and if the basic knot concepts 854 and 864 are utilized, it will not give rise to local "hot spots" where the signal level becomes unduly condensed and hence objectionably visible to a viewer.

The basic decoding process previously described would now need the additional step of inverse filtering the phase-only filter used in the encoding process. This inverse filtering is quite well known in the image processing industry. Provided that the scale of the knot patterns are known a priori, the inverse filtering is straightforward. If on the other hand the scale of the knot patterns is not known, then an additional step of discovering this scale is in order. One such method of discovering the scale of the knot patterns is to iteratively apply the inverse phase-only filter to variously scaled version of an image being decoded, searching for which scale-version begins to exhibit noticeable knot patterning. A common search algorithm such as the simplex method could be used in order to accurately discover the scale of the patterns. The field of object recognition should also be consulted, under the general topic of unknown-scale object detection.

An additional point about the efficiency with which the knot tapestry covers the image pixel grid is in order. Most applications of the knot tapestry method of universal image coding will posit the application of the fully encoded tapestry (i.e. the tapestry which has the N-bit identification word embedded) at a relative low brightness level into the source image. In real terms, the brightness scale of the encoded tapestry will vary from, for example, −5 grey scale values to 5 grey scale values in a typical 256 grey scale image, where the preponderance of values will be within −2 and 2. This brings up the purely practical matter that the knot tapestry will be subject to appreciable bit truncation error. Put as an example, imagine a constructed knot tapestry nicely utilizing a full 256 grey level image, then scaling this down by a factor of 20 in brightness including the bit truncation step, then rescaling this truncated version back up in brightness by the same factor of 20, then inverse phase-only filtering the resultant. The resulting knot pattern mosaic will be a noticeably degraded version of the original knot pattern mosaic. The point of bringing all of this up is the following: it will be a simply defined, but indeed challenging, engineering task to select the various free parameters of design in the implementation of the knot tapestry method, the end goal being to pass a maximum amount of information about the N-bit identification word within some pre-defined visibility tolerance of the knot tapestry. The free parameters include but would not be fully limited to: the radius of the elemental ring in pixels, N or the number of rings, the distance in pixels from the center of a knot pattern to the center of an elemental ring, the packing criteria and distances of one knot pattern with the others, the rules for strand weaving, and the forms and types of phase-only filters to be used on the knot mosaics. It would be desirable to feed such parameters into a computer optimization routine which could assist in their selection. Even this would begin surely as more of an art than a science due to the many non-linear free parameters involved.

A side note on the use of phase-only filtering is that it can assist in the detection of the ring patterns. It does so in that the inverse filtering of the decoding process tends to "blur" the underlying source image upon which the knot tapestry is added, while at the same time "bringing into focus" the ring patterns. Without the blurring of the source image, the emerging ring patterns would have a harder time "competing" with the sharp features of typical images. The decoding procedure should also utilize the gradient thresholding method described in another section. Briefly, this is the method where if it is known that a source signal is much larger in brightness than our signature signals, then an image being decoded can have higher gradient areas thresholded in the service of increasing the signal level of the signature signals relative to the source signal.

As for the other practical difficulty mentioned earlier, item (5) which deals with the relative computational overhead of the 2D FFT routine and of typical pattern recognition routines, the first remedy here posited but not filled is to find a simpler way of quickly recognizing and decoding the polarity of the ring brightnesses than that of using the 2D FFT. Barring this, it can be seen that if the pixel extent of an individual knot pattern (850 or 852) is, for example, 50 pixels in diameter, than a simple 64 by 64 pixel 2D FFT on some section of an image may be more than sufficient to discern the N-bit identification word as previously described. The idea would be to use the smallest image region necessary, as opposed to being required to utilize an entire image, to discern the N-bit identification word.

Another note is that those practitioners in the science of image processing will recognize that instead of beginning the discussion on the knot tapestry with the utilization of rings, we could have instead jumped right to the use of 2D brightness distribution patterns 876, QUA bases functions. The use of the "ring" terminology as the baseline invention is partly didactic, as is appropriate for patent disclosures in any event. What is more important, perhaps, is that the use of true "rings" in the decoding process, post-inverse filtering, is probably the simplest form to input into typical pattern recognition routines.

Neural Network Decoders

Those skilled in the signal processing art will recognize that computers employing neural network architectures are well suited to the pattern recognition and detection-of-small-signal-in-noise issues posed by the present invention. While a complete discourse on these topics is beyond the scope of this specification, the interested reader is referred to, e.g., Cherkassky, V., "*From Statistics to Neural Networks: Theory & Pattern Recognition Applications,*" Springer-Verlag, 1994; Masters, T., "*Signal & Image Processing with Neural Networks: C Sourcebook,*" Wiley, 1994; Guyon, I, "*Advances in Pattern Recognition Systems Using Neural Networks,*" World Scientific Publishers, 1994; Nigrin, A., "*Neural Networks for Pattern Recognition,*" MIT Press, 1993; Cichoki, A., "*Neural Networks for Optimization & Signal Processing,*" Wiley, 1993; and Chen, C., "*Neural Networks for Pattern Recognition & Their Applications,*" World Scientic Publishers, 1991.

2D Universal Codes II: Simple Scan Line Implementation of the One Dimensional Case The above section on rings, knots and tapestries certainly has its beauty, but some of the steps involved may have enough complexity that practical implementations may be too costly for certain applications. A poor cousin the concept of rings and well-designed symmetry is to simply utilize the basic concepts presented in connection with FIG. 9 and the audio signal, and apply them to two dimensional signals such as images, but to do so in a manner where, for example, each scan line in an image has a random starting point on, for example, a 1000 pixel long universal noise signal. It would then be incumbent upon recognition software and hardware to interrogate imagery across the full range of rotational states and scale factors to "find" the existence of these universal codes.

The Universal Commercial Copyright (UCC) Image, Audio, and Video File Formats

It is as well known as it is regretted that there exist a plethora of file format standards (and not-so-standards) for digital images, digital audio, and digital video. These standards have generally been formed within specific industries and applications, and as the usage and exchange of creative digital material proliferated, the various file formats slugged it out in cross-disciplinary arenas, where today we find a defacto histogram of devotees and users of the various favorite formats. The JPEG, MPEG standards for formatting and compression are only slight exceptions it would seem, where some concerted cross-industry collaboration came into play.

The cry for a simple universal standard file format for audio/visual data is as old as the hills. The cry for the protection of such material is older still. With all due respect to the innate difficulties attendant upon the creation of a universal format, and with all due respect to the pretentiousness of outlining such a plan within a patent disclosure, the inventor does believe that the methods of this invention can serve perhaps as well as anything for being the foundation upon which an accepted world-wide "universal commercial copyright" format is built. Practitioners know that such animals are not built by proclamation, but through the efficient meeting of broad needs, tenacity, and luck. More germane to the purposes of this disclosure is the fact that the application of this invention would benefit if it could become a central piece within an industry standard file format. The use of universal codes in particular could be specified within such a standard.

The fullest expression of the commercial usage of this invention comes from the knowledge that the invisible signing is taking place and the confidence that instills in copyright holders.

The following is a list of reasons that the principles of this invention could serve as the catalyst for such a standard: (1) Few if any technical developments have so isolated and so pointedly addressed the issue of broad-brush protection of empirical data and audio/visual material; (2) All previous file formats have treated the information about the data, and the data itself, as two separate and physically distinct entities, whereas the methods of this invention can combine the two into one physical entity; (3) The mass scale application of the principles of this invention will require substantial standardization work in the first place, including integration with the years-to-come improvements in compression technologies, so the standards infrastructure will exist by default; (4) the growth of multimedia has created a generic class of data called "content," which includes text, images, sound, and graphics, arguing for higher and higher levels of "content standards"; and (5) marrying copyright protection technology and security features directly into a file format standard is long overdue.

Elements of a universal standard would certainly include the mirroring aspects of the header verification methods, where header information is verified by signature codes directly within data. Also, a universal standard would outline how hybrid uses of fully private codes and public codes would commingle. Thus, if the public codes were "stripped" by sophisticated pirates, the private codes would remain intact. A universal standard would specify how invisible signatures would evolve as digital images and audio evolve. Thus, when a given image is created based on several source images, the standard would specify how and when the old signatures would be removed and replaced by new signatures, and if the header would keep track of these evolutions and if the signatures themselves would keep some kind of record.

Pixels vs. Bumps

Most of the disclosure focuses on pixels being the basic carriers of the N-bit identification word. The section discussing the use of a single "master code signal" went so far as to essentially "assign" each and every pixel to a unique bit plane in the N-bit identification word.

For many applications, with one exemplar being that of ink based printing at 300 dots per inch resolution, what was once a pixel in a pristine digital image file becomes effectively a blob (e.g. of dithered ink on a piece of paper). Often the isolated information carrying capacity of the original pixel becomes compromised by neighboring pixels spilling over into the geometrically defined space of the original pixel. Those practiced in the art will recognize this as simple spatial filtering and various forms of blurring.

In such circumstances it may be more advantageous to assign a certain highly local group of pixels to a unique bit plane in the N-bit identification word, rather than merely a single pixel. The end goal is simply to pre-concentrate more of the signature signal energy into the lower frequencies, realizing that most practical implementations quickly strip or mitigate higher frequencies.

Figure 21A:
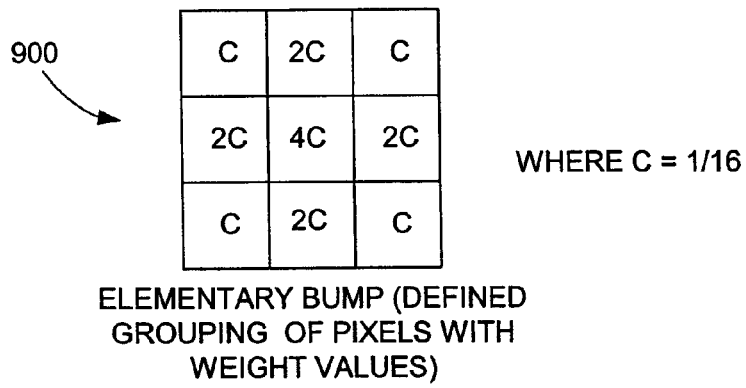
FIG. 21A shows encoding 'bumps' rather than pixels.
Figure 21B:
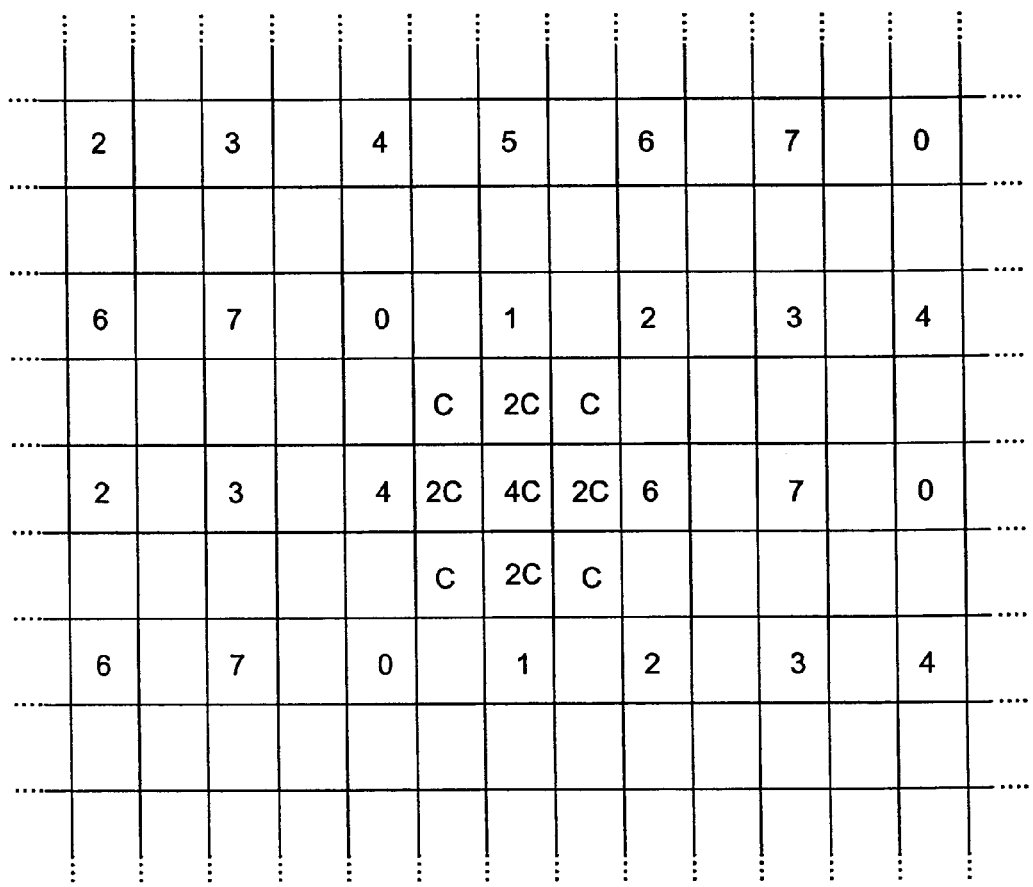
FIG. 21B shows at least an example of how many elementary bumps, 900, would be assigned locations in an image.

A simple-minded approach would be to assign a 2 by 2 block of pixels all to be modulated with the same ultimate signature grey value, rather than modulating a single assigned pixel. A more fancy approach is depicted in FIG. 21, where an array of pixel groups is depicted. This is a specific example of a large class of configurations. The idea is that now a certain small region of pixels is associated with a given unique bit plane in the N-bit identification word, and that this grouping actually shares pixels between bit planes (though it doesn't necessary have to share pixels, as in the case of a 2×2 block of pixels above).

Depicted in FIG. 21 is a 3×3 array of pixels with an example normalized weighting (normalized-->the weights add up to 1). The methods of this invention now operate on this elementary "bump," as a unit, rather than on a single pixel. It can be seen that in this example there is a fourfold decrease in the number of master code values that need to be stored, due to the spreading out of the signature signal. Applications of this "bump approach" to placing in invisible signatures include any application which will experience a priori known high amounts of blurring, where proper identification is still desired even after this heavy blurring.

More on the Steganographic Uses of this Invention

As mentioned in the initial sections of the disclosure, steganography as an art and as a science is a generic prior art to this invention. Putting the shoe on the other foot now, and as already doubtless apparent to the reader who has ventured thus far, the methods of this invention can be used as a novel method for performing steganography. (Indeed, all of the discussion thus far may be regarded as exploring various forms and implementations of steganography.)

In the present section, we shall consider steganography as the need to pass a message from point A to point B, where that message is essentially hidden within generally independent empirical data. As anyone in the industry of telecommunications can attest to, the range of purposes for passing messages is quite broad. Presumably there would be some extra need, beyond pure hobby, to place messages into empirical data and empirical signals, rather than sending those messages via any number of conventional and straightforward channels. Past literature and product propaganda within steganography posits that such an extra need, among others, might be the desire to hide the fact that a message is even being sent. Another possible need is that a conventional communications channel is not available directly or is cost prohibitive, assuming, that is, that a sender of messages can "transmit" their encoded empirical data somehow. This disclosure includes by reference all previous discussions on the myriad uses to which steganography might apply, while adding the following uses which the inventor has not previously seen described.

The first such use is very simple. It is the need to carry messages about the empirical data within which the message is carried. The little joke is that now the media is truly the message, though it would be next to impossible that some previous steganographer hasn't already exploited this joke. Some of the discussion on placing information about the empirical data directly inside that empirical data was already covered in the section on replacing the header and the concept of the "bodier." This section expands upon that section somewhat.

The advantages of placing a message about empirical data directly in that data is that now only one class of data object is present rather than the previous two classes. In any two class system, there is the risk of the two classes becoming disassociated, or one class corrupted without the other knowing about it. A concrete example here is what the inventor refers to as "device independent instructions."

There exist zillions of machine data formats and data file formats. This plethora of formats has been notorious in its power to impede progress toward universal data exchange and having one machine do the same thing that another machine can do. The instructions that an originator might put into a second class of data (say the header) may not at all be compatible with a machine which is intended to recognize these instructions. If format conversions have taken place, it is also possible that critical instructions have been stripped along the way, or garbled. The improvements disclosed here can be used as a way to "seal in" certain instructions directly into empirical data in such a way that all that is needed by a reading machine to recognize instructions and messages is to perform a standardized "recognition algorithm" on the empirical data (providing of course that the machine can at the very least "read" the empirical data properly). All machines could implement this algorithm any old way they choose, using any compilers or internal data formats that they want.

Implementation of this device independent instruction method would generally not be concerned over the issue of piracy or illicit removal of the sealed in messages. Presumably, the embedded messages and instructions would be a central valuable component in the basic value and functioning of the material.

Another example of a kind of steganographic use of the invention is the embedding of universal use codes for the benefit of a user community. The "message" being passed could be simply a registered serial number identifying ownership to users who wish to legitimately use and pay for the empirical information. The serial number could index into a vast registry of creative property, containing the name or names of the owners, pricing information, billing information, and the like. The "message" could also be the clearance of free and public use for some given material. Similar ownership identification and use indexing can be achieved in two class data structure methods such as a header, but the use of the single class system of this invention may offer certain advantages over the two class system in that the single class system does not care about file format conversion, header compatibilities, internal data format issues, header/body archiving issues, and media transformations.

Fully Exact Steganography

Prior art steganographic methods currently known to the inventor generally involve fully deterministic or "exact" prescriptions for passing a message. Another way to say this is that it is a basic assumption that for a given message to be passed correctly in its entirety, the receiver of the information needs to receive the exact digital data file sent by the sender, tolerating no bit errors or "loss" of data. By definition, "lossy" compression and decompression on empirical signals defeat such steganographic methods. (Prior art, such as the previously noted Komatsu work, are the exceptions here.)

The principles of this invention can also be utilized as an exact form of steganography proper. It is suggested that such exact forms of steganography, whether those of prior art or those of this invention, be combined with the relatively recent art of the "digital signature" and/or the DSS (digital signature standard) in such a way that a receiver of a given empirical data file can first verify that not one single bit of information has been altered in the received file, and thus verify that the contained exact steganographic message has not been altered.

The simplest way to use the principles of this invention in an exact steganographic system is to utilize the previously discussed "designed" master noise scheme wherein the master snowy code is not allowed to contain zeros. Both a sender and a receiver of information would need access to BOTH the master snowy code signal AND the original unencoded original signal. The receiver of the encoded signal merely subtracts the original signal giving the difference signal and the techniques of simple polarity checking between the difference signal and the master snowy code signal, data sample to data sample, producing a the passed message a single bit at a time. Presumably data samples with values near the "rails" of the grey value range would be skipped (such as the values 0, 1, 254 and 255 in 8-bit depth empirical data).

Statistical Steganography

The need for the receiver of a steganographic embedded data file to have access to the original signal can be removed by turning to what the inventor refers to as "statistical steganography." In this approach, the methods of this invention are applied as simple a priori rules governing the reading of an empirical data set searching for an embedded message. This method also could make good use of it combination with prior art methods of verifying the integrity of a data file, such as with the DSS. (See, e.g., Walton, "Image Authentication for a Slippery New Age," Dr. Dobb's Journal, April, 1995, p. 18 for methods of verifying the sample-by-sample, bit-by-bit, integrity of a digital image.)

Statistical steganography posits that a sender and receiver both have access to the same master snowy code signal. This signal can be entirely random and securely transmitted to both parties, or generated by a shared and securely transmitted lower order key which generates a larger quasi-random master snowy code signal. It is a priori defined that 16 bit chunks of a message will be passed within contiguous 1024 sample blocks of empirical data, and that the receiver will use dot product decoding methods as outlined in this disclosure. The sender of the information pre-checks that the dot product approach indeed produces the accurate 16 bit values (that is, the sender pre-checks that the cross-talk between the carrier image and the message signal is not such that the dot product operation will produce an unwanted inversion of any of the 16 bits). Some fixed number of 1024 sample blocks are transmitted and the same number times 16 bits of message is therefore transmitted. DSS techniques can be used to verify the integrity of a message when the transmitted data is known to only exist in digital form, whereas internal checksum and error correcting codes can be transmitted in situations where the data may be subject to change and transformation in its transmission. In this latter case, it is best to have longer blocks of samples for any given message content size (such as 10K samples for a 16 bit message chunk, purely as an example).

The "Noise" in Vector Graphics and Very-Low-Order Indexed Graphics

The methods of this disclosure generally posit the existence of "empirical signals," which is another way of saying signals which have noise contained within them almost by definition. There are two classes of 2 dimensional graphics which are not generally considered to have noise inherent in them: vector graphics and certain indexed bit-mapped graphics. Vector graphics and vector graphic files are generally files which contain exact instructions for how a computer or printer draws lines, curves and shapes. A change of even one bit value in such a file might change a circle to a square, as a very crude example. In other words, there is generally no "inherent noise" to exploit within these files. Indexed bit-mapped graphics refers to images which are composed of generally a small number of colors or grey values, such as 16 in the early CGA displays on PC computers. Such "very-low-order" bit-mapped images usually display graphics and cartoons, rather than being used in the attempted display of a digital image taken with a camera of the natural world. These types of very-low-order bit-mapped graphics also are generally not considered to contain "noise" in the classic sense of that term. The exception is where indexed graphic files do indeed attempt to depict natural imagery, such as with the GIF (graphic interchange format of Compuserve), where the concept of "noise" is still quite valid and the principles of this invention still quite valid. These latter forms often use dithering (similar to pointillist paintings and color newspaper print) to achieve near lifelike imagery.

This section concerns this class of 2 dimensional graphics which traditionally do not contain "noise." This section takes a brief look at how the principles of this invention can still be applied in some fashion to such creative material.

The easiest way to apply the principles of this invention to these "noiseless" graphics is to convert them into a form which is amenable to the application of the principles of this invention. Many terms have been used in the industry for this conversion, including "ripping" a vector graphic (raster image processing) such that a vector graphic file is converted to a greyscale pixel-based raster image. Programs such as Photoshop by Adobe have such internal tools to convert vector graphic files into RGB or greyscale digital images. Once these files are in such a form, the principles of this invention can be applied in a straightforward manner. Likewise, very-low-indexed bitmaps can be converted to an RGB digital image or an equivalent. In the RGB domain, the signatures can be applied to the three color channels in appropriate ratios, or the RGB image can be simply converted into a greyscale/chroma format such as "Lab" in Photoshop, and the signatures can be applied to the "Lightness channel" therein. Since most of the distribution media, such as videotapes, CD-ROMs, MPEG video, digital images, and print are all in forms which are amenable to the application of the principles of this invention, this conversion from vector graphic form and very-low-order graphic form is often done in any event.

Another way to apply the principles of this invention to vector graphics and very-low-order bitmapped graphics is to recognize that, indeed, there are certain properties to these inherent graphic formats which—to the eye—appear as noise. The primary example is the borders and contours between where a given line or figure is drawn or not drawn, or exactly where a bit-map changes from green to blue. In most cases, a human viewer of such graphics will be keenly aware of any attempts to "modulate signature signals" via the detailed and methodical changing of the precise contours of a graphic object. Nevertheless, such encoding of the signatures is indeed possible. The distinction between this approach and that disclosed in the bulk of this disclosure is that now the signatures must ultimately derive from what already exists in a given graphic, rather than being purely and separately created and added into a signal. This disclosure points out the possibilities here nonetheless. The basic idea is to modulate a contour, a touch right or a touch left, a touch up or a touch down, in such a way as to communicate an N-bit identification word. The locations of the changes contours would be contained in a an analogous master noise image, though now the noise would be a record of random spatial shifts one direction or another, perpendicular to a given contour. Bit values of the N-bit identification word would be encoded, and read, using the same polarity checking method between the applied change and the change recorded in the master noise image.

Plastic Credit and Debit Card Systems Based on the Principles of the Invention

Growth in the use of plastic credit cards, and more recently debit cards and ATM cash cards, needs little introduction. Nor does there need to be much discussion here about the long history of fraud and illicit uses of these financial instruments. The development of the credit card hologram, and its subsequent forgery development, nicely serves as a historic example of the give and take of plastic card security measures and fraudulent countermeasures. This section will concern itself with how the principles of this invention can be realized in an alternative, highly fraud-proof yet cost effective plastic card-based financial network.

A basic list of desired features for an ubiquitous plastic economy might be as follows: 1) A given plastic financial card is completely impossible to forge; 2) An attempted forged card (a "look-alike") cannot even function within a transaction setting; 3) Intercepted electronic transactions by a would-be thief would not in any way be useful or re-useable; 4) In the event of physical theft of an actual valid card, there are still formidable obstacles to a thief using that card; and 5) The overall economic cost of implementation of the financial card network is equal to or less than that of the current international credit card networks, i.e., the fully loaded cost per transaction is equal to or less than the current norm, allowing for higher profit margins to the implementors of the networks. Apart from item 5, which would require a detailed analysis of the engineering and social issues involved with an all out implementation strategy, the following use of the principles of this invention may well achieve the above list, even item 5.

Figure 26:
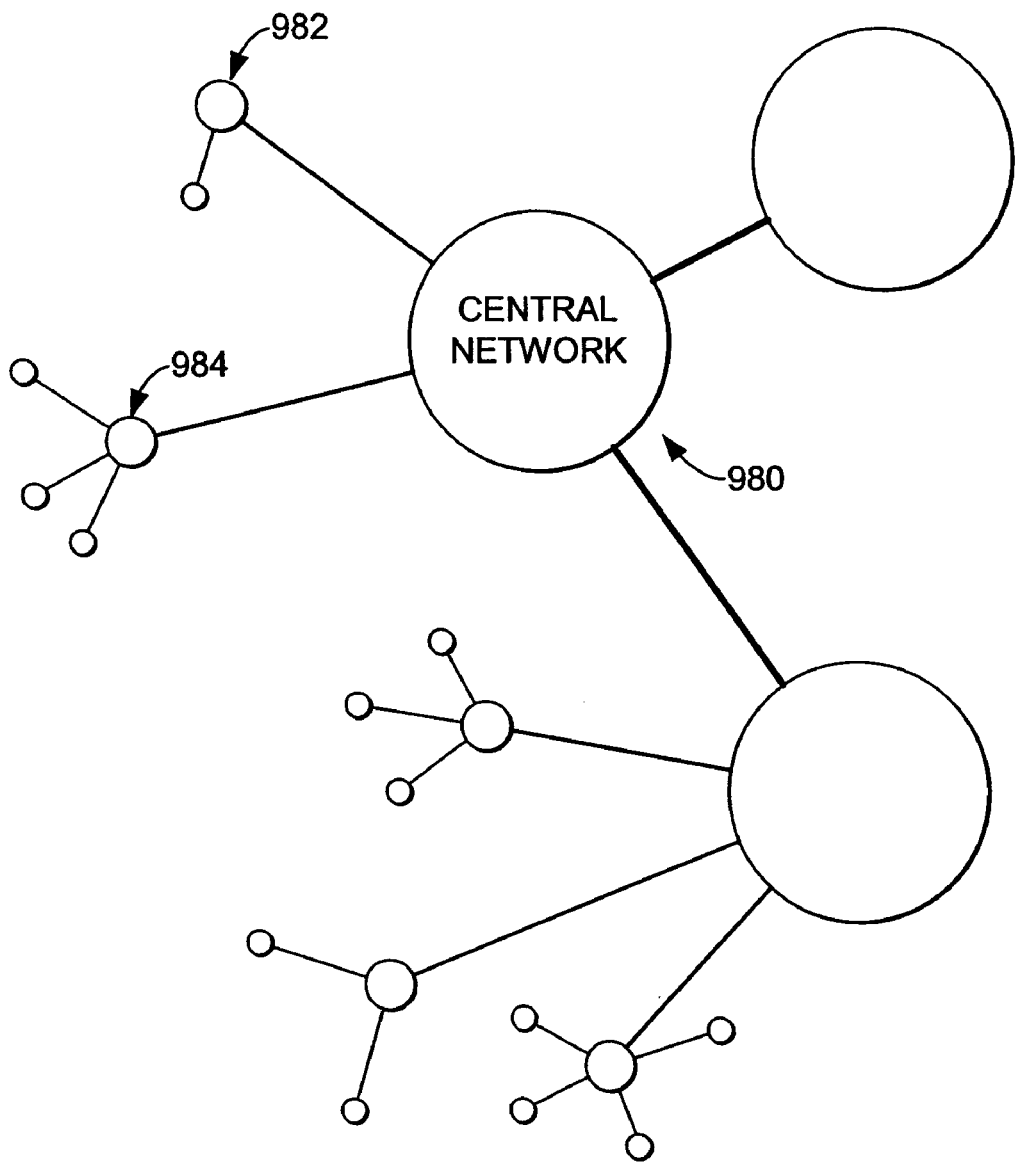

FIGS. 22 through 26, along with the ensuing written material, collectively outline what is referred to in FIG. 26 as "The Negligible-Fraud Cash Card System." The reason that the fraud-prevention aspects of the system are highlighted in the title is that fraud, and the concomitant lost revenue therefrom, is apparently a central problem in today's plastic card based economies. The differential advantages and disadvantages of this system relative to current systems will be discussed after a preferred embodiment is presented.

Figure 22:
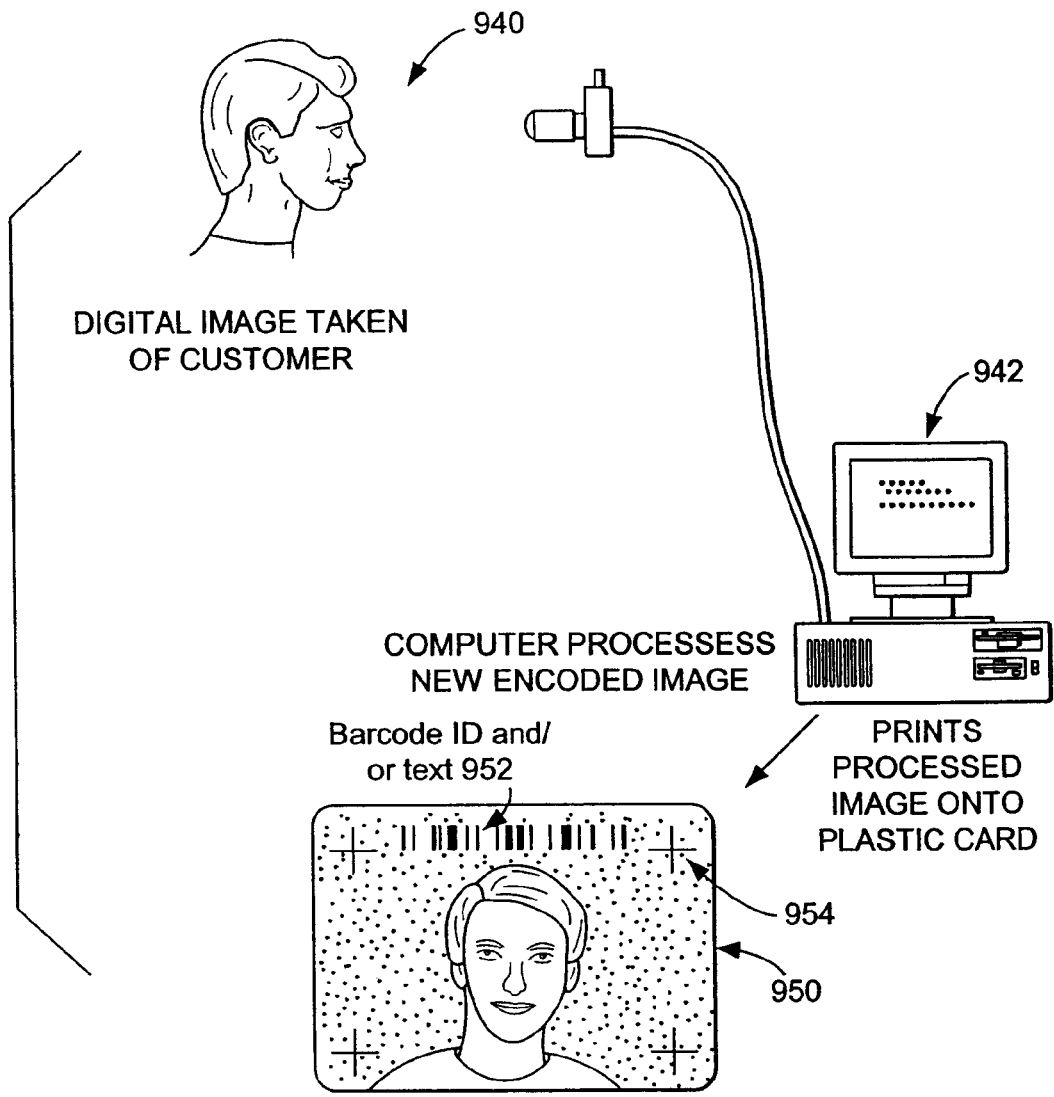

FIG. 22 illustrates the basic unforgeable plastic card which is quite unique to each and every user. A digital image 940 is taken of the user of the card. A computer, which is hooked into the central accounting network, 980, depicted in FIG. 26, receives the digital image 940, and after processing it (as will be described surrounding FIG. 24) produces a final rendered image which is then printed out onto the personal cash card 950. Also depicted in FIG. 22 is a straightforward identification marking, in this case a bar code 952, and optional position fiducials which may assist in simplifying the scanning tolerances on the Reader 958 depicted in FIG. 23.

The short story is that the personal cash card 950 actually contains a very large amount of information unique to that particular card. There are no magnetic strips involved, though the same principles can certainly be applied to magnetic strips, such as an implanted magnetic noise signal (see earlier discussion on the "fingerprinting" of magnetic strips in credit cards; here, the fingerprinting would be prominent and pro-active as opposed to passive). In any event, the unique information within the image on the personal cash card 950 is stored along with the basic account information in a central accounting network, 980, FIG. 26. The basis for unbreakable security is that during transactions, the central network need only query a small fraction of the total information contained on the card, and never needs to query the same precise information on any two transactions. Hundreds if not thousands or even tens of thousands of unique and secure "transaction tokens" are contained within a single personal cash card. Would-be pirates who went so far as to pick off transmissions of either encrypted or even unencrypted transactions would find the information useless thereafter. This is in marked distinction to systems which have a single complex and complete "key" (generally encrypted) which needs to be accessed, in its entirety, over and over again. The personal cash card on the other hand contains thousands of separate and secure keys which can be used once, within milliseconds of time, then forever thrown away (as it were). The central network 980 keeps track of the keys and knows which have been used and which haven't.

Figure 23:
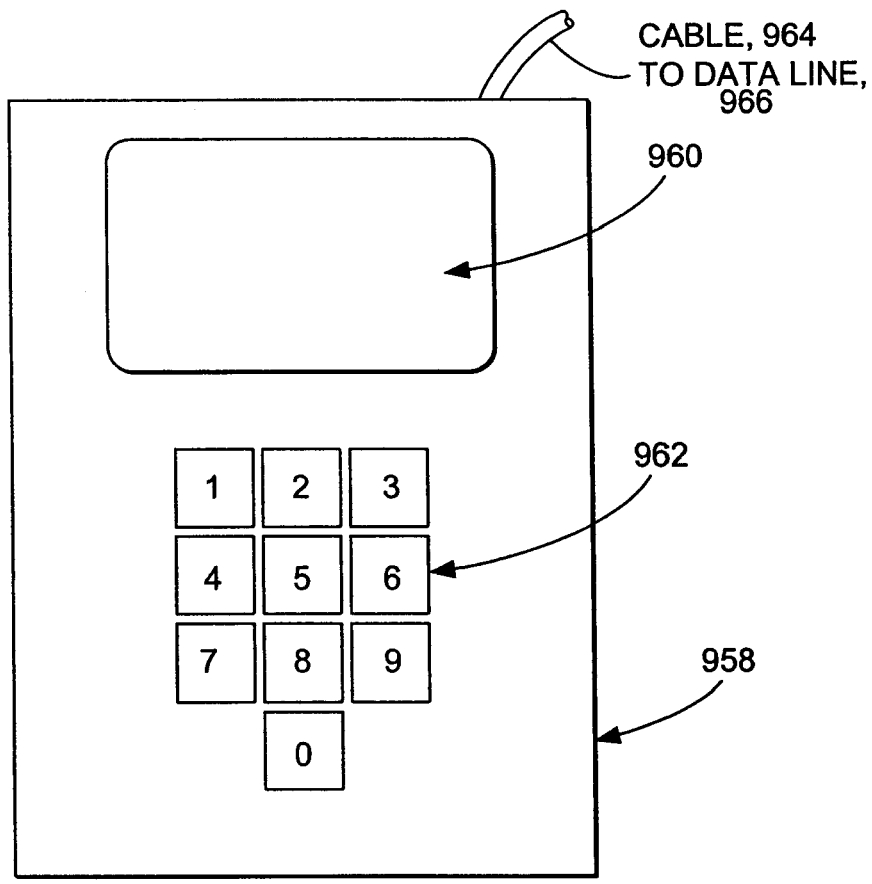

FIG. 23 depicts what a typical point-of-sale reading device, 958, might look like. Clearly, such a device would need to be manufacturable at costs well in line with, or cheaper than, current cash register systems, ATM systems, and credit card swipers. Not depicted in FIG. 23 are the innards of the optical scanning, image processing, and data communications components, which would simply follow normal engineering design methods carrying out the functions that are to be described henceforth and are well within the capability of artisans in these fields. The reader 958 has a numeric punch pad 962 on it, showing that a normal personal identification number system can be combined with the overall design of this system adding one more conventional layer of security (generally after a theft of the physical card has occurred). It should also be pointed out that the use of the picture of the user is another strong (and increasingly common) security feature intended to thwart after-theft and illicit use. Functional elements such as the optical window, 960, are shown, mimicking the shape of the card, doubling as a centering mechanism for the scanning. Also shown is the data line cable 966 presumably connected either to a proprietor's central merchant computer system or possibly directly to the central network 980. Such a reader may also be attached directly to a cash register which performs the usual tallying of purchased items. Perhaps overkill on security would be the construction of the reader, 958, as a type of Faraday cage such that no electronic signals, such as the raw scan of the card, can emanate from the unit. The reader 958 does need to contain, preferably, digital signal processing units which will assist in swiftly calculating the dot product operations described henceforth. It also should contain local read-only memory which stores a multitude of spatial patterns (the orthogonal patterns) which will be utilized in the "recognition" steps outlined in FIG. 25 and its discussion. As related in FIG. 23, a consumer using the plastic card merely places their card on the window to pay for a transaction. A user could choose for themselves if they want to use a PIN number or not. Approval of the purchase would presumably happen within seconds, provided that the signal processing steps of FIG. 25 are properly implemented with effectively parallel digital processing hardware.

Figure 24:
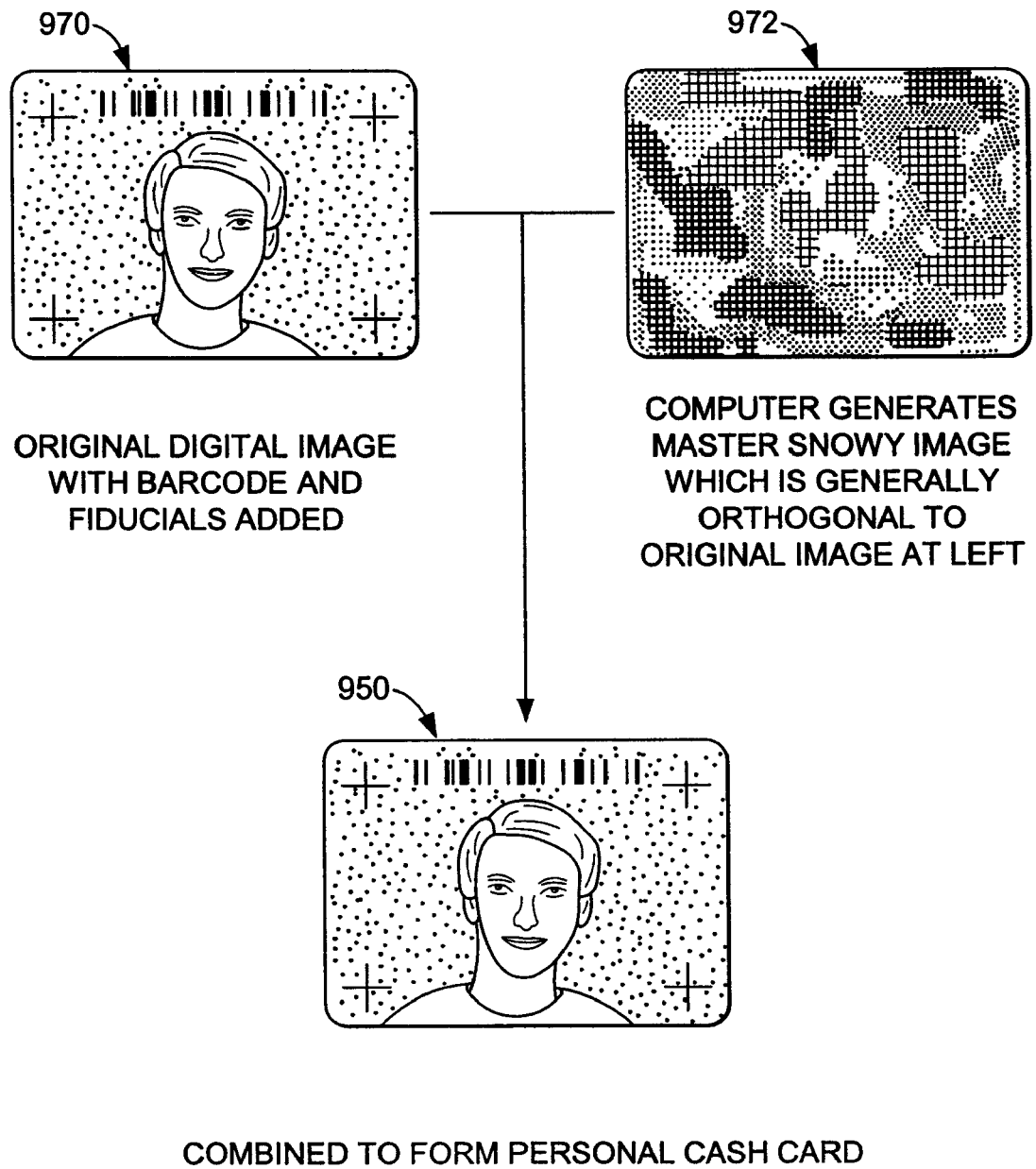

FIG. 24 takes a brief look at one way to process the raw digital image, 940, of a user into an image with more useful information content and uniqueness. It should be clearly pointed out that the raw digital image itself could in fact be used in the following methods, but that placing in additional orthogonal patterns into the image can significantly increase the overall system. (Orthogonal means that, if a given pattern is multiplied by another orthogonal pattern, the resulting number is zero, where "multiplication of patterns" is meant in the sense of vector dot products; these are all familiar terms and concepts in the art of digital image processing). FIG. 24 shows that the computer 942 can, after interrogating the raw image 970, generate a master snowy image 972 which can be added to the raw image 970 to produce a yet-more unique image which is the image that is printed onto the actual personal cash card, 950. The overall effect on the image is to "texturize" the image. In the case of a cash card, invisibility of the master snowy pattern is not as much of a requirement as with commercial imagery, and one of the only criteria for keeping the master snowy image somewhat lighter is to not obscure the image of the user. The central network, 980, stores the final processed image in the record of the account of the user, and it is this unique and securely kept image which is the carrier of the highly secure "throw-away transaction keys." This image will therefore be "made available" to all duly connected point-of-sale locations in the overall network. As will be seen, none of the point-of-sale locations ever has knowledge of this image, they merely answer queries from the central network.

FIG. 25 steps through a typical transaction sequence. The figure is laid out via indentations, where the first column are steps performed by the point-of-sale reading device 958, the second column has information transmission steps communicated over the data line 966, and the third column has steps taken by the central network 980 which has the secured information about the user's account and the user's unique personal cash card 950. Though there is some parallelism possible in the implementation of the steps, as is normally practiced in the engineering implementation of such systems, the steps are nevertheless laid out according to a general linear sequence of events.

Step one of FIG. 25 is the standard "scanning" of a personal cash card 950 within the optical window 960. This can be performed using linear optical sensors which scan the window, or via a two dimensional optical detector array such as a CCD. The resulting scan is digitized into a grey scale image and stored in an image frame memory buffer such as a "framegrabber," as is now common in the designs of optical imaging systems. Once the card is scanned, a first image processing step would probably be locating the four fiducial center points, 954, and using these four points to guide all further image processing operations (i.e. the four fiducials "register" the corresponding patterns and barcodes on the personal cash card). Next, the barcode ID number would be extracted using common barcode reading image processing methods. Generally, the user's account number would be determined in this step.

Step two of FIG. 25 is the optional typing in of the PIN number. Presumably most users would opt to have this feature, except those users who have a hard time remembering such things and who are convinced that no one will ever steal their cash card.

Step three of FIG. 25 entails connecting through a data line to the central accounting network and doing the usual communications handshaking as is common in modem-based communications systems. The preferred embodiment of this system would obviate the need for standard phone lines, such as the use of optical fiber data links, but for now we can assume it is a garden variety belltone phone line and that the reader 958 hasn't forgotten the phone number of the central network.

After basic communications are established, step four shows that the point-of-sale location transmits the ID number found in step 1, along with probably an encrypted version of the PIN number (for added security, such as using the ever more ubiquitous RSA encryption methods), and appends the basic information on the merchant who operates the point-of-sale reader 958, and the amount of the requested transaction in monetary units.

Step five has the central network reading the ID number, routing the information accordingly to the actual memory location of that user's account, thereafter verifying the PIN number and checking that the account balance is sufficient to cover the transaction. Along the way, the central network also accesses the merchant's account, checks that it is valid, and readies it for an anticipated credit.

Step six begins with the assumption that step five passed all counts. If step five didn't, the exit step of sending a NOT OK back to the merchant is not depicted. So, if everything checks out, the central network generates twenty four sets of sixteen numbers, where all numbers are mutually exclusive, and in general, there will be a large but quite definitely finite range of numbers to choose from. FIG. 25 posits the range being 64K or 65536 numbers. It can be any practical number, actually. Thus, set one of the twenty four sets might have the numbers 23199, 54142, 11007, 2854, 61932, 32879, 38128, 48107, 65192, 522, 55723, 27833, 19284, 39970, 19307, and 41090, for example. The next set would be similarly random, but the numbers of set one would be off limits now, and so on through the twenty four sets. Thus, the central network would send (16×24×2 bytes) of numbers or 768 bytes. The actual amount of numbers can be determined by engineering optimization of security versus transmission speed issues. These random numbers are actually indexes to a set of 64K universally a priori defined orthogonal patterns which are well known to both the central network and are permanently stored in memory in all of the point-of-sale readers. As will be seen, a would-be thief's knowledge of these patterns is of no use.

Step seven then transmits the basic "OK to proceed" message to the reader, 958, and also sends the 24 sets of 16 random index numbers.

Step eight has the reader receiving and storing all these numbers. Then the reader, using its local microprocessor and custom designed high speed digital signal processing circuitry, steps through all twenty four sets of numbers with the intention of deriving 24 distinct floating point numbers which it will send back to the central network as a "one time key" against which the central network will check the veracity of the card's image. The reader does this by first adding together the sixteen patterns indexed by the sixteen random numbers of a given set, and then performing a common dot product operation between the resulting composite pattern and the scanned image of the card. The dot product generates a single number (which for simplicity we can call a floating point number). The reader steps through all twenty four sets in like fashion, generating a unique string of twenty four floating point numbers.

Step nine then has the reader transmitting these results back to the central network.

Step ten then has the central network performing a check on these returned twenty four numbers, presumably doing its own exact same calculations on the stored image of the card that the central network has in its own memory. The numbers sent by the reader can be "normalized," meaning that the highest absolute value of the collective twenty four dot products can divided by itself (its unsigned value), so that brightness scale issues are removed. The resulting match between the returned values and the central network's calculated values will either be well within given tolerances if the card is valid, and way off if the card is a phony or if the card is a crude reproduction.

Step eleven then has the central network sending word whether or not the transaction was OK, and letting the customer know that they can go home with their purchased goods.

Step twelve then explicitly shows how the merchant's account is credited with the transaction amount.

As already stated, the primary advantage of this plastic card invention is to significantly reduce fraud, which apparently is a large cost to current systems. This system reduces the possibility of fraud only to those cases where the physical card is either stolen or very carefully copied. In both of these cases, there still remains the PIN security and the user picture security (a known higher security than low wage clerks analyzing signatures). Attempts to copy the card must be performed through "temporary theft" of the card, and require photo-quality copying devices, not simple magnetic card swipers. The system is founded upon a modern 24 hour highly linked data network. Illicit monitoring of transactions does the monitoring party no use whether the transmissions are encrypted or not.

Figure 27:
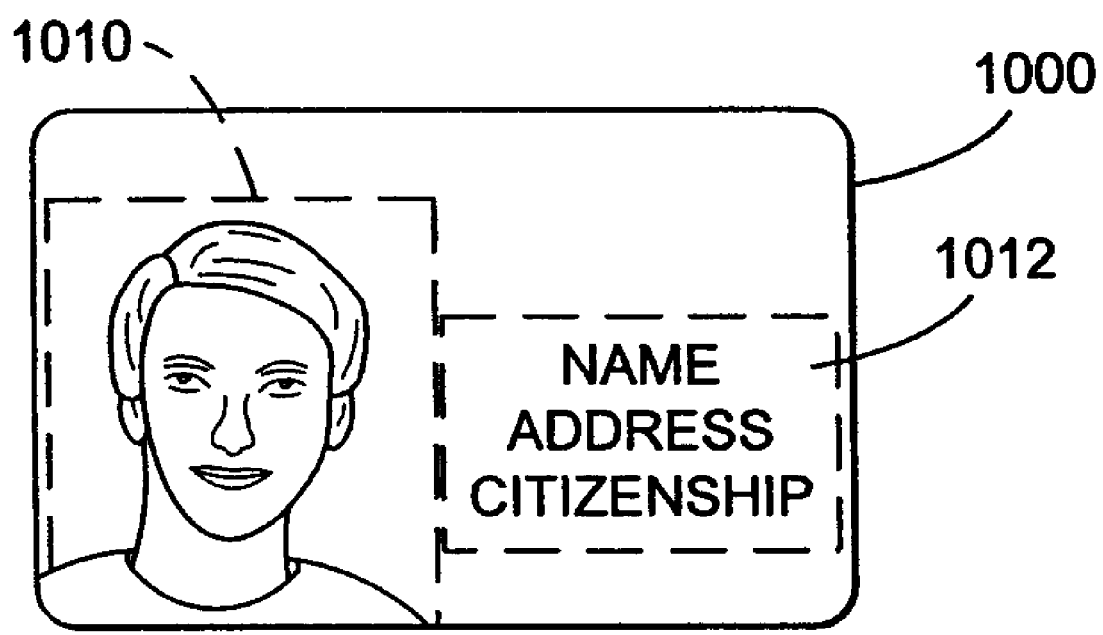
FIG. 27 is a diagram of a photographic identification document or security card with which the security system aspect of the present invention may be applied.

It will be appreciated that the foregoing approach to increasing the security of transactions involving credit and debit card systems is readily extended to any photograph-based identification system. Moreover, the principles of the present invention may be applied to detect alteration of photo ID documents, and to generally enhance the confidence and security of such systems. In this regard, reference is made to FIG. 27, which depicts a photo-ID card or document 1000 which may be, for example, a passport or visa, driver's license, credit card, government employee identification, or a private industry identification badge. For convenience, such photograph-based identification documents will be collectively referred to as photo ID documents.

The photo ID document includes a photograph 1010 that is attached to the document 1000. Printed, human-readable information 1012 is incorporated in the document 1000, adjacent to the photograph 1010. Machine readable information, such as that known as "bar code" may also be included adjacent to the photograph.

Generally, the photo ID document is constructed so that tampering with the document (for example, swapping the original photograph with another) should cause noticeable damage to the card. Nevertheless, skilled forgerers are able to either alter existing documents or manufacture fraudulent photo ID documents in a manner that is extremely difficult to detect.

As noted above, the present invention enhances the security associated with the use of photo ID documents by supplementing the photographic image with encoded information (which information may or may not be visually perceptible), thereby facilitating the correlation of the photographic image with other information concerning the person, such as the printed information 1012 appearing on the document 1000.

In one embodiment of this aspect of the invention, the photograph 1010 may be produced from a raw digital image to which is added a master snowy image as described above in connection with FIGS. 22-24. The above-described central network and point-of-sale reading device (which device, in the present embodiment, may be considered as a point-of-entry or point-of-security photo ID reading device), would essentially carry out the same processing as described with that embodiment, including the central network generation of unique numbers to serve as indices to a set of defined orthogonal patterns, the associated dot product operation carried out by the reader, and the comparison with a similar operation carried out by the central network. If the numbers generated from the dot product operation carried out by the reader and the central network match, in this embodiment, the network sends the OK to the reader, indicating a legitimate or unaltered photo ID document.

In another embodiment of this aspect of the invention, the photograph component 1010 of the identification document 1000 may be digitized and processed so that the photographic image that is incorporated into the photo ID document 1000 corresponds to the "distributable signal" as defined above. In this instance, therefore, the photograph includes a composite, embedded code signal, imperceptible to a viewer, but carrying an N-bit identification code. It will be appreciated that the identification code can be extracted from the photo using any of the decoding techniques described above, and employing either universal or custom codes, depending upon the level of security sought.

It will be appreciated that the information encoded into the photograph may correlate to, or be redundant with, the readable information 1012 appearing on the document. Accordingly, such a document could be authenticated by placing the photo ID document on a scanning system, such as would be available at a passport or visa control point. The local computer, which may be provided with the universal code for extracting the identification information, displays the extracted information on the local computer screen so that the operator is able to confirm the correlation between the encoded information and the readable information 1012 carried on the document.

It will be appreciated that the information encoded with the photograph need not necessarily correlate with other information on an identification document. For example, the scanning system may need only to confirm the existence of the identification code so that the user may be provided with a "go" or "no go" indication of whether the photograph has been tampered with. It will also be appreciated that the local computer, using an encrypted digital communications line, could send a packet of information to a central verification facility, which thereafter returns an encrypted "go" or "no go" indication.

In another embodiment of the present invention, it is contemplated that the identification code embedded in the photograph may be a robust digital image of biometric data, such as a fingerprint of the card bearer, which image, after scanning and display, may be employed for comparison with the actual fingerprint of the bearer in very high security access points where on-the-spot fingerprint recognition systems (or retinal scans, etc.) are employed.

It will be appreciated that the information embedded in the photograph need not be visually hidden or steganographically embedded. For example, the photograph incorporated into the identification card may be a composite of an image of the individual and one-, or two-dimensional bar codes. The bar code information would be subject to conventional optical scanning techniques (including internal cross checks) so that the information derived from the code may be compared, for example, to the information printed on the identification document.

It is also contemplated that the photographs of ID documents currently in use may be processed so that information correlated to the individual whose image appears in the photograph may be embedded. In this regard, the reader's attention is directed to the foregoing portion of this description entitled "Use in Printing, Paper, Documents, Plastic-Coated Identification Cards, and Other Material Where Global Embedded Codes Can Be Imprinted," wherein there is described numerous approaches to modulation of physical media that may be treated as "signals" amenable to application of the present invention principles.

Potential Use of the Invention in the Protection and Control of Software Programs The illicit use, copying, and reselling of software programs represents a huge loss of revenues to the software industry at large. The prior art methods for attempting to mitigate this problem are very broad and will not be discussed here. What will be discussed is how the principles of this invention might be brought to bear on this huge problem. It is entirely unclear whether the tools provided by this invention will have any economic advantage (all things considered) over the existing countermeasures both in place and contemplated.

The state of technology over the last decade or more has made it a general necessity to deliver a full and complete copy of a software program in order for that program to function on a user's computer. In effect, $X were invested in creating a software program where X is large, and the entire fruits of that development must be delivered in its entirety to a user in order for that user to gain value from the software product. Fortunately this is generally compiled code, but the point is that this is a shaky distribution situation looked at in the abstract. The most mundane (and harmless in the minds of most perpetrators) illicit copying and use of the program can be performed rather easily.

This disclosure offers, at first, an abstract approach which may or may not prove to be economical in the broadest sense (where the recovered revenue to cost ratio would exceed that of most competing methods, for example). The approach expands upon the methods and approaches already laid out in the section on plastic credit and debit cards. The abstract concept begins by positing a "large set of unique patterns," unique among themselves, unique to a given product, and unique to a given purchaser of that product. This set of patterns effectively contains thousands and even millions of absolutely unique "secret keys" to use the cryptology vernacular. Importantly and distinctly, these keys are non-deterministic, that is, they do not arise from singular sub-1000 or sub-2000 bit keys such as with the RSA key based systems. This large set of patterns is measured in kilobytes and Megabytes, and as mentioned, is non-deterministic in nature. Furthermore, still at the most abstract level, these patterns are fully capable of being encrypted via standard techniques and analyzed within the encrypted domain, where the analysis is made on only a small portion of the large set of patterns, and that even in the worst case scenario where a would-be pirate is monitoring the step-by-step microcode instructions of a microprocessor, this gathered information would provide no useful information to the would-be pirate. This latter point is an important one when it comes to "implementation security" as opposed to "innate security" as will be briefly discussed below.

So what could be the differential properties of this type of key based system as opposed to, for example, the RSA cryptology methods which are already well respected, relatively simple, etc. etc? As mentioned earlier, this discussion is not going to attempt a commercial side-by-side analysis. Instead, we'll just focus on the differing properties. The main distinguishing features fall out in the implementation realm (the implementation security). One example is that in single lowbit-number private key systems, the mere local use and re-use of a single private key is an inherently weak link in an encrypted transmission system. ["Encrypted transmission systems" are discussed here in the sense that securing the paid-for use of software programs will in this discussion require de facto encrypted communication between a user of the software and the "bank" which allows the user to use the program; it is encryption in the service of electronic financial transactions looked at in another light.] Would-be hackers wishing to defeat so-called secure systems never attack the fundamental hard-wired security (the innate security) of the pristine usage of the methods, they attack the implementation of those methods, centered around human nature and human oversights. It is here, still in the abstract, that the creation of a much larger key base, which is itself non-deterministic in nature, and which is more geared toward effectively throwaway keys, begins to "idiot proof" the more historically vulnerable implementation of a given secure system. The huge set of keys is not even comprehensible to the average holder of those keys, and their use of those keys (i.e., the "implementation" of those keys) can randomly select keys, easily throw them out after a time, and can use them in a way that no "eavesdropper" will gain any useful information in the eavesdropping, especially when well within a millionth of the amount of time that an eavesdropper could "decipher" a key, its usefulness in the system would be long past.

Turning the abstract to the semi-concrete, one possible new approach to securely delivering a software product to ONLY the bonafide purchasers of that product is the following. In a mass economic sense, this new method is entirely founded upon a modest rate realtime digital connectivity (often, but not necessarily standard encrypted) between a user's computer network and the selling company's network. At first glance this smells like trouble to any good marketing person, and indeed, this may throw the baby out with the bathwater if by trying to recover lost revenues, you lose more legitimate revenue along the way (all part of the bottom line analysis). This new method dictates that a company selling a piece of software supplies to anyone who is willing to take it about 99.8% of its functional software for local storage on a user's network (for speed and minimizing transmission needs). This "free core program" is entirely unfunctional and designed so that even the craftiest hackers can't make use of it or "decompile it" in some sense. Legitimate activation and use of this program is performed purely on a instruction-cycle-count basis and purely in a simple very low overhead communications basis between the user's network and the company's network. A customer who wishes to use the product sends payment to the company via any of the dozens of good ways to do so. The customer is sent, via common shipment methods, or via commonly secured encrypted data channels, their "huge set of unique secret keys." If we were to look at this large set as if it were an image, it would look just like the snowy images discussed over and over again in other parts of this disclosure. (Here, the "signature" is the image, rather than being imperceptibly placed onto another image). The special nature of this large set is that it is what we might call "ridiculously unique" and contains a large number of secret keys. (The "ridiculous" comes from the simple math on the number of combinations that are possible with, say 1 Megabyte of random bit values, equaling exactly the number that "all ones" would give, thus 1 Megabyte being approximately 10 raised to the ~2,400,000 power, plenty of room for many people having many throwaway secret keys). It is important to re-emphasize that the purchased entity is literally: productive use of the tool. The marketing of this would need to be very liberal in its allotment of this productivity, since per-use payment schemes notoriously turn off users and can lower overall revenues significantly.

This large set of secret keys is itself encrypted using standard encryption techniques. The basis for relatively higher "implementation security" can now begin to manifest itself. Assume that the user now wishes to use the software product. They fire up the free core, and the free core program finds that the user has installed their large set of unique encrypted keys. The core program calls the company network and does the usual handshaking. The company network, knowing the large set of keys belonging to that bonafide user, sends out a query on some simple set of patterns, almost exactly the same way as described in the section on the debit and credit cards. The query is such a small set of the whole, that the inner workings of the core program do not even need to decrypt the whole set of keys, only certain parts of the keys, thus no decrypted version of the keys ever exist, even within the machine cycles on the local computer itself. As can be seen, this does not require the "signatures within a picture" methods of the main disclosure, instead, the many unique keys ARE the picture. The core program interrogates the keys by performing certain dot products, then sends the dot products back to the company's network for verification. See FIG. 25 and the accompanying discussion for typical details on a verification transaction. Generally encrypted verification is sent, and the core program now "enables" itself to perform a certain amount of instructions, for example, allowing 100,000 characters being typed into a word processing program (before another unique key needs to be transmitted to enable another 100,000). In this example, a purchaser may have bought the number of instructions which are typically used within a one year period by a single user of the word processor program. The purchaser of this product now has no incentive to "copy" the program and give it to their friends and relatives.

All of the above is well and fine except for two simple problems. The first problem can be called "the cloning problem" and the second "the big brother problem." The solutions to these two problems are intimately linked. The latter problem will ultimately become a purely social problem, with certain technical solutions as mere tools not ends.

The cloning problem is the following. It generally applies to a more sophisticated pirate of software rather than the currently common "friend gives their distribution CD to a friend" kind of piracy. Crafty-hacker "A" knows that if she performs a system-state clone of the "enabled" program in its entirety and installs this clone on another machine, then this second machine effectively doubles the value received for the same money. Keeping this clone in digital storage, hacker "A" only needs to recall it and reinstall the clone after the first period is run out, thus indefinitely using the program for a single payment, or she can give the clone to their hacker friend "B" for a six-pack of beer. One good solution to this problem requires, again, a rather well developed and low cost real time digital connectivity between user site and company enabling network. This ubiquitous connectivity generally does not exist today but is fast growing through the Internet and the basic growth in digital bandwidth. Part and parcel of the "enabling" is a negligible communications cost random auditing function wherein the functioning program routinely and irregularly performs handshakes and verifications with the company network. It does so, on average, during a cycle which includes a rather small amount of productivity cycles of the program. The resulting average productivity cycle is in general much less than the raw total cost of the cloning process of the overall enabled program. Thus, even if an enabled program is cloned, the usefulness of that instantaneous clone is highly limited, and it would be much more cost effective to pay the asking price of the selling company than to repeat the cloning process on such short time periods. Hackers could break this system for fun, but certainly not for profit. The flip side to this arrangement is that if a program "calls up" the company's network for a random audit, the allotted productivity count for that user on that program is accounted for, and that in cases where bonafide payment has not been received, the company network simply withholds its verification and the program no longer functions. We're back to where users have no incentive to "give this away" to friends unless it is an explicit gift (which probably is quite appropriate if they have indeed paid for it: "do anything you like with it, you paid for it").

The second problem of "big brother" and the intuitively mysterious "enabling" communications between a user's network and a company's network would as mentioned be a social and perceptual problem that should have all manner of potential real and imagined solutions. Even with the best and objectively unbeatable anti-big-brother solutions, there will still be a hard-core conspiracy theory crowd claiming it just ain't so. With this in mind, one potential solution is to set up a single program registry which is largely a public or non-profit institution to handling and coordinating the realtime verification networks. Such an entity would then have company clients as well as user clients. An organization such as the Software Publishers Association, for example, may choose to lead such an effort.

Concluding this section, it should be re-emphasized that the methods here outlined require a highly connected distributed system, in other words, a more ubiquitous and inexpensive Internet than exists in mid 1995. Simple trend extrapolation would argue that this is not too far off from 1995. The growth rate in raw digital communications bandwidth also argues that the above system might be more practical, sooner, than it might first appear. (The prospect of interactive TV brings with it the promise of a fast network linking millions of sites around the world.)

Use of Current Cryptology Methods in Conjunction with this Invention

It should be briefly noted that certain implementations of the principles of this invention probably can make good use of current cryptographic technologies. One case in point might be a system whereby graphic artists and digital photographers perform realtime registration of their photographs with the copyright office. It might be advantageous to send the master code signals, or some representative portion thereof, directly to a third party registry. In this case, a photographer would want to know that their codes were being transmitted securely and not stolen along the way. In this case, certain common cryptographic transmission might be employed. Also, photographers or musicians, or any users of this invention, may want to have reliable time stamping services which are becoming more common. Such a service could be advantageously used in conjunction with the principles of this invention.

Details on the Legitimate and Illegitimate Detection and Removal of Invisible Signatures In general, if a given entity can recognize the signatures hidden within a given set of empirical data, that same entity can take steps to remove those signatures. In practice, the degree of difficulty between the former condition and the latter condition can be made quite large, fortunately. On one extreme, one could posit a software program which is generally very difficult to "decompile" and which does recognition functions on empirical data. This same bit of software could not generally be used to "strip" the signatures (without going to extreme lengths). On the other hand, if a hacker goes to the trouble of discovering and understanding the "public codes" used within some system of data interchange, and that hacker knows how to recognize the signatures, it would not be a large step for that hacker to read in a given set of signed data and create a data set with the signatures effectively removed. In this latter example, interestingly enough, there would often be telltale statistics that signatures had been removed, statistics which will not be discussed here.

These and other such attempts to remove the signatures we can refer to as illicit attempts. Current and past evolution of the copyright laws have generally targeted such activity as coming under criminal activity and have usually placed such language, along with penalties and enforcement language, into the standing laws. Presumably any and all practitioners of this signature technology will go to lengths to make sure that the same kind of a) creation, b) distribution, and c) use of these kinds of illicit removal of copyright protection mechanisms are criminal offenses subject to enforcement and penalty. On the other hand, it is an object of this invention to point out that through the recognition steps outlined in this disclosure, software programs can be made such that the recognition of signatures can simply lead to their removal by inverting the known signatures by the amount equal to their found signal energy in the recognition process (i.e., remove the size of the given code signal by exact amount found). By pointing this out in this disclosure, it is clear that such software or hardware which performs this signature removal operation will not only (presumably) be criminal, but it will also be liable to infringement to the extent that it is not properly licensed by the holders of the (presumably) patented technology.

The case of legitimate and normal recognition of the signatures is straightforward. In one example, the public signatures could deliberately be made marginally visible (i.e. their intensity would be deliberately high), and in this way a form of sending out "proof comps" can be accomplished. "Comps" and "proofs" have been used in the photographic industry for quite some time, where a degraded image is purposely sent out to prospective customers so that they might evaluate it but not be able to use it in a commercially meaningful way. In the case of this invention, increasing the intensity of the public codes can serve as a way to "degrade" the commercial value intentionally, then through hardware or software activated by paying a purchase price for the material, the public signatures can be removed (and possibly replaced by a new invisible tracking code or signature, public and/or private.

Monitoring Stations and Monitoring Services

Ubiquitous and cost effective recognition of signatures is a central issue to the broadest proliferation of the principles of this invention. Several sections of this disclosure deal with this topic in various ways. This section focuses on the idea that entities such as monitoring nodes, monitoring stations, and monitoring agencies can be created as part of a systematic enforcement of the principles of the invention. In order for such entities to operate, they require knowledge of the master codes, and they may require access to empirical data in its raw (unencrypted and untransformed) form. (Having access to original unsigned empirical data helps in finer analyses but is not necessary.)

Three basic forms of monitoring stations fall out directly from the admittedly arbitrarily defined classes of master codes: a private monitoring station, a semi-public, and a public. The distinctions are simply based on the knowledge of the master codes. An example of the fully private monitoring station might be a large photographic stock house which decides to place certain basic patterns into its distributed material which it knows that a truly crafty pirate could decipher and remove, but it thinks this likelihood is ridiculously small on an economic scale. This stock house hires a part-time person to come in and randomly check high value ads and other photography in the public domain to search for these relatively easy to find base patterns, as well as checking photographs that stock house staff members have "spotted" and think it might be infringement material. The part time person cranks through a large stack of these potential infringement cases in a few hours, and where the base patterns are found, now a more thorough analysis takes place to locate the original image and go through the full process of unique identification as outlined in this disclosure. Two core economic values accrue to the stock house in doing this, values which by definition will outweigh the costs of the monitoring service and the cost of the signing process itself. The first value is in letting their customers and the world know that they are signing their material and that the monitoring service is in place, backed up by whatever statistics on the ability to catch infringers. This is the deterrent value, which probably will be the largest value eventually. A general pre-requisite to this first value is the actual recovered royalties derived from the monitoring effort and its building of a track record for being formidable (enhancing the first value).

The semi-public monitoring stations and the public monitoring stations largely follow the same pattern, although in these systems it is possible to actually set up third party services which are given knowledge of the master codes by clients, and the services merely fish through thousands and millions of "creative property" hunting for the codes and reporting the results to the clients. ASCAP and BMI have "lower tech" approaches to this basic service.

A large coordinated monitoring service using the principles of this invention would classify its creative property supplier clients into two basic categories, those that provide master codes themselves and wish the codes to remain secure and unpublished, and those that use generally public domain master codes (and hybrids of the two, of course). The monitoring service would perform daily samplings (checks) of publicly available imagery, video, audio, etc., doing high level pattern checks with a bank of supercomputers. Magazine ads and images would be scanned in for analysis, video grabbed off of commercial channels would be digitized, audio would be sampled, public Internet sites randomly downloaded, etc. These basic data streams would then be fed into an ever-churning monitoring program which randomly looks for pattern matches between its large bank of public and private codes, and the data material it is checking. A small sub-set, which itself will probably be a large set, will be flagged as potential match candidates, and these will be fed into a more refined checking system which begins to attempt to identify which exact signatures may be present and to perform a more fine analysis on the given flagged material. Presumably a small set would then fall out as flagged match material, owners of that material would be positively identified and a monitoring report would be sent to the client so that they can verify that it was a legitimate sale of their material. The same two values of the private monitoring service outlined above apply in this case as well. The monitoring service could also serve as a formal bully in cases of a found and proven infringement, sending out letters to infringing parties witnessing the found infringement and seeking inflated royalties so that the infringing party might avoid the more costly alternative of going to court.

What is claimed is:

1. A method comprising:
using a programmed electronic processor, generating authentication information corresponding to semantic information to be carried on or in a document; and
incorporating the authentication information on or in the document, in which incorporated authentication information is to be later obtainable from the document for comparison with the semantic information, and in which the authentication information is steganographically incorporated on or in the document so as to be machine-readable from the document with visible light scanning.

2. A computer readable memory including instructions stored thereon to cause an electronic processor to perform the method of claim 1.

3. An apparatus comprising:
electronic memory for storing visible light image data corresponding to a document, the document including semantic information and steganographically encoded authentication information corresponding to the semantic information; and
an electronic processor programmed for:
analyzing the image data to decode the authentication information therefrom; and providing the authentication information for comparison with the semantic information.

4. The apparatus of claim 3 in which said electronic processor is operating to perform at least one of the functions recited therein.

5. A physical document comprising:
semantic information; and
authentication information steganographically hidden on or in the document, in which the authentication information can be machine-read from the document for comparison with the semantic information to determine authenticity of the document, and in which the authentication information is provided so as to be machine-readable from the document with visible light scanning.

* * * * *